US008445196B2

(12) United States Patent
Drmanac et al.

(10) Patent No.: US 8,445,196 B2
(45) Date of Patent: *May 21, 2013

(54) SINGLE MOLECULE ARRAYS FOR GENETIC AND CHEMICAL ANALYSIS

(75) Inventors: Radoje T. Drmanac, Los Altos Hills, CA (US); Matthew J. Callow, Redwood City, CA (US); Snezana Drmanac, Los Altos Hills, CA (US); Brian K. Hauser, Campbell, CA (US); George Yeung, Mountain View, CA (US)

(73) Assignee: Callida Genomics, Inc., Sunnyvale, CA (US)

( * ) Notice: Subject to any disclaimer, the term of this patent is extended or adjusted under 35 U.S.C. 154(b) by 389 days.

This patent is subject to a terminal disclaimer.

(21) Appl. No.: 11/981,767

(22) Filed: Oct. 31, 2007

(65) Prior Publication Data

US 2009/0137404 A1 May 28, 2009

Related U.S. Application Data

(63) Continuation of application No. 11/451,691, filed on Jun. 13, 2006.

(60) Provisional application No. 60/776,415, filed on Feb. 24, 2006, provisional application No. 60/725,116, filed on Oct. 7, 2005, provisional application No. 60/690,771, filed on Jun. 15, 2005.

(51) Int. Cl.
*C12Q 1/68* (2006.01)
*C07H 21/04* (2006.01)
*C12M 1/36* (2006.01)

(52) U.S. Cl.
USPC ........ 435/6.1; 435/287.2; 536/23.1; 536/24.2

(58) Field of Classification Search
None
See application file for complete search history.

(56) References Cited

U.S. PATENT DOCUMENTS

| | | | |
|---|---|---|---|
| 4,719,179 A | 1/1988 | Baranay | 435/172.1 |
| 4,883,750 A | 11/1989 | Whiteley | 435/6 |

(Continued)

FOREIGN PATENT DOCUMENTS

| | | |
|---|---|---|
| WO | WO 95/09248 | 4/1995 |
| WO | WO 01/62982 | 8/2001 |

(Continued)

OTHER PUBLICATIONS

Finzi, et al "Measurement of lactose repressor-mediated loop fomration and breakdown in single DNA molecules" Science 1995, 267: 378-380.*

(Continued)

*Primary Examiner* — Betty Forman
(74) *Attorney, Agent, or Firm* — Kilpatrick Townsend & Stockton LLP

(57) ABSTRACT

Random arrays of single molecules are provided for carrying out large scale analyses, particularly of biomolecules, such as genomic DNA, cDNAs, proteins, and the like. In one aspect, arrays of the invention comprise concatemers of DNA fragments that are randomly disposed on a regular array of discrete spaced apart regions, such that substantially all such regions contain no more than a single concatemer. Preferably, such regions have areas substantially less than 1 μm² and have nearest neighbor distances that permit optical resolution of on the order of $10^9$ single molecules per cm². Many analytical chemistries can be applied to random arrays of the invention, including sequencing by hybridization chemistries, sequencing by synthesis chemistries, SNP detection chemistries, and the like, to greatly expand the scale and potential applications of such techniques.

21 Claims, 13 Drawing Sheets

U.S. PATENT DOCUMENTS

| | | | |
|---|---|---|---|
| 5,091,302 A | 2/1992 | Newman | 435/6 |
| 5,124,246 A | 6/1992 | Urdea | 435/6 |
| 5,143,854 A | 9/1992 | Pirrung | 436/518 |
| 5,202,231 A | 4/1993 | Drmanac | 435/6 |
| 5,354,668 A | 10/1994 | Auerbach | 435/91.1 |
| 5,403,708 A | 4/1995 | Brennan | 435/6 |
| 5,426,180 A | 6/1995 | Kool | 536/25.3 |
| 5,427,930 A | 6/1995 | Birkenmeyer | 435/91.52 |
| 5,474,796 A | 12/1995 | Brennan | 427/2.13 |
| 5,508,169 A | 4/1996 | Deugau | 435/6 |
| 5,525,464 A | 6/1996 | Drmanac | 435/6 |
| 5,571,677 A | 11/1996 | Gryaznov | 435/6 |
| 5,632,957 A | 5/1997 | Heller | 422/68.1 |
| 5,641,658 A | 6/1997 | Adams | 435/91.2 |
| 5,648,245 A | 7/1997 | Fire | 435/91.1 |
| 5,710,000 A | 1/1998 | Sapolsky | 435/6 |
| 5,714,320 A | 2/1998 | Kool | 435/6 |
| 5,728,524 A | 3/1998 | Sibson | 435/6 |
| 5,744,305 A | 4/1998 | Fodor | 435/6 |
| 5,800,992 A | 9/1998 | Fodor | 435/6 |
| 5,854,033 A | 12/1998 | Lizardi | 435/91.2 |
| 5,866,337 A | 2/1999 | Schon | 435/6 |
| 5,869,245 A | 2/1999 | Yeung | 435/6 |
| 5,871,921 A | 2/1999 | Landegren | 435/66 |
| 5,888,737 A | 3/1999 | DuBridge | 435/6 |
| 5,916,750 A | 6/1999 | Iyer | 435/6 |
| 5,994,068 A | 11/1999 | Guilfoyle | 435/6 |
| 6,004,755 A | 12/1999 | Wang | 435/6 |
| 6,013,445 A | 1/2000 | Albrecht | 435/6 |
| 6,045,994 A | 4/2000 | Zabeau | 435/6 |
| 6,077,668 A | 6/2000 | Kool | 435/6 |
| 6,096,880 A | 8/2000 | Kool | 536/25.3 |
| 6,124,120 A | 9/2000 | Lizardi | 435/91.2 |
| 6,136,537 A | 10/2000 | Macevicz | 435/6 |
| 6,143,495 A | 11/2000 | Lizardi | 435/6 |
| 6,143,527 A | 11/2000 | Pachuk | 435/91.1 |
| 6,210,891 B1 | 4/2001 | Nyren | 435/6 |
| 6,210,894 B1 | 4/2001 | Brennan | 435/6 |
| 6,218,152 B1 | 4/2001 | Auerbach | 435/91.2 |
| 6,221,603 B1 | 4/2001 | Mahtani | 435/6 |
| 6,255,469 B1 | 7/2001 | Seeman | 536/23.1 |
| 6,258,539 B1 | 7/2001 | Hunkapillar | 435/6 |
| 6,261,808 B1 | 7/2001 | Auerbach | 435/91.1 |
| 6,270,961 B1 | 8/2001 | Drmanac | 435/6 |
| 6,274,320 B1 | 8/2001 | Rothberg | 435/6 |
| 6,274,351 B1 | 8/2001 | Peponnet | 435/91.1 |
| 6,284,497 B1 | 9/2001 | Sabanayagam | 435/91.2 |
| 6,287,824 B1 | 9/2001 | Lizardi | 435/91.2 |
| 6,289,144 B1 | 9/2001 | Neuschafer | 385/12 |
| 6,291,183 B1 | 9/2001 | Pirrung | 435/6 |
| 6,297,006 B1 | 10/2001 | Drmanac | 435/6 |
| 6,297,016 B1 | 10/2001 | Egholm | 435/6 |
| 6,306,597 B1 | 10/2001 | Macevicz | 435/6 |
| 6,309,824 B1 | 10/2001 | Drmanac | 435/6 |
| 6,316,229 B1 | 11/2001 | Lizardi | 435/91.1 |
| 6,329,150 B1 | 12/2001 | Lizardi | 435/6 |
| 6,344,329 B1 | 2/2002 | Lizardi | 435/6 |
| 6,346,413 B1 | 2/2002 | Fodor | 435/287.2 |
| 6,355,432 B1 | 3/2002 | Fodor | 435/6 |
| 6,401,267 B1 | 6/2002 | Drmanac | 435/6 |
| 6,403,320 B1 | 6/2002 | Read | 435/6 |
| 6,413,722 B1 | 7/2002 | Arnold | 435/6 |
| 6,432,360 B1 | 8/2002 | Church | 422/68.1 |
| 6,472,156 B1 | 10/2002 | Wittwer | 435/6 |
| 6,491,871 B1 | 12/2002 | Fodor | 422/63 |
| 6,500,620 B2 | 12/2002 | Yu | 435/6 |
| 6,514,768 B1 | 2/2003 | Guire | 436/518 |
| 6,534,293 B1 | 3/2003 | Baranay | 435/91.2 |
| 6,558,928 B1 | 5/2003 | Landegren | 435/91.1 |
| 6,573,369 B2 | 6/2003 | Henderson | 536/23.1 |
| 6,576,448 B2 | 6/2003 | Weissman | 435/91.2 |
| 6,589,726 B1 | 7/2003 | Butler | 435/4 |
| 6,610,481 B2 | 8/2003 | Koch | 435/6 |
| 6,620,584 B1 | 9/2003 | Chee | 435/6 |
| 6,632,609 B2 | 10/2003 | Lizardi | 435/6 |
| 6,653,077 B1 | 11/2003 | Brenner | 435/6 |
| 6,654,505 B2 | 11/2003 | Bridgham | 382/278 |
| 6,783,943 B2 | 8/2004 | Christian | 435/6 |
| 6,787,308 B2 | 9/2004 | Balasubramanian | |
| 6,812,005 B2 | 11/2004 | Fan | 435/91.2 |
| 6,864,052 B1 | 3/2005 | Drmanac | 435/6 |
| 6,890,741 B2 | 5/2005 | Fan | 435/91.2 |
| 6,913,884 B2 | 7/2005 | Stuelpnagel | 435/6 |
| 6,977,153 B2 | 12/2005 | Kumar | 435/6 |
| 6,998,228 B2 | 2/2006 | Henderson | 435/4 |
| 7,011,945 B2 | 3/2006 | Qiao | 435/6 |
| 7,064,197 B1 | 6/2006 | Rabbani | 536/24.3 |
| 7,244,559 B2* | 7/2007 | Rothberg et al. | 435/6 |
| 7,264,929 B2 | 9/2007 | Rothberg | 435/6 |
| 7,276,720 B2 | 10/2007 | Ulmer | 356/246 |
| 7,384,737 B2* | 6/2008 | Barnes | 435/6 |
| 7,544,473 B2 | 6/2009 | Brenner | 435/6 |
| 2002/0004204 A1 | 1/2002 | O'Keefe | 435/6 |
| 2002/0055100 A1 | 5/2002 | Kawashima | 435/6 |
| 2002/0076716 A1 | 6/2002 | Sabanayagam | 435/6 |
| 2002/0197621 A1 | 12/2002 | Drmanac | 435/6 |
| 2003/0068629 A1 | 4/2003 | Rothberg | 435/6 |
| 2003/0170914 A1 | 9/2003 | Guire | 435/518 |
| 2004/0002090 A1 | 1/2004 | Mayer | 435/6 |
| 2004/0106110 A1* | 6/2004 | Balasubramanian et al. | 435/6 |
| 2004/0224325 A1 | 11/2004 | Knapp | 435/6 |
| 2004/0229221 A1 | 11/2004 | Schon | 435/6 |
| 2004/0248144 A1 | 12/2004 | Mir | 435/6 |
| 2004/0248161 A1 | 12/2004 | Rothberg | 435/6 |
| 2005/0019776 A1 | 1/2005 | Callow et al. | |
| 2005/0037356 A1 | 2/2005 | Gullberg | 435/6 |
| 2005/0042649 A1 | 2/2005 | Balasubramanian | 435/6 |
| 2005/0059022 A1 | 3/2005 | Ruan et al. | |
| 2005/0100939 A1 | 5/2005 | Namsaraev | 435/6 |
| 2005/0191656 A1 | 9/2005 | Drmanac | 435/6 |
| 2005/0214840 A1 | 9/2005 | Chen | 435/6 |
| 2005/0244863 A1 | 11/2005 | Mir | 435/6 |
| 2006/0012793 A1 | 1/2006 | Harris | 356/246 |
| 2006/0019276 A1* | 1/2006 | Harris et al. | 435/6 |
| 2006/0024681 A1 | 2/2006 | Smith | 435/6 |
| 2006/0024711 A1 | 2/2006 | Lapidus | 435/6 |
| 2006/0223097 A1 | 10/2006 | Sapolsky et al. | |
| 2007/0015182 A1 | 1/2007 | Abarzua | 435/6 |
| 2008/0318796 A1* | 12/2008 | Drmanac et al. | 506/3 |
| 2009/0018024 A1 | 1/2009 | Church et al. | |
| 2009/0099041 A1 | 4/2009 | Church et al. | |
| 2009/0137414 A1* | 5/2009 | Drmanac et al. | 506/9 |
| 2009/0176652 A1 | 7/2009 | Dahl et al. | |
| 2009/0203551 A1 | 8/2009 | Dahl et al. | |
| 2009/0264299 A1* | 10/2009 | Drmanac et al. | 506/3 |

FOREIGN PATENT DOCUMENTS

| | | |
|---|---|---|
| WO | WO 02/074988 | 9/2002 |
| WO | WO 03/012119 | 2/2003 |
| WO | 03/102231 A1 | 12/2003 |
| WO | WO 2004/072294 | 8/2004 |
| WO | WO 2004/076683 | 9/2004 |
| WO | WO 2005/040425 | 5/2005 |
| WO | WO 2005/047523 | 5/2005 |
| WO | WO 2005/078130 | 8/2005 |
| WO | WO 2005/080605 | 9/2005 |
| WO | WO 2005/082098 | 9/2005 |
| WO | WO 2005/093094 | 10/2005 |
| WO | WO 2005/116262 | 12/2005 |
| WO | WO 2006/007207 | 1/2006 |
| WO | WO 2006/040549 | 4/2006 |
| WO | WO 2006/055521 | 5/2006 |
| WO | WO 2006/073504 | 7/2006 |
| WO | WO 2006/084132 | 8/2006 |
| WO | WO 2007/014397 | 2/2007 |
| WO | WO 2007/025124 | 3/2007 |
| WO | WO 2007/061425 | 5/2007 |
| WO | WO 2007/062160 | 5/2007 |

OTHER PUBLICATIONS

Amersham Biosciences product brochure, "Passport kits for EMD assays: a novel tool for high-throughput SNP analysis and mutation scanning," Life Science News 2 (1999).

Babon et al, "Mutation detection using fluorescent enzyme mismatch cleavage with T4 endonuclease VII," Electrophoresis, 20: 1162-1170 (1999).

Beaucage, "Strategies in the preparation of DNA oligonucleotide arrays for diagnostic applications," Curr. Med. Chem., 8: 1213-1244 (2001).

Collins et al, "Directional cloning of DNA fragments at a large distance from an initial probe: A circularization method," Proc. Natl. Acad. Sci., 81: 6812-6816 (1984).

Cowie et al, "Identification of APC gene mutations in colorectal cancer using universal microarray-based combinatorial sequencing-by-hybridization," Human Mutation, 24: 261-271 (2004).

Dahl et al, "Multiplex amplification enabled by selective circularization of large sets of genomic DNA fragments," Nucleic Acids Research, 33(8): e71 (2005).

Drmanac et al, "Sequencing by hybridization (SBH): advantages, achievements, and opportunities," Adv. Biochem. Engineering/Biotechnology, 77: 76-101 (2002).

Epicentre Biotechnologies product brochure No. 222, "CircLigase ssDNA Ligase," (Aug. 2005).

Gerry et al, "Universal DNA microarray method for multiplex detection of low abundance point mutations," J. Mol. Biol., 292: 251-262 (1999).

Gunderson et al, "Mutation detection by ligation to complete n-mer DNA arrays," Genome Research, 8: 1142-1153 (1998).

Inganas et al, "Enzymatic mutation detection in the P53 gene," Clin. Chem., 46: 1562-1573 (2000).

Kandpal et al, "Selective enlargement of a large size genomic DNA fragment by affinity capture: an approach for genome mapping," Nucleic Acids Research, 18: 1789 (1990).

Kool, "Circular oligonucleotides: New concepts in oligonucleotide design," Annu. Rev. Biophys. Biomol. Struct., 25: 1-28 (1996).

Lehr et al, "Real-time detection of nucleic acid interactions by total internal reflection fluorescence," Anal. Chem., 75: 2414-2420 (2003).

Lizardi et al, "Mutation detection and single-molecule counting using isothermal rolling-circle amplification," Nature Genetics, 19: 225-232 (1998).

Mashal et al, "Detection of mutations by cleavage of DNA heteroduplexes with bacteriophage resolvases," Nature Genetics, 9: 177-183 (1995).

McGall et al, "High-density GeneChip oligonucleotide probe arrays," Adv. Biochem. Engineering/Biotechnology, 77: 22 (2002).

Mitra et al, "In situ localized amplification and contact replication of many individual DNA molecules," Nucleic Acids Research, 27(24): e34 (1999).

Nallur et al, "Signal amplification by rolling circle amplification on DNA microarrays," Nucleic Acids Research, 29(23): e118 (2001).

Neuschafer et al, "Evanescent resonator chips: a universal platform with superior sensitivity for fluorescence-based microarrays," Biosensors and Bioelectronics, 18: 489-497 (2003).

Nie et al, "Scoring single-nucleotide polymorphisms at the single molecule level by counting individual DNA cleavage events on a surface," Anal. Chem., 77: 6594-6600 (2005).

Parsons et al, "Genotypic selection methods for the direct analysis of point mutations," Mutation Research, 387: 97-121 (1997).

Parsons et al, "Evaluation of MutS as a tool for direct measurement of point mutations in genomic DNA," Mutation Research, 374: 277-285 (1997).

Pohl et al, "Construction of a Not I linking library and isolation of new markers close to Huntington's disease gene," Nucleic Acids Research, 16: 9185-9198 (1988).

Predki et al, "Rolling circle amplification for sequencing templates," Methods Mol. Biol., 255: 189-196 (2004).

Sasuga et al, "Development of a microscopic platform for real-time monitoring of biomolecular interactions," Genome Research, 16: 132-139 (2006).

Shendure et al, "Accurate multiplex polony sequencing of an evolved bacterial genome," Science, 309: 1728-1732 (2005).

Smirnov et al, "Method of manufacturing whole-genome microarrays by rolling circle amplification," Genes, Chromosomes & Cancer, 40: 72-77 (2004).

Taylor, "Enzymatic and chemical cleavage methods," Electrophoresis, 20: 1125-1130 (1999).

Wazawa et al, "Total internal reflection fluorescence microscopy in single molecule nanobioscience," Adv. Biochem. Engineering/Biotechnology, 95: 77-106 (2005).

Weiss, "Fluorescence spectroscopy of single biomolecules," Science, 283: 1676 (1999).

Yamakawa et al, "A simple and robust method for preparation of cDNA nylon microarrays," DNA Research, 11: 353-360 (2004).

Zhang et al, "Amplification of target-specific, ligation-dependent circular probe," Gene, 211: 277-285 (1998).

Blanco et al., "Highly efficient DNA synthesis by the phage phi 29 DNA polymerase," J. Biol. Chem., v. 264, issue 15, p. 8935-8940 (1989).

Callow, Matthew J., et al. "Selective DNA amplification from complex genomes using universal double-sided adapters," Nucleic Acids Research, vol. 32, No. 2, e21, p. 1-6, (Jan. 2004).

Chen et al., "A Homogeneous, Ligase-Mediated DNA Diagnostic Test", Genome Research, vol. 8, No. 5, May 1998, pp. 549-556.

Ladner, D.P. et al., "Multiplex detection of hotspot mutations by rolling circl-enabled universal microarrays," Laboratory Investigation, US and CA Academy of Pa;thology, vol. 81, No. 8, p. 1079-1086 (Aug. 1, 2001).

Shendure et al, "Advanced Sequencing Technologies: Methods and Goals," Nature Reviews Genetics, vol. 5, pp. 335-344 (2004).

Tringe et al, "Metagenomics: DNA Sequencing of Environmental Samples," Nature Reviews Genetics, vol. 6, pp. 805-814 (2005).

Vingron et al., "Sequence Alignment and Penalty Choice Review of Concepts, Case Studies and Implications," J. Mol. Biol, vol. 235, issue 1, pp. 1-12 (1994).

Matthew Callow et al., U.S. Appl. No. 60/690,771—*Methods and Applications for Random DNA Array Preparation*, filed Jun. 15, 2005, Priority application to U.S. Appl. No. 11/981,767.

Radoje Dramanc et al., U.S. Appl. No. 60/725,116—*Ultra-High Capacity Self-Assembled Detector Nano-Array (saDNA) Chips*, filed Oct. 7, 2005, Priority application to U.S. Appl. No. 11/981,767.

Radoje Dramanc et al., U.S. Appl. No. 60/776,415—*Efficent Genome Analysis by Combinatorial Probe Ligation on DNA Arrays*, filed Feb. 24, 2006, Priority application to U.S. Appl. No. 11/981,767.

Supplementary Search Report for EP Application No. 06815722.1, mailed on Dec. 22, 2009, 9 pages.

* cited by examiner

SINGLE MOLECULE ARRAYS FOR GENETIC AND CHEMICAL ANALYSIS This application is a continuation of U.S. application Ser. No. 11/451,691, filed 13 Jun. 2006, which claims priority from U.S. provisional applications Ser. No. 60/776,415, filed 24 Feb. 2006, Ser. No. 60/725,116 filed 7 Oct. 2005, and Ser. No. 60/690,771 filed 15 Jun. 2005, each of which is hereby incorporated by reference in its entirety.

GOVERNMENT INTERESTS

This invention was made with government support under grant No. 1 U01 A1057315-01 awarded by the National Institutes of Health. The government has certain rights in the invention.

FIELD OF THE INVENTION

The present invention relates to methods and compositions for high-throughput analysis of populations of individual molecules, and more particularly, to methods and compositions related to fabrication of single molecule arrays and applications thereof, especially in high-throughput nucleic acid sequencing and genetic analysis.

BACKGROUND

Large-scale molecular analysis is central to understanding a wide range of biological phenomena related to states of health and disease both in humans and in a host of economically important plants and animals, e.g. Collins et al (2003), Nature, 422: 835-847; Hirschhorn et al (2005), Nature Reviews Genetics, 6: 95-108; National Cancer Institute, Report of Working Group on Biomedical Technology, "Recommendation for a Human Cancer Genome Project," (February, 2005). Miniaturization has proved to be extremely important for increasing the scale and reducing the costs of such analyses, and an important route to miniaturization has been the use of microarrays of probes or analytes. Such arrays play a key role in most currently available, or emerging, large-scale genetic analysis and proteomic techniques, including those for single nucleotide polymorphism detection, copy number assessment, nucleic acid sequencing, and the like, e.g. Kennedy et al (2003), Nature Biotechnology, 21: 1233-1237; Gunderson et al (2005), Nature Genetics, 37: 549-554; Pinkel and Albertson (2005), Nature Genetics Supplement, 37: S11-S17; Leamon et al (2003), Electrophoresis, 24: 3769-3777; Shendure et al (2005), Science, 309: 1728-1732; Cowie et al (2004), Human Mutation, 24: 261-271; and the like. However, the scale of microarrays currently used in such techniques still falls short of that required to meet the goals of truly low cost analyses that would make practical such operations as personal genome sequencing, environmental sequencing to use changes in complex microbial communities as an indicator of states of health, either personal or environmental, studies that associate genomic features with complex traits, such as susceptibilities to cancer, diabetes, cardiovascular disease, and the like, e.g. Collins et al (cited above); Hirschhorn et al (cited above); Tringe et al (2005), Nature Reviews Genetics, 6: 805-814; Service (2006), Science, 311: 1544-1546.

Increasing the scale of analysis in array-based schemes for DNA sequencing is particularly challenging as the feature size of the array is decreased to molecular levels, since most schemes require not only a procedure for forming high density arrays, but also repeated cycles of complex biochemical steps that complicate the problems of array integrity, signal generation, signal detection, and the like, e.g. Metzker (2005), Genome Research, 15: 1767-1776; Shendure et al (2004), Nature Reviews Genetics, 5: 335-344; Weiss (1999), Science, 283: 1676-1683. Some approaches have employed high density arrays of unamplified target sequences, which present serious signal-to-noise challenges, when "sequencing by synthesis" chemistries have been used, e.g. Balasubramanian et al, U.S. Pat. No. 6,787,308. Other approaches have employed in situ amplification of randomly disposed target sequences, followed by application of "sequencing by synthesis" chemistries. Such approaches also have given rise to various difficulties, including (i) significant variability in the size of target sequence clusters, (ii) gradual loss of phase in extension steps carried out by polymerases, (iii) lack of sequencing cycle efficiency that inhibits read lengths, and the like, e.g. Kartalov et al, Nucleic Acids Research, 32: 2873-2879 (2004); Mitra et al, Anal. Biochem., 320: 55-65 (2003); Metzker (cited above).

In view of the above, it would be advantageous for the medical, life science, and agricultural fields if there were available molecular arrays and arraying techniques that permitted efficient and convenient analysis of large numbers of individual molecules, such as DNA fragments covering substantially an entire mammalian-sized genome, in parallel in a single analytical operation.

SUMMARY OF THE INVENTION

In one aspect, the invention provides high density single molecule arrays, methods of making and using such compositions, and kits for implementing such methods. Compositions of the invention in one form include random arrays of a plurality of different single molecules disposed on a surface, where the single molecules each comprise a macromolecular structure and at least one analyte, such that each macromolecular structure comprises a plurality of attachment functionalities that are capable of forming bonds with one or more functionalities on the surface. In one aspect, the analyte is a component of the macromolecular structure, and in another aspect, the analyte is attached to the macromolecular structure by a linkage between a unique functionality on such structure and a reactive group or attachment moiety on the analyte. In another aspect, compositions of the invention include random arrays of single molecules disposed on a surface, where the single molecules each comprise a concatemer of at least one target polynucleotide and each is attached to the surface by linkages formed between one or more functionalities on the surface and complementary functionalities on the concatemer. In another form, compositions of the invention include random arrays of single molecules disposed on a surface, where the single molecules each comprise a concatemer of at least one target polynucleotide and at least one adaptor oligonucleotide and each is attached to such surface by the formation of duplexes between capture oligonucleotides on the surface and the attachment oligonucleotides in the concatemer. In still another form, compositions of the invention include random arrays of single molecules disposed on a surface, where each single molecule comprises a bifunctional macromolecular structure having a unique functionality and a plurality of complementary functionalities, and where each single molecule is attached to the surface by linkages between one or more functionalities on the surface and complementary functionalities on the bifunctional macromolecular structure, the unique functionality having an orthogonal chemical reactivity with respect to the complementary functionalities and being capable of forming a covalent linkage with an analyte. In regard to the above compositions, in another aspect, such single molecules are disposed in a planar array randomly distributed onto discrete spaced apart regions having defined positions. Preferably, in this aspect, the discrete spaced apart regions each have an area that permits the capture of no more than a single molecule and each is surrounded by an inter-regional space that is substantially free of other single molecules.

In one aspect, the invention includes an array of polymer molecules comprising: (a) a support having a surface; and (b) a plurality of polymer molecules attached to the surface, wherein each polymer molecule has a random coil state and comprises a branched or linear structure of multiple copies of one or more linear polymeric units, such that the polymer molecule is attached to the surface within a region substantially equivalent to a projection of the random coil on the surface and randomly disposed at a density such that at least thirty percent of the polymer molecules are separately detectable. As discussed more fully below, whenever the polymer molecules are linear, in one embodiment, "substantially equivalent" in reference to the above projection means a substantially circular region with a diameter equal to the root mean square of the end-to-end distance of such linear polymer. In another embodiment, for linear or branched polymers, "substantially equivalent" means a substantially circular region having a diameter that is one half or less than the total length of the polymer; or in another embodiment one tenth or less; or in another embodiment, one hundredth or less.

In another aspect, the invention includes an array of polynucleotide molecules comprising: (a) a support having a surface; and (b) a plurality of polynucleotide molecules attached to the surface, wherein each polynucleotide molecule has a random coil state and comprises a concatemer of multiple copies of a target sequence such that the polynucleotide molecule is attached to the surface within a region substantially equivalent to a projection of the random coil on the surface and randomly disposed at a density such that at least thirty percent of the polynucleotide molecules have a nearest neighbor distance of at least fifty nm.

A method of making arrays of provided polymer molecules wherein each polymer molecule has a random coil or similar or other three-dimensional state and comprises a branched or linear structure of multiple copies of one or more linear polymeric units, such that the existing polymer molecule is attached to the surface within a region substantially equivalent to a projection of the random coil on the surface or a region having size that is one half or less, one tenth or less or one hundredth or less of the total length of the polymer, and randomly disposed at a density such that at least twenty or at least thirty percent of the polymer molecules are separately detectable.

In still another aspect, the invention provides an array of single molecules comprising: (a) a support having a planar surface having a regular array of discrete spaced apart regions, wherein each discrete spaced apart region has an area of less than 1 µm² and contains reactive functionalities attached thereto; and (b) a plurality of single molecules attached to the surface, wherein each single molecule comprises a macromolecular structure and at least one analyte having an attachment moiety, such that each macromolecular structure comprises a unique functionality and a plurality of attachment functionalities that are capable of forming linkages with the reactive functionalities of the discrete spaced apart regions, and such that the analyte is attached to the macromolecular structure by a linkage between the unique functionality and the attachment moiety of the analyte, wherein the plurality of single molecules are randomly disposed on the discrete spaced apart regions such that at least a majority of the discrete spaced apart regions contain only one single molecule.

In another aspect, the invention provides an array of polynucleotide molecules comprising: (a) a support having a surface with capture oligonucleotides attached thereto; and (b) a plurality of polynucleotide molecules attached to the surface, wherein each polynucleotide molecule comprises a concatemer of multiple copies of a target sequence and an adaptor oligonucleotide such that the polynucleotide molecule is attached to the surface by one or more complexes formed between capture oligonucleotides and adaptor oligonucleotides, the polynucleotide molecules being randomly disposed on the surface at a density such that at least a majority of the polynucleotide molecules have a nearest neighbor distance of at least fifty nm. In one embodiment of this aspect, the surface is a planar surface having an array of discrete spaced apart regions, wherein each discrete spaced apart region has a size equivalent to that of the polynucleotide molecule and contains the capture oligonucleotides attached thereto and wherein substantially all such regions have at most one of the polynucleotide molecules attached.

The invention further includes, a method of making an array of polynucleotide molecules comprising the following steps: (a) generating a plurality of polynucleotide molecules each comprising a concatemer of a DNA fragment from a source DNA and an adaptor oligonucleotide; and (b) disposing the plurality of polynucleotide molecules onto a support having a surface with capture oligonucleotides attached thereto so that the polynucleotide molecules are fixed to the surface by one or more complexes formed between capture oligonucleotides and adaptor oligonucleotides and so that the polynucleotide molecules are randomly distributed on the surface at a density such that a majority of the polynucleotide molecules have a nearest neighbor distance of at least fifty nm, thereby forming the array of polynucleotide molecules.

In another aspect, the invention provides a method of determining a nucleotide sequence of a target polynucleotide, the method comprising the steps of: (a) generating a plurality of target concatemers from the target polynucleotide, each target concatemer comprising multiple copies of a fragment of the target polynucleotide and the plurality of target concatemers including a number of fragments that substantially covers the target polynucleotide; (b) forming a random array of target concatemers fixed to a surface at a density such that at least a majority of the target concatemers are optically resolvable; (c) identifying a sequence of at least a portion of each fragment in each target concatemer; and (d) reconstructing the nucleotide sequence of the target polynucleotide from the identities of the sequences of the portions of fragments of the concatemers. In one embodiment of this aspect, the step of identifying includes the steps of (a) hybridizing one or more probes from a first set of probes to the random array under conditions that permit the formation of perfectly matched duplexes between the one or more probes and complementary sequences on target concatemers; (b) hybridizing one or more probes from a second set of probes to the random array under conditions that permit the formation of perfectly matched duplexes between the one or more probes and complementary sequences on target concatemers; (c) ligating probes from the first and second sets hybridized to a target concatemer at contiguous sites; (d) identifying the sequences of the ligated first and second probes; and (e) repeating steps (a through (d) until the sequence of the target polynucleotide can be determined from the identities of the sequences of the ligated probes.

In another aspect, the invention includes kits for making random arrays of the invention and for implementing applications of the random arrays of the invention, particularly high-throughput analysis of one or more target polynucleotides.

The present invention provides a significant advance in the microarray field by providing arrays of single molecules comprising linear and/or branched polymer structures that may incorporate or have attached target analyte molecules. In one form, such single molecules are concatemers of target polynucleotides arrayed at densities that permit efficient high resolution analysis of mammalian-sized genomes, including sequence determination of all or substantial parts of such genomes, sequence determination of tagged fragments from selected regions of multiple genomes, digital readouts of gene expression, and genome-wide assessments of copy number patterns, methylation patterns, chromosomal stability, individual genetic variation, and the like.

DETAILED DESCRIPTION OF THE INVENTION

Figure 1A:
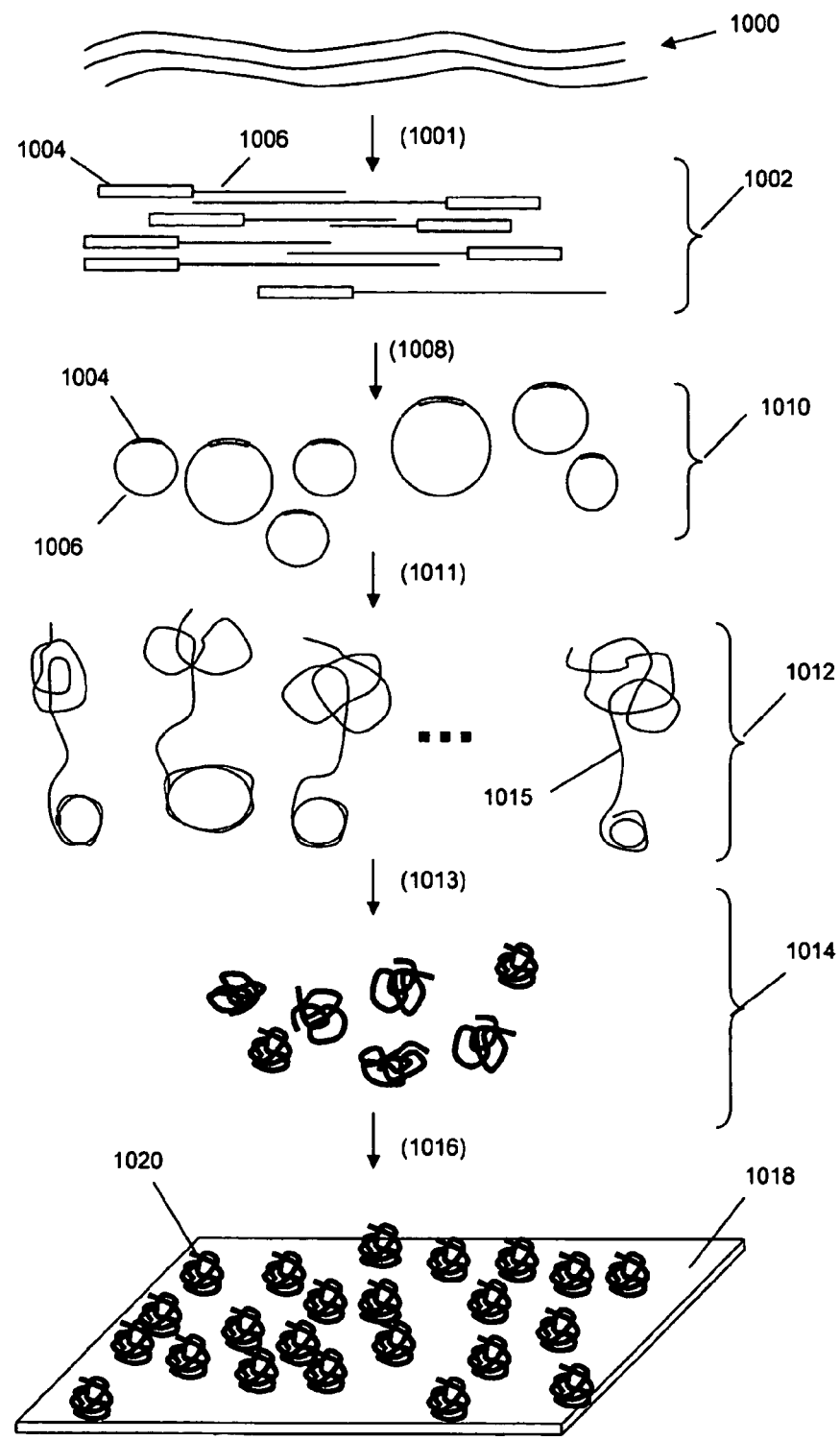
FIGS. 1A-1I illustrate various embodiments of the methods and compositions of the invention.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The invention provides random single molecule arrays for large-scale parallel analysis of populations of molecules, particularly DNA fragments, such as genomic DNA fragments. Generally, single molecules of the invention comprise an attachment portion and an analyte portion. The attachment portion comprises a macromolecular structure that provides for multivalent attachment to a surface, particularly a compact or restricted area on a surface so that signals generated from it or an attached analyte are concentrated. That is, the macromolecular structure occupies a compact and limited region of the surface. Macromolecular structures of the invention may be bound to a surface in a variety of ways. Multivalent bonds may be covalent or non-covalent. Non-covalent bonds include formation of duplexes between capture oligonucleotides on the surface and complementary sequences in the macromolecular structure, and adsorption to a surface by attractive noncovalent interactions, such as Van der Waal forces, hydrogen bonding, ionic and hydrophobic interactions, and the like. Multi-valent covalent bonding may be accomplished, as described more fully below, by providing reactive functionalities on the surface that can reactive with a plurality of complementary functionalities in the macromolecular structures. An analyte portion may be attached to a macromolecular structure by way of a unique linkage or it may form a part of, and be integral with, the macromolecular structure. Single molecules of the invention are disposed randomly on a surface of a support material, usually from a solution; thus, in one aspect, single molecules are uniformly distributed on a surface in close approximation to a Poisson distribution. In another aspect, single molecules are disposed on a surface that contains discrete spaced apart regions in which single molecules are attached. Preferably, macromolecular structures, preparation methods, and areas of such discrete spaced apart regions are selected so that substantially all such regions contain at most only one single molecule. Preferably, single molecules of the invention, particularly concatemers, are roughly in a random coil configuration on a surface and are confined to the area of a discrete spaced apart region. In one aspect, the discrete space apart regions have defined locations in a regular array, which may correspond to a rectilinear pattern, hexagonal pattern, or the like. A regular array of such regions is advantageous for detection and data analysis of signals collected from the arrays during an analysis. Also, single molecules confined to the restricted area of a discrete spaced apart region provide a more concentrated or intense signal, particularly when fluorescent probes are used in analytical operations, thereby providing higher signal-to-noise values. Single molecules of the invention are randomly distributed on the discrete spaced apart regions so that a given region usually is equally likely to receive any of the different single molecules. In other words, the resulting arrays are not spatially addressable immediately upon fabrication, but may be made so by carrying out an identification or decoding operation. That is, the identities of the single molecules are discernable, but not known. As described more fully below, in some embodiments, there are subsets of discrete spaced apart regions that receive single molecules only from corresponding subsets, for example, as defined by complementary sequences of capture oligonucleotides and adaptor oligonucleotides.

Macromolecular structures of the invention comprise polymers, either branched or linear, and may be synthetic, e.g.

branched DNA, or may be derived from natural sources, e.g linear DNA fragments from a patient's genomic DNA. Usually, macromolecular structures comprise concatemers of linear single stranded DNA fragments that can be synthetic, derived from natural sources, or can be a combination of both. As used herein, the term "target sequence" refers to either a synthetic nucleic acid or a nucleic acid derived from a natural source, such as a patient specimen, or the like. Usually, target sequences are part of a concatemer generated by methods of the invention, e.g. by RCR, but may also be part of other structures, such as dendrimers, and other branched structures. When target sequences are synthetic or derived from natural sources, they are usually replicated by various methods in the process of forming macromolecular structures or single molecules of the invention. It is understood that such methods can introduce errors into copies, which nonetheless are encompassed by the term "target sequence."

Particular features or components of macromolecular structures may be selected to satisfy a variety of design objectives in particular embodiments. For example, in some embodiments, it may be advantageous to maintain an analyte molecule as far from the surface as possible, e.g. by providing an inflexible molecular spacer as part of a unique linkage. As another example, reactive functionalities may be selected as having a size that effectively prevents attachment of multiple macromolecular structures to one discrete spaced apart region. As still another example, macromolecular structures may be provided with other functionalities for a variety of other purposes, e.g. enhancing solubility, promoting formation of secondary structures via hydrogen bonding, and the like.

In one aspect, macromolecular structures are sufficiently large that their size, e.g. a linear dimension (such as a diameter) of a volume occupied in a conventional physiological saline solution, is approximately equivalent to that a discrete spaced apart region. For macromolecular structures that are linear polynucleotides, in one aspect, sizes may range from a few thousand nucleotides, e.g. 10,000, to several hundred thousand nucleotides, e.g. 100-200 thousand. As explained more fully below, in several embodiments, such macromolecular structures are made by generating circular DNAs and then replicating them in a rolling circle replication reaction to form concatemers of complements of the circular DNAs.

The above concepts are illustrated more fully in the embodiments shown schematically in FIGS. 1A-1G. After describing these figures, elements of the invention are disclosed in additional detail and examples are given. As mentioned above, in one aspect, macromolecular structures of the invention are single stranded polynucleotides comprising concatemers of a target sequence or fragment. In particular, such polynucleotides may be concatemers of a target sequence and an adaptor oligonucleotide. For example, source nucleic acid (1000) is treated (1001) to form single stranded fragments (1006), preferably in the range of from 50 to 600 nucleotides, and more preferably in the range of from 300 to 600 nucleotides, which are then ligated to adaptor oligonucleotides (1004) to form a population of adaptor-fragment conjugates (1002). Source nucleic acid (1000) may be genomic DNA extracted from a sample using conventional techniques, or a cDNA or genomic library produced by conventional techniques, or synthetic DNA, or the like. Treatment (1001) usually entails fragmentation by a conventional technique, such as chemical fragmentation, enzymatic fragmentation, or mechanical fragmentation, followed by denaturation to produce single stranded DNA fragments. Adaptor oligonucleotides (1004), in this example, are used to form (1008) a population (1010) of DNA circles by the method illustrated in FIG. 2A. In one aspect, each member of population (1010) has an adaptor with an identical primer binding site and a DNA fragment from source nucleic acid (1000). The adapter also may have other functional elements including, but not limited to, tagging sequences, attachment sequences, palindromic sequences, restriction sites, functionalization sequences, and the like. In other embodiments, classes of DNA circles may be created by providing adaptors having different primer binding sites. After DNA circles (1010) are formed, a primer and rolling circle replication (RCR) reagents may be added to generate (1011) in a conventional RCR reaction a population (1012) of concatemers (1015) of the complements of the adaptor oligonucleotide and DNA fragments, which population can then be isolated using conventional separation techniques. Alternatively, RCR may be implemented by successive ligation of short oligonucleotides, e.g. 6-mers, from a mixture containing all possible sequences, or if circles are synthetic, a limited mixture of oligonucleotides having selected sequences for circle replication. Concatemers may also be generated by ligation of target DNA in the presence of a bridging template DNA complementary to both beginning and end of the target molecule. A population of different target DNA may be converted in concatemers by a mixture of corresponding bridging templates. Isolated concatemers (1014) are then disposed (1016) onto support surface (1018) to form a random array of single molecules. Attachment may also include wash steps of varying stringencies to remove incompletely attached single molecules or other reagents present from earlier preparation steps whose presence is undesirable or that are nonspecifically bound to surface (1018). Concatemers (1020) can be fixed to surface (1018) by a variety of techniques, including covalent attachment and non-covalent attachment. In one embodiment, surface (1018) may have attached capture oligonucleotides that form complexes, e.g. double stranded duplexes, with a segment of the adaptor oligonucleotide, such as the primer binding site or other elements. In other embodiments, capture oligonucleotides may comprise oligonucleotide clamps, or like structures, that form triplexes with adaptor oligonucleotides, e.g. Gryaznov et al, U.S. Pat. No. 5,473, 060. In another embodiment, surface (1018) may have reactive functionalities that react with complementary functionalities on the concatemers to form a covalent linkage, e.g. by way of the same techniques used to attach cDNAs to microarrays, e.g. Smirnov et al (2004), Genes, Chromosomes & Cancer, 40: 72-77; Beaucage (2001), Current Medicinal Chemistry, 8: 1213-1244, which are incorporated herein by reference. Long DNA molecules, e.g. several hundred nucleotides or larger, may also be efficiently attached to hydrophobic surfaces, such as a clean glass surface that has a low concentration of various reactive functionalities, such as —OH groups. Concatemers of DNA fragments may be further amplified in situ after disposition of a surface. For example after disposition, concatemer may be cleaved by reconstituting a restriction site in adaptor sequences by hybridization of an oligonucleotide, after which the fragments are circularized as described below and amplified in situ by a RCR reaction.

Figure 1B:
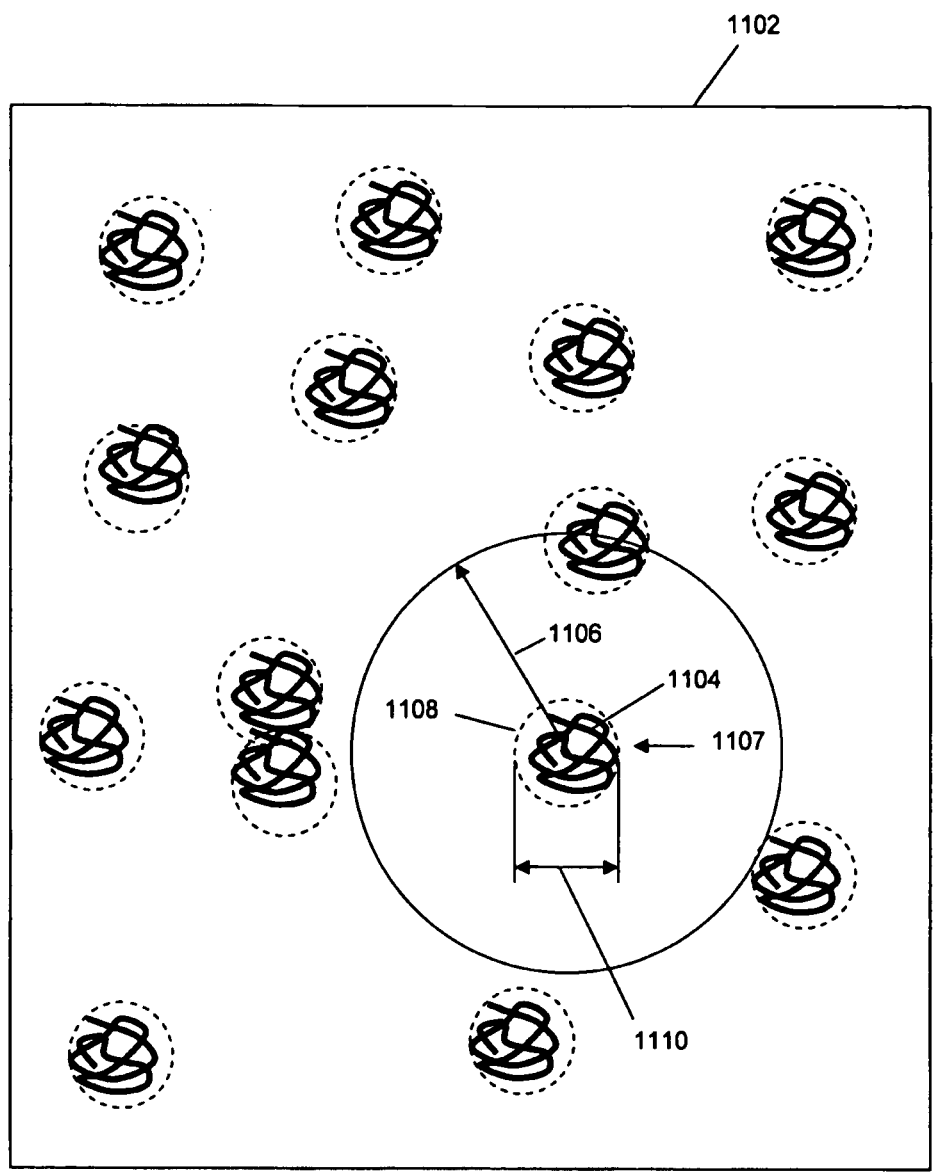
Figure 2A:
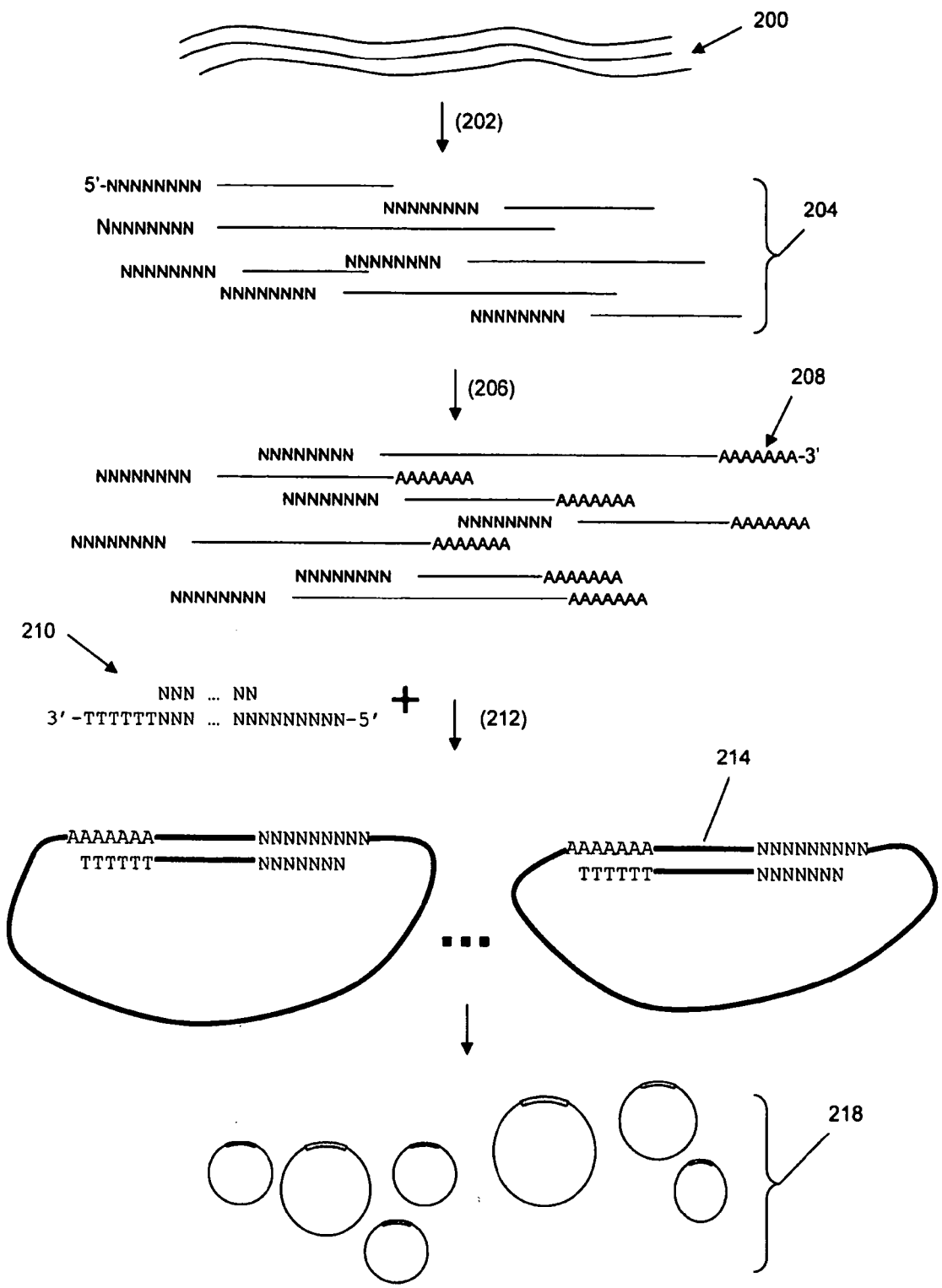
FIGS. 2A-2B illustrate methods of circularizing genomic DNA fragments for generating concatemers of polynucleotide analytes.

FIG. 1B illustrates a section (1102) of a surface of a random array of single molecules, such as single stranded polynucleotides. Such molecules under conventional conditions (a conventional DNA buffer, e.g. TE, SSC, SSPE, or the like, at room temperature) form random coils that roughly fill a spherical volume in solution having a diameter of from about 100 to 300 nm, which depends on the size of the DNA and buffer conditions, in a manner well known in the art, e.g. Edvinsson, "On the size and shape of polymers and polymer complexes," Dissertation 696 (University of Uppsala, 2002). One measure of the size of a random coil polymer, such as single stranded DNA, is a root mean square of the end-to-end distance, which is roughly a measure of the diameter of the randomly coiled structure. Such diameter, referred to herein as a "random coil diameter," can be measured by light scatter, using instruments, such as a Zetasizer Nano System (Malvern Instruments, UK), or like instrument. Additional size measures of macromolecular structures of the invention include molecular weight, e.g. in Daltons, and total polymer length, which in the case of a branched polymer is the sum of the lengths of all its branches. Upon attachment to a surface, depending on the attachment chemistry, density of linkages, the nature of the surface, and the like, single stranded polynucleotides fill a flattened spheroidal volume that on average is bounded by a region (1107) defined by dashed circles (1108) having a diameter (1110), which is approximately equivalent to the diameter of a concatemer in random coil configuration. Stated another way, in one aspect, macromolecular structures, e.g. concatemers, and the like, are attached to surface (1102) within a region that is substantially equivalent to a projection of its random coil state onto surface (1102), for example, as illustrated by dashed circles (1108). An area occupied by a macromolecular structure can vary, so that in some embodiments, an expected area may be within the range of from 2-3 times the area of projection (1108) to some fraction of such area, e.g. 25-50 percent. As mentioned else where, preserving the compact form of the macromolecular structure on the surface allows a more intense signal to be produced by probes, e.g. fluorescently labeled oligonucleotides, specifically directed to components of a macromolecular structure or concatemer. The size of diameter (1110) of regions (1107) and distance (1106) to the nearest neighbor region containing a single molecule are two quantities of interest in the fabrication of arrays. A variety of distance metrics may be employed for measuring the closeness of single molecules on a surface, including center-to-center distance of regions (1107), edge-to-edge distance of regions (1007), and the like. Usually, center-to-center distances are employed herein. The selection of these parameters in fabricating arrays of the invention depends in part on the signal generation and detection systems used in the analytical processes. Generally, densities of single molecules are selected that permit at least twenty percent, or at least thirty percent, or at least forty percent, or at least a majority of the molecules to be resolved individually by the signal generation and detection systems used. In one aspect, a density is selected that permits at least seventy percent of the single molecules to be individually resolved. In one aspect, whenever scanning electron microscopy is employed, for example, with molecule-specific probes having gold nanoparticle labels, e.g. Nie et al (2006), Anal. Chem., 78: 1528-1534, which is incorporated by reference, a density is selected such that at least a majority of single molecules have a nearest neighbor distance of 50 nm or greater; and in another aspect, such density is selected to ensure that at least seventy percent of single molecules have a nearest neighbor distance of 100 nm or greater. In another aspect, whenever optical microscopy is employed, for example with molecule-specific probes having fluorescent labels, a density is selected such that at least a majority of single molecules have a nearest neighbor distance of 200 nm or greater; and in another aspect, such density is selected to ensure that at least seventy percent of single molecules have a nearest neighbor distance of 200 nm or greater. In still another aspect, whenever optical microscopy is employed, for example with molecule-specific probes having fluorescent labels, a density is selected such that at least a majority of single molecules have a nearest neighbor distance of 300 nm or greater; and in another aspect, such density is selected to ensure that at least seventy percent of single molecules have a nearest neighbor distance of 300 nm or greater, or 400 nm or greater, or 500 nm or greater, or 600 nm or greater, or 700 nm or greater, or 800 nm or greater. In still another embodiment, whenever optical microscopy is used, a density is selected such that at least a majority of single molecules have a nearest neighbor distance of at least twice the minimal feature resolution power of the microscope. In another aspect, polymer molecules of the invention are disposed on a surface so that the density of separately detectable polymer molecules is at least 1000 per $\mu m^2$, or at least 10,000 per $\mu m^2$, or at least 100,000 per $\mu m^2$.

Figure 1C:
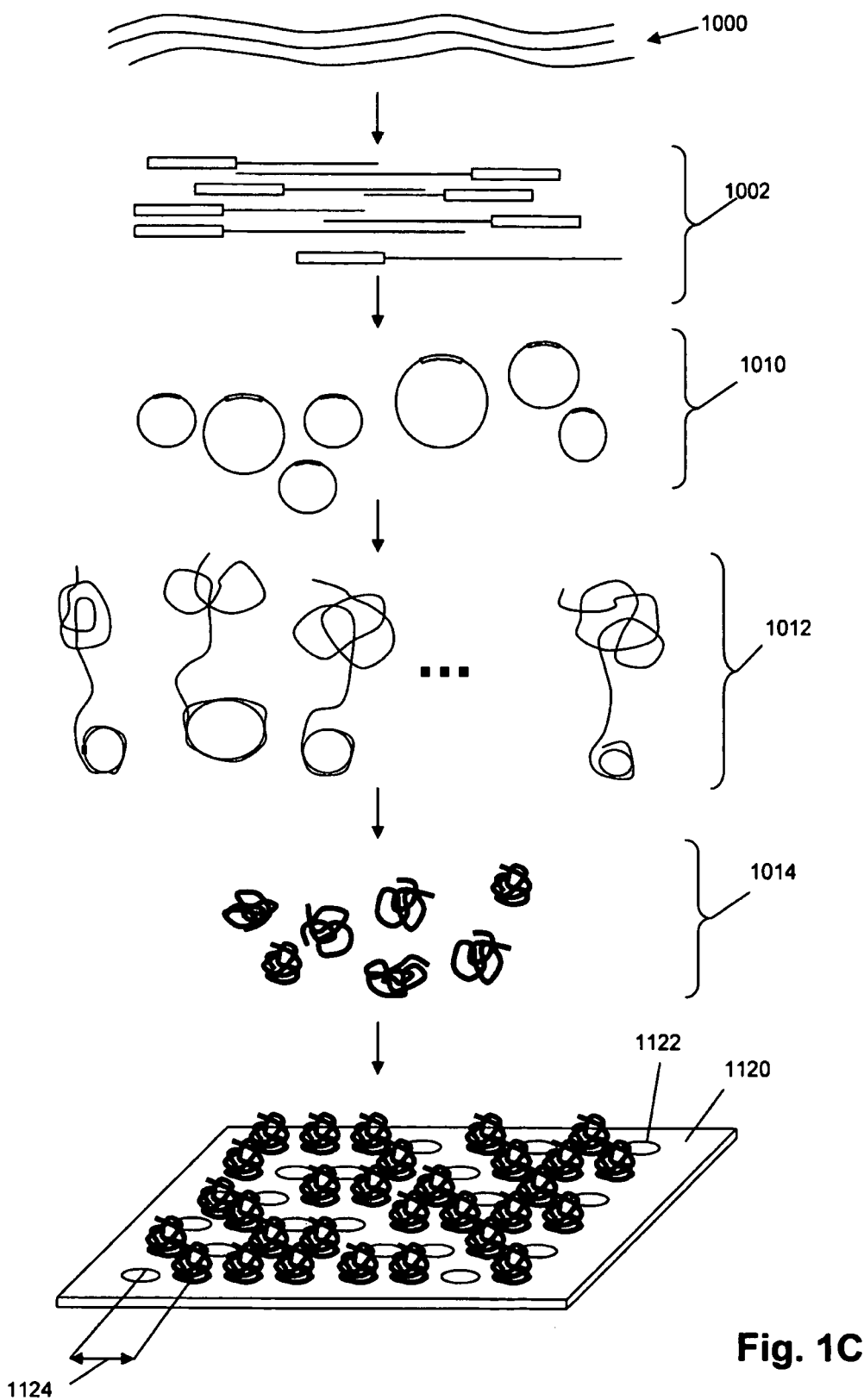

In another aspect of the invention, illustrated for a particular embodiment in FIG. 1C, the requirement of selecting densities of randomly disposed single molecules to ensure desired nearest neighbor distances is obviated by providing on a surface discrete spaced apart regions that are substantially the sole sites for attaching single molecules. That is, in such embodiments the regions on the surface between the discrete spaced apart regions, referred to herein as "inter-regional areas," are inert in the sense that concatemers, or other macromolecular structures, do not bind to such regions. In some embodiments, such inter-regional areas may be treated with blocking agents, e.g. DNAs unrelated to concatemer DNA, other polymers, and the like As in FIG. 1A, source nucleic acids (1000) are fragmented and adaptored (1002) for circularization (1010), after which concatemers are formed by RCR (1012). Isolated concatemers (1014) are then applied to surface (1120) that has a regular array of discrete spaced apart regions (1122) that each have a nearest neighbor distance (1124) that is determined by the design and fabrication of surface (1120). As described more fully below, arrays of discrete spaced apart regions (1122) having micron and sub-micron dimensions for derivatizing with capture oligonucleotides or reactive functionalities can be fabricated using conventional semiconductor fabrication techniques, including electron beam lithography, nano imprint technology, photolithography, and the like. Generally, the area of discrete spaced apart regions (1122) is selected, along with attachment chemistries, macromolecular structures employed, and the like, to correspond to the size of single molecules of the invention so that when single molecules are applied to surface (1120) substantially every region (1122) is occupied by no more than one single molecule. The likelihood of having only one single molecule per discrete spaced apart region may be increased by selecting a density of reactive functionalities or capture oligonucleotides that results in fewer such moieties than their respective complements on single molecules. Thus, a single molecule will "occupy" all linkages to the surface at a particular discrete spaced apart region, thereby reducing the chance that a second single molecule will also bind to the same region. In particular, in one embodiment, substantially all the capture oligonucleotides in a discrete spaced apart region hybridize to adaptor oligonucleotides a single macromolecular structure. In one aspect, a discrete spaced apart region contains a number of reactive functionalities or capture oligonucleotides that is from about ten percent to about fifty percent of the number of complementary functionalities or adaptor oligonucleotides of a single molecule. The length and sequence(s) of capture oligonucleotides may vary widely, and may be selected in accordance with well known principles, e.g. Wetmur, Critical Reviews in Biochemistry and Molecular Biology, 26: 227-259 (1991); Britten and Davidson, chapter 1 in Hames et al, editors, Nucleic Acid Hybridization: A Practical Approach (IRL Press, Oxford, 1985). In one aspect, the lengths of capture oligonucleotides are in a range of from 6 to 30 nucleotides, and in another aspect, within a range of from 8 to 30 nucleotides, or from 10 to 24 nucleotides. Lengths and sequences of capture oligonucleotides are selected (i) to provide effective binding of macromolecular structures to a surface, so that losses of macromolecular structures are minimized during steps of analytical operations, such as washing, etc., and (ii) to avoid interference with analytical operations on analyte molecules, particularly when analyte molecules are DNA fragments in a concatemer. In regard to (i), in one aspect, sequences and lengths are selected to provide duplexes between capture oligonucleotides and their complements that are sufficiently stable so that they do not dissociate in a stringent wash. In regard to (ii), if DNA fragments are from a particular species of organism, then databases, when available, may be used to screen potential capture sequences that may form spurious or undesired hybrids with DNA fragments. Other factors in selecting sequences for capture oligonucleotides are similar to those considered in selecting primers, hybridization probes, oligonucleotide tags, and the like, for which there is ample guidance, as evidenced by the references cited below in the Definitions section. In some embodiments, a discrete spaced apart region may contain more than one kind of capture oligonucleotide, and each different capture oligonucleotide may have a different length and sequence. In one aspect of embodiments employing regular arrays of discrete spaced apart regions, sequences of capture oligonucleotides are selected so that sequences of capture oligonucleotide at nearest neighbor regions have different sequences. In a rectilinear array, such configurations are achieved by rows of alternating sequence types. In other embodiments, a surface may have a plurality of subarrays of discrete spaced apart regions wherein each different subarray has capture oligonucleotides with distinct nucleotide sequences different from those of the other subarrays. A plurality of subarrays may include 2 subarrays, or 4 or fewer subarrays, or 8 or fewer subarrays, or 16 or fewer subarrays, or 32 or fewer subarrays, or 64 of fewer subarrays. In still other embodiments, a surface may include 5000 or fewer subarrays. In one aspect, capture oligonucleotides are attached to the surface of an array by a spacer molecule, e.g. polyethylene glycol, or like inert chain, as is done with microarrays, in order to minimize undesired affects of surface groups or interactions with the capture oligonucleotides or other reagents.

In one aspect, the area of discrete spaced apart regions (1122) is less than 1 $\mu m^2$; and in another aspect, the area of discrete spaced apart regions (1122) is in the range of from 0.04 $\mu m^2$ to 1 $\mu m^2$; and in still another aspect, the area of discrete spaced apart regions (1122) is in the range of from 0.2 $\mu m^2$ to 1 $\mu m^2$. In another aspect, when discrete spaced apart regions are approximately circular or square in shape so that their sizes can be indicated by a single linear dimension, the size of such regions are in the range of from 125 nm to 250 nm, or in the range of from 200 nm to 500 nm. In one aspect, center-to-center distances of nearest neighbors of regions (1122) are in the range of from 0.25 $\mu m$ to 20 $\mu m$; and in another aspect, such distances are in the range of from 1 $\mu m$ to 10 $\mu m$, or in the range from 50 to 1000 nm. In one aspect, regions (1120) may be arranged on surface (1018) in virtually any pattern in which regions (1122) have defined locations, i.e. in any regular array, which makes signal collection and data analysis functions more efficient. Such patterns include, but are not limited to, concentric circles of regions (1122), spiral patterns, rectilinear patterns, hexagonal patterns, and the like. Preferably, regions (1122) are arranged in a rectilinear or hexagonal pattern.

Figure 1D:
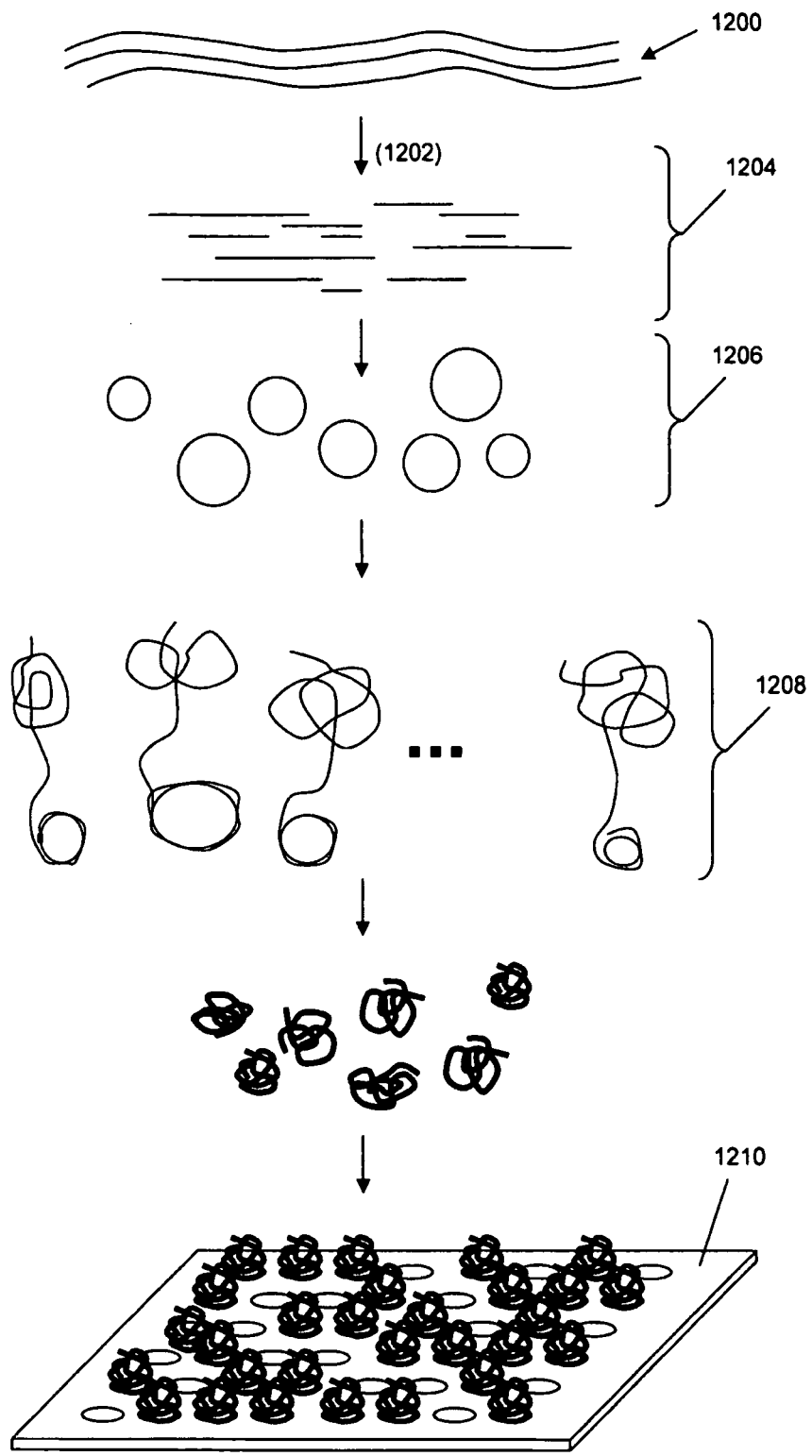

As illustrated in FIG. 1D, in certain embodiments, DNA circles prepared from source nucleic acid (1200) need not include an adaptor oligonucleotide. As before, source nucleic acid (1200) is fragmented and denatured (1202) to form a population of single strand fragments (1204), preferably in the size range of from about 50 to 600 nucleotides, and more preferably in the size range of from about 300 to 600 nucleotides, after which they are circularized in a non-template driven reaction with circularizing ligase, such as CircLigase (Epicentre Biotechnologies, Madison, Wis.), or the like. After formation of DNA circles (1206), concatemers are generated by providing a mixture of primers that bind to selected sequences. The mixture of primers may be selected so that only a subset of the total number of DNA circles (1206) generate concatemers. After concatemers are generated (1208), they are isolated and applied to surface (1210) to form a random array of the invention.

Figure 1E:
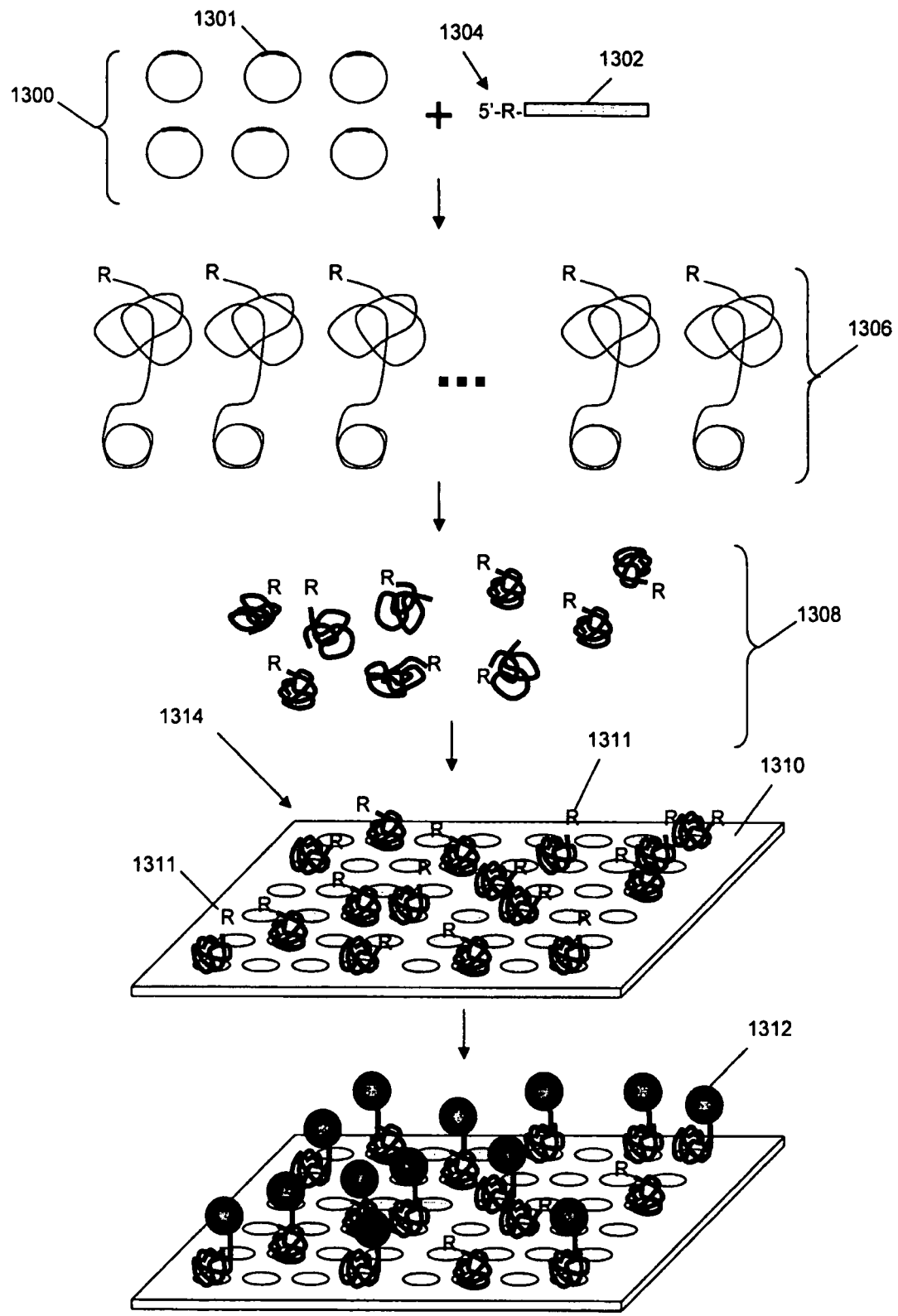

As mentioned above, single molecules of the invention comprise an attachment portion and an analyte portion such that the attachment portion comprises a macromolecular structure that provides multivalent attachment of the single molecule to a surface. As illustrated in FIG. 1E, macromolecular structures may be concatemers made by an RCR reaction in which the DNA circles in the reaction are synthetic. An analyte portion of a single molecule is then attached by way of a unique functionality on the concatemer. Synthetic DNA circles of virtually any sequence can be produced using well-known techniques, conveniently, in sizes up to several hundred nucleotides, e.g. 200, and with more difficulty, in sizes of many hundreds of nucleotides, e.g. up to 500, e.g. Kool, U.S. Pat. No. 5,426,180; Dolinnaya et al (1993), Nucleic Acids Research, 21: 5403-5407; Rubin et al (1995), Nucleic Acids Research, 23: 3547-3553; and the like, which are incorporated herein by reference. Synthetic DNA circles (1300) that comprise primer binding sites (1301) are combined with primer (1302) in an RCR reaction (1306) to produce concatemers (1308). Usually, in this embodiment, all circles have the same sequence, although different sequences can be employed, for example, for directing subsets of concatemers to preselected regions of an array via complementary attachment moieties, such as adaptor sequences and capture oligonucleotides. Primer (1302) is synthesized with a functionality (1304, designated as "R") at its 5' end that is capable of reacting with a complementary functionality on an analyte to form a covalent linkage. Exemplary functionalities include amino groups, sulfhydryl groups, and the like, that can be attached with commercially available chemistries (e.g. Glen Research). Concatemers (1308) are applied to surface (1310) to form an array (1314), after which analytes (1312) having an attachment moiety are applied to array (1310) where a linkage is formed with a concatemer by reaction of unique functionalities, R (1311) and attachment moiety (1312). Alternatively, prior to application to array (1310), concatemers (1308) may be combined with analytes (1312) so that attachment moieties and unique functionalities can react to form a linkage, after which the resulting conjugate is applied to array (1310). There is abundant guidance in the literature in selecting appropriate attachment moieties and unique functionalities for linking concatemers (1308) and many classes of analyte. In one aspect, for linking protein or peptide analytes to concatemers, many homo- and heterobifunctional reagents are available commercially (e.g. Pierce) and are disclosed in references such as Hermanson, Bioconjugate Techniques (Academic Press, New York, 1996), which is incorporated by reference. For example, whenever the unique functionality is an amino group, then concatemers (1308) can be linked to a sulfhydryl group on an analyte using N-succinimidyl 3-(2- pyridyldithio)propionate (SPDP), succinimidyloxycarbonyl-α-methyl-α-(2-pyridyldithio)toluene (SMPT), succinimidyl-4-(N-maleimidomethyl)cyclohexane-1-carboxylate (SMCC), m-maleimidobenzoyl-N-hydroxysuccinimide ester (MBS), N-succinimidyl(4-iodoacetyl)aminobenzoate (SIAB), succinimidyl 6-((iodoacetyl)amino)hexanoate (SIAX), and like reagents. Suitable complementary functionalities on analytes include amino groups, sulfhydryl groups, carbonyl groups, which may occur naturally on analytes or may be added by reaction with a suitable homo- or heterobifunctional reagent. Analyte molecules may also be attached to macromolecular structures by way of non-covalent linkages, such as biotin-streptavidin linkages, the formation of complexes, e.g. a duplexes, between a first oligonucleotide attached to a concatemer and a complementary oligonucleotide attached to, or forming part of, an analyte, or like linkages. Analytes include biomolecules, such as nucleic acids, for example, DNA or RNA fragments, polysaccharides, proteins, and the like.

Figure 1F:
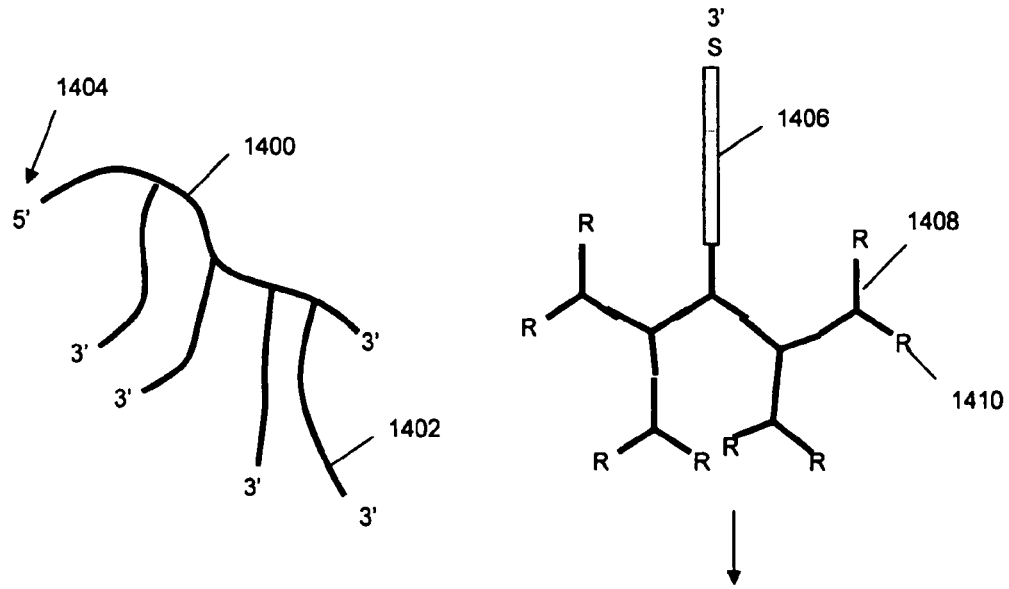
Figure 1G:
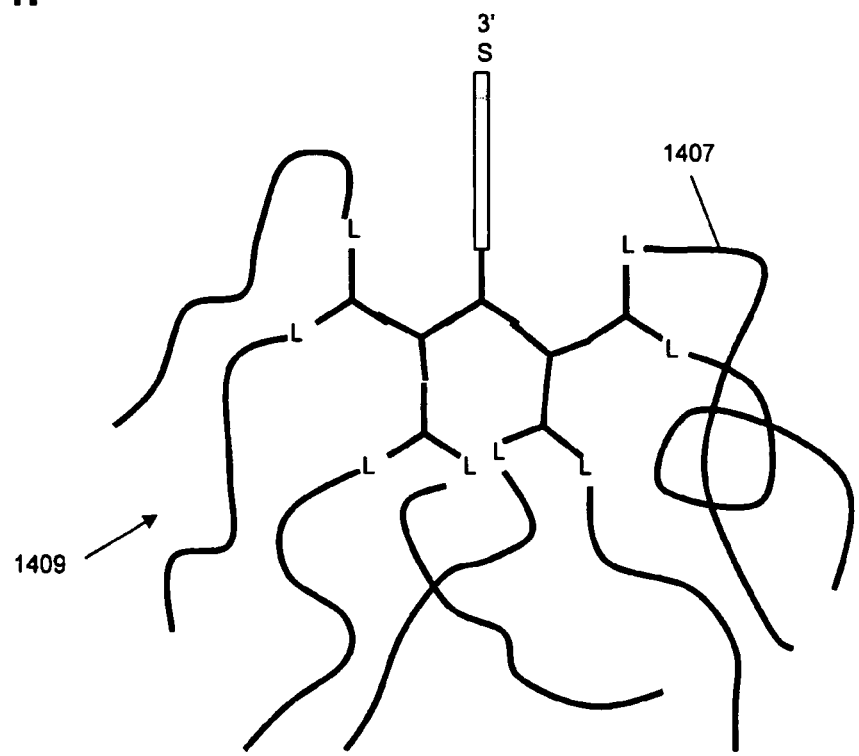
Figure 1H:
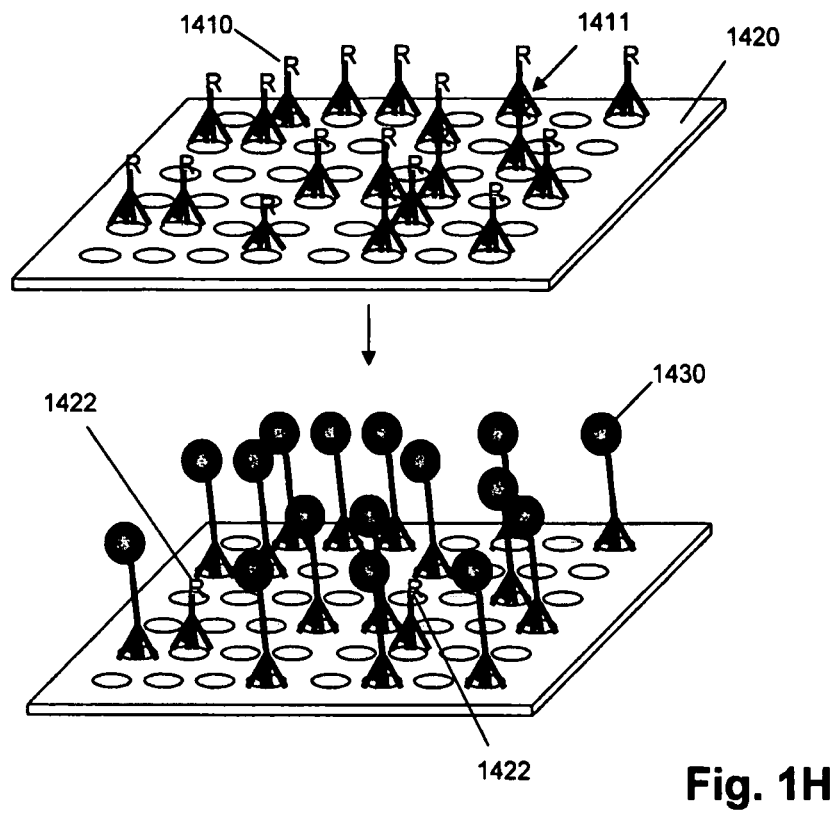
Figure 1I:
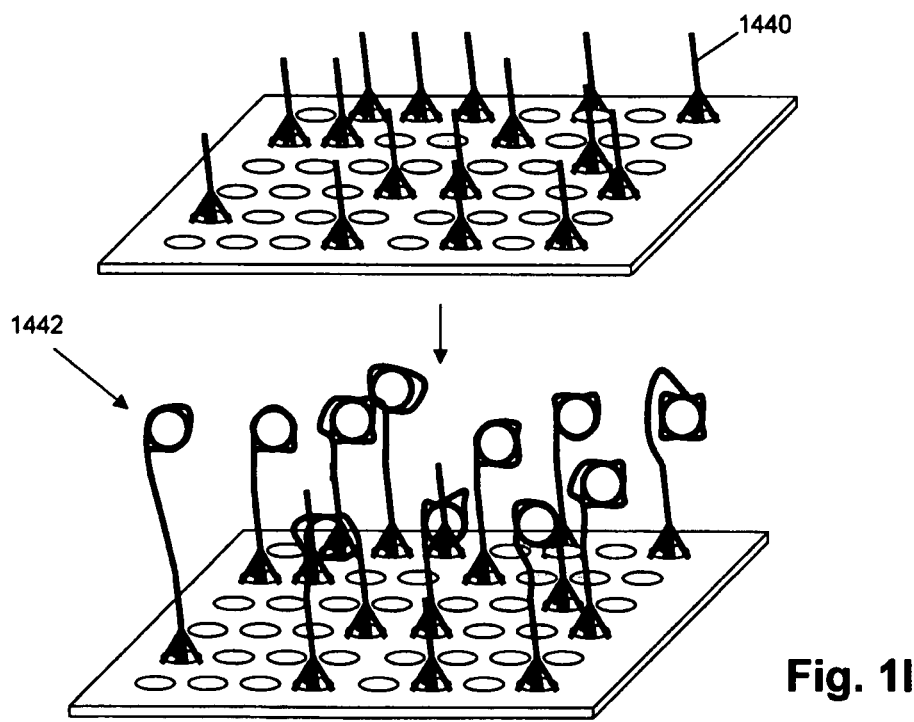

As mentioned above, macromolecular structures of the invention may comprise branched polymers as well as linear polymers, such as concatemers of DNA fragments. Exemplary branched polymer structures are illustrated in FIGS. 1F and 1G. In FIG. 1F, a branched DNA structure is illustrated that comprises a backbone polynucleotide (1400) and multiple branch polynucleotides (1402) each connected to backbone polynucleotide (1400) by their 5' ends to form a comb-like structure that has all 3' ends, except for a single 5' end (1404) on backbone polynucleotide (1400), which is derivatized to have a unique functionality. As mentioned below, such unique functionality may be a reactive chemical group, e.g. a protected or unprotected amine, sulfhydryl, or the like, or it may be an oligonucleotide having a unique sequence for capturing an analyte having an oligonucleotide with a complementary sequence thereto. Likewise, such unique functionality may be a capture moiety, such as biotin, or the like. Such branched DNA structures are synthesized using known techniques, e.g. Gryaznov, U.S. Pat. No. 5,571,677; Urdea et al, U.S. Pat. No. 5,124,246; Seeman et al, U.S. Pat. No. 6,255,469; and the like, which are incorporated herein by reference. Whenever such macromolecular structures are polynucleotides, the sequences of components thereof may be selected for facile self-assembly, or they may be linked by way of specialized linking chemistries, e.g. as disclosed below, in which case sequences are selected based on other factors, including, in some embodiments, avoidance of self-annealing, facile binding to capture oligonucleotides on a surface, and the like. In FIG. 1G, a dentrimeric structure is illustrated that comprises oligonucleotide (1406), which is derivatized with multiple tri-valent linking groups (1408) that each have two functionalities (1410, designated by "R") by which additional polymers (1407), e.g. polynucleotides, can be attached to form a linkage to oligonucleotide (1406) thereby forming macromolecular structure (1409), which, in turn, if likewise derivatized with multivalent linkers, can form a nucleic acid dendrimer. Trivalent linkers (1408) for use with oligonucleotides are disclosed in Iyer et al, U.S. Pat. No. 5,916,750, which is incorporated herein by reference. As illustrated in FIG. 1H, once such dendrimeric or branched structures (1411) are constructed, they can be attached to array (1420) as described above for linear polynucleotides, after which analytes (1430) can be attached via unique functionalities (1410). Optionally, unreacted unique functionalities (1422) may be capped using conventional techniques. Alternatively, dendrimeric or branched structures (1411) may be combined with analytes (1430) first, e.g. in solution, so that conjugates are formed, and then the conjugates are disposed on array (1420). When the analyte is a polynucleotide (1440) with a free 3' end, as shown in FIG. 1I, such end may be extended in an in situ RCR reaction to form either concatemers of target sequences or other sequences for further additions. Likewise, polynucleotide analytes may be extended by ligation using conventional techniques.

Source Nucleic Acids and Circularization of Target Sequences

In one aspect of the invention, macromolecular structures comprise concatemers of polynucleotide analytes, i.e. target sequences, which are extracted or derived from a sample, such as genomic DNA or cDNAs from a patient, an organism of economic interest, or the like. Random arrays of the invention comprising such single molecules are useful in providing genome-wide analyses, including sequence determination, SNP measurement, allele quantitation, copy number measurements, and the like. For mammalian-sized genomes, preferably fragmentation is carried out in at least two stages, a first stage to generate a population of fragments in a size range of from about 100 kilobases (Kb) to about 250 kilobases, and a second stage, applied separately to each 100-250 Kb fragment, to generate fragments in the size range of from about 50 to 600 nucleotides, and more preferably in the range of from about 300 to 600 nucleotides, for generating concatemers for a random array. In some aspects of the invention, the first stage of fragmentation may also be employed to select a predetermined subset of such fragments, e.g. fragments containing genes that encode proteins of a signal transduction pathway, or the like. The amount of genomic DNA required for constructing arrays of the invention can vary widely. In one aspect, for mammalian-sized genomes, fragments are generated from at least 10 genome-equivalents of DNA; and in another aspect, fragments are generated from at least 30 genome-equivalents of DNA; and in another aspect, fragments are generated from at least 60 genome-equivalents of DNA.

Genomic DNA is obtained using conventional techniques, for example, as disclosed in Sambrook et al., supra, 1999; Current Protocols in Molecular Biology, Ausubel et al., eds. (John Wiley and Sons, Inc., NY, 1999), or the like, Important factors for isolating genomic DNA include the following: 1) the DNA is free of DNA processing enzymes and contaminating salts; 2) the entire genome is equally represented; and 3) the DNA fragments are between about 5,000 and 100,000 bp in length. In many cases, no digestion of the extracted DNA is required because shear forces created during lysis and extraction will generate fragments in the desired range. In another embodiment, shorter fragments (1-5 kb) can be generated by enzymatic fragmentation using restriction endonucleases. In one embodiment, 10-100 genome-equivalents of DNA ensure that the population of fragments covers the entire genome. In some cases, it is advantageous to provide carrier DNA, e.g. unrelated circular synthetic double-stranded DNA, to be mixed and used with the sample DNA whenever only small amounts of sample DNA are available and there is danger of losses through nonspecific binding, e.g. to container walls and the like.

In generating fragments in either stage, fragments may be derived from either an entire genome or it may be derived from a selected subset of a genome. Many techniques are available for isolating or enriching fragments from a subset of a genome, as exemplified by the following references that are incorporated by reference: Kandpal et al (1990), Nucleic Acids Research, 18: 1789-1795; Callow et al, U.S. patent publication 2005/0019776; Zabeau et al, U.S. Pat. No. 6,045, 994; Deugau et al, U.S. Pat. No. 5,508,169; Sibson, U.S. Pat. No. 5,728,524; Guilfoyle et al, U.S. Pat. No. 5,994,068; Jones et al, U.S. patent publication 2005/0142577; Gullberg et al, U.S. patent publication 2005/0037356; Matsuzaki et al, U.S. patent publication 2004/0067493; and the like.

Figure 2B:
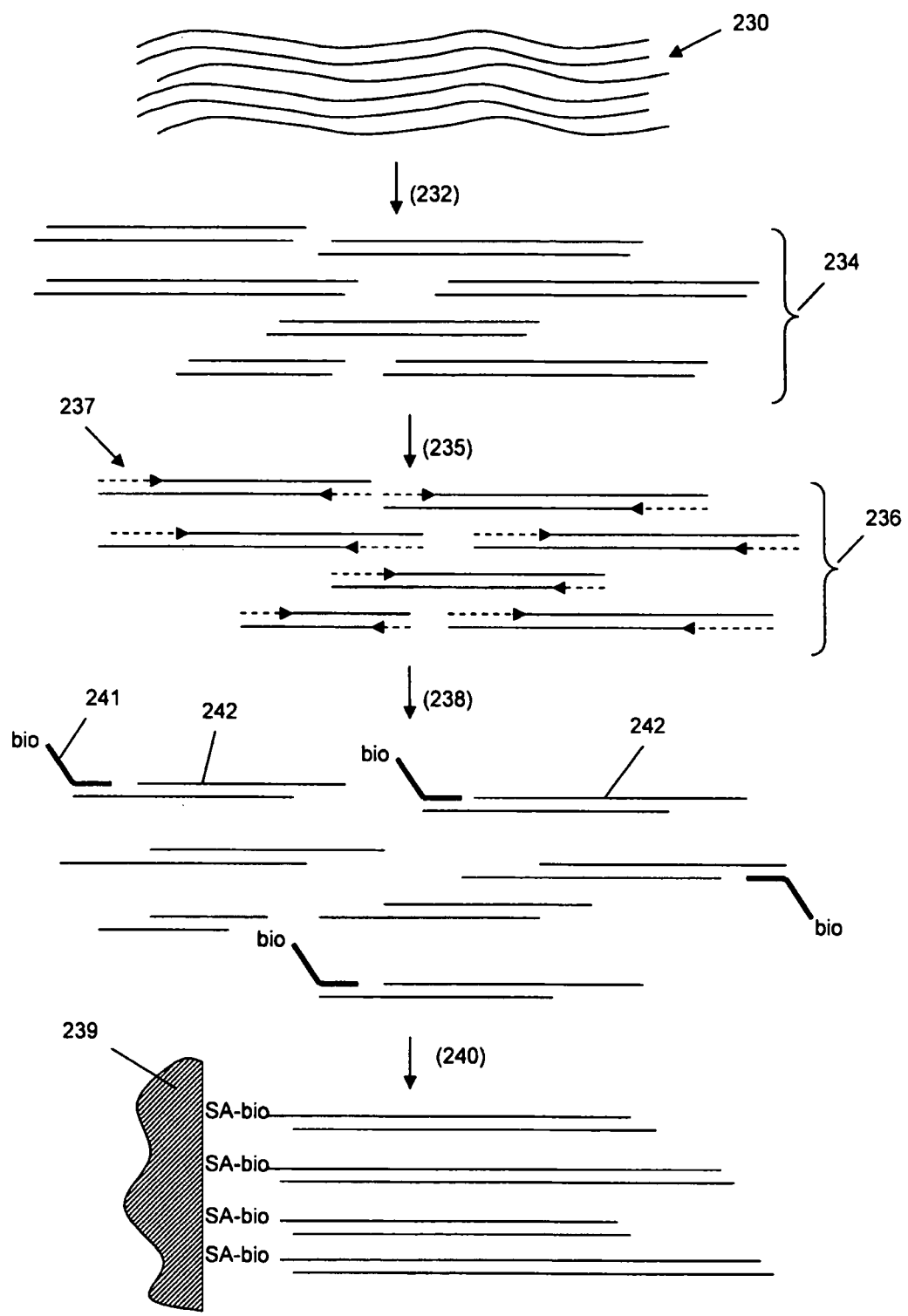

For mammalian-sized genomes, an initial fragmentation of genomic DNA can be achieved by digestion with one or more "rare" cutting restriction endonucleases, such as Not I, Asc I, Bae I, CspC I, Pac I, Fse I, Sap I, Sfi I, Psr I, or the like. The resulting fragments can be used directly, or for genomes that have been sequenced, specific fragments may be isolated from such digested DNA for subsequent processing as illustrated in FIG. 2B. Genomic DNA (230) is digested (232) with a rare cutting restriction endonuclease to generate fragments (234), after which the fragments (234) are further digested for a short period (i.e. the reaction is not allowed to run to completion) with a 5' single stranded exonuclease, such as λ exonuclease, to expose sequences (237) adjacent to restriction site sequences at the end of the fragments. Such exposed sequences will be unique for each fragment. Accordingly, biotinylated primers (241) specific for the ends of desired fragments can be annealed to a capture oligonucleotide for isolation; or alternatively, such fragments can be annealed to a primer having a capture moiety, such as biotin, and extended with a DNA polymerase that does not have strand displacement activity, such as Taq polymerase Stoffel fragment. After such extension, the 3' end of primers (241) abut the top strand of fragments (242) such that they can be ligated to form a continuous strand. The latter approach may also be implemented with a DNA polymerase that does have strand displacement activity and replaces the top strand (242) by synthesis. In either approach, the biotinylated fragments may then be isolated (240) using a solid support (239) derivatized with streptavidin.

In another aspect, primer extension from a genomic DNA template is used to generate a linear amplification of selected sequences greater than 10 kilobases surrounding genomic regions of interest. For example, to create a population of defined-sized targets, 20 cycles of linear amplification is performed with a forward primer followed by 20 cycles with a reverse primer. Before applying the second primer, the first primer is removed with a standard column for long DNA purification or degraded if a few uracil bases are incorporated. A greater number of reverse strands are generated relative to forward strands resulting in a population of double stranded molecules and single stranded reverse strands. The reverse primer may be biotinylated for capture to streptavidin beads which can be heated to melt any double stranded homoduplexes from being captured. All attached molecules will be single stranded and representing one strand of the original genomic DNA.

The products produced can be fragmented to 0.2-2 kb in size, or more preferably, 0.3-0.6 kb in size (effectively releasing them from the solid support) and circularized for an RCR reaction. In one method of circularization, illustrated in FIG. 2A, after genomic DNA (200) is fragmented and denatured (202), single stranded DNA fragments (204) are first treated with a terminal transferase (206) to attach a poly dA tails (208) to 3-prime ends. This is then followed by ligation (212) of the free ends intra-molecularly with the aid of bridging oligonucleotide (210). that is complementary to the poly dA tail at one end and complementary to any sequence at the other end by virtue of a segment of degenerate nucleotides. Duplex region (214) of bridging oligonucleotide (210) contains at least a primer binding site for RCR and, in some embodiments, sequences that provide complements to a capture oligonucleotide, which may be the same or different from the primer binding site sequence, or which may overlap the primer binding site sequence. The length of capture oligonucleotides may vary widely, In one aspect, capture oligonucleotides and their complements in a bridging oligonucleotide have lengths in the range of from 10 to 100 nucleotides; and more preferably, in the range of from 10 to 40 nucleotides. In some embodiments, duplex region (214) may contain additional elements, such as an oligonucleotide tag, for example, for identifying the source nucleic acid from which its associated DNA fragment came. That is, in some embodiments, circles or adaptor ligation or concatemers from different source nucleic acids may be prepared separately during which a bridging adaptor containing a unique tag is used, after which they are mixed for concatemer preparation or application to a surface to produce a random array. The associated fragments may be identified on such a random array by hybridizing a labeled tag complement to its corresponding tag sequences in the concatemers, or by sequencing the entire adaptor or the tag region of the adaptor. Circular products (218) may be conveniently isolated by a conventional purification column, digestion of non-circular DNA by one or more appropriate exonucleases, or both.

As mentioned above, DNA fragments of the desired sized range, e.g. 50-600 nucleotides, can also be circularized using circularizing enzymes, such as CircLigase, as single stranded DNA ligase that circularizes single stranded DNA without the need of a template. CircLigase is used in accordance with the manufacturer's instructions (Epicentre, Madison, Wis.). A preferred protocol for forming single stranded DNA circles comprising a DNA fragment and one or more adapters is to use standard ligase such as T4 ligase for ligation an adapter to one end of DNA fragment and than to use CircLigase to close the circle, as described more fully below.

An exemplary protocol for generating a DNA circle comprising an adaptor oligonucleotide and a target sequence using T4 ligase. The target sequence is a synthetic oligo T1N (sequence: 5'-NNNNNNNNGCATANCACGANGTCAT-NATCGTNCAAACGTCAGTCCANGAATCNAGAT CCACTTAGANTGNCGNNNNNNNN-3') (SEQ ID NO: 1). The adaptor is made up of 2 separate oligos. The adaptor oligo that joins to the 5' end of T1N is BR2-ad (sequence: 5'-TAT-CATCTGGATGTTAGGAAGACAAAAG-GAAGCTGAGGACATTAACGGAC-3') (SEQ ID NO: 2) and the adaptor oligo that joins to the 3' end of T1N is UR3-ext (sequence: 5'-ACCTTCAGACCAGAT-3') (SEQ ID NO: 3) UR3-ext contains a type IIs restriction enzyme site (Acu I: CTTCAG) to provide a way to linearize the DNA circular for insertion of a second adaptor. BR2-ad is annealed to BR2-temp (sequence 5'-NNNNNNNGTCCGTTAATGTCCT-CAG-3') (SEQ ID NO: 4) to form a double-stranded adaptor BR2 adaptor. UR3-ext is annealed to biotinylated UR3-temp (sequence 5'-[BIOTIN]ATCTGGTCTGAAGGTNNNN-3') (SEQ ID NO: 5) to form a double-stranded adaptor UR3 adaptor. 1 pmol of target T1N is ligated to 25 pmol of BR2 adaptor and 10 pmol of UR3 adaptor in a single ligation reaction containing 50 mM Tris-Cl, pH7.8, 10% PEG, 1 mM ATP, 50 mg/L BSA, 10 mM MgCl$_2$, 0.3 unit/μl T4 DNA ligase (Epicentre Biotechnologies, WI) and 10 mM DTT) in a final volume of 10 ul. The ligation reaction is incubated in a temperature cycling program of 15° C. for 11 min, 37° C. for 1 min repeated 18 times. The reaction is terminated by heating at 70° C. for 10 min. Excess BR2 adaptors are removed by capturing the ligated products with streptavidin magnetic beads (New England Biolabs, MA). 3.3 ul of 4× binding buffer (2M NaCl, 80 mM Tris HCl pH7.5) is added to the ligation reaction which is then combined with 15 μg of streptavidin magnetic beads in 1× binding buffer (0.5M NaCl, 20 mM Tris HCl pH7.5). After 15 min incubation in room temperature, the beads are washed twice with 4 volumes of low salt buffer (0.15M NaCl, 20 mM Tris HCl pH7.5). Elution buffer (10 mM Tris HCl pH7.5) is pre-warmed to 70 deg, 10 μl of which is added to the beads at 70° C. for 5 min. After magnetic separation, the supernatant is retained as primary purified sample. This sample is further purified by removing the excess UR3 adaptors with magnetic beads pre-bound with a biotinylated oligo BR-rc-bio (sequence: 5'-[BIOTIN] CTTTTGTCTTCCTAACATCC-3') (SEQ ID NO: 6) that is reverse complementary to BR2-ad similarly as described above. The concentration of the adaptor-target ligated product in the final purified sample is estimated by urea polyacrylamide gel electrophoresis analysis. The circularization is carried out by phosphorylating the ligation products using 0.2 unit/μl T4 polynucleotide kinase (Epicentre Biotechnologies) in 1 mM ATP and standard buffer provided by the supplier, and circularized with ten-fold molar excess of a splint oligo UR3-closing-88 (sequence 5'-AGATGATAATCTGGTC-3') (SEQ ID NO: 7) using 0.3 unit/μl of T4 DNA ligase (Epicentre Biotechnologies) and 1 mM ATP. The circularized product is validated by performing RCR reactions as described below.

Generating Polynucleotide Concatemers by Rolling Circle Replication

In one aspect of the invention, single molecules comprise concatemers of polynucleotides, usually polynucleotide analytes, i.e. target sequences, that have been produce in a conventional rolling circle replication (RCR) reaction. Guidance for selecting conditions and reagents for RCR reactions is available in many references available to those of ordinary skill, as evidence by the following that are incorporated by reference: Kool, U.S. Pat. No. 5,426,180; Lizardi, U.S. Pat. Nos. 5,854,033 and 6,143,495; Landegren, U.S. Pat. No. 5,871,921; and the like. Generally, RCR reaction components comprise single stranded DNA circles, one or more primers that anneal to DNA circles, a DNA polymerase having strand displacement activity to extend the 3' ends of primers annealed to DNA circles, nucleoside triphosphates, and a conventional polymerase reaction buffer. Such components are combined under conditions that permit primers to anneal to DNA circles and be extended by the DNA polymerase to form concatemers of DNA circle complements. An exemplary RCR reaction protocol is as follows: In a 50 μL reaction mixture, the following ingredients are assembled: 2-50 pmol circular DNA, 0.5 units/μL phage φ29 DNA polymerase, 0.2 μg/μL BSA, 3 mM dNTP, 1× φ29 DNA polymerase reaction buffer (Amersham). The RCR reaction is carried out at 30° C. for 12 hours. In some embodiments, the concentration of circular DNA in the polymerase reaction may be selected to be low (approximately 10-100 billion circles per ml, or 10-100 circles per picoliter) to avoid entanglement and other intermolecular interactions.

Preferably, concatemers produced by RCR are approximately uniform in size; accordingly, in some embodiments, methods of making arrays of the invention may include a step of size-selecting concatemers. For example, in one aspect, concatemers are selected that as a population have a coefficient of variation in molecular weight of less than about 30%; and in another embodiment, less than about 20%. In one aspect, size uniformity is further improved by adding low concentrations of chain terminators, such ddNTPs, to the RCR reaction mixture to reduce the presence of very large concatemers, e.g. produced by DNA circles that are synthesized at a higher rate by polymerases. In one embodiment, concentrations of ddNTPs are used that result in an expected concatemer size in the range of from 50-250 Kb, or in the range of from 50-100 Kb. In another aspect, concatemers may be enriched for a particular size range using a conventional separation techniques, e.g. size-exclusion chromatography, membrane filtration, or the like.

Generation of Macromolecular Structures Comprising Branched Polymers and DNA Assemblies In one aspect of the invention, macromolecular structures comprise polymers having at least one unique functionality, which for polynucleotides is usually a functionality at a 5' or 3' end, and a plurality of complementary functionalities that are capable of specifically reacting with reactive functionalities of the surface of a solid support. Macromolecular structures comprising branched polymers, especially branched polynucleotides, may be synthesized in a variety of ways, as disclosed by Gryaznov (cited above), Urdea (cited above), and like references. In one aspect, branched polymers of the invention include comb-type branched polymers, which comprise a linear polymeric unit with one or more branch points located at interior monomers and/or linkage moieties. Branched polymers of the invention also include fork-type branched polymers, which comprise a linear polymeric unit with one or two branch points located at terminal monomers and/or linkage moieties. Macromolecular structures of the invention also include assemblies of linear and/or branched polynucleotides bound together by one or more duplexes or triplexes. Such assemblies may be self-assembled from component linear polynucleotide, e.g. as disclosed by Goodman et al, Science, 310: 1661-1665 (2005); Birac et al, J. Mol. Graph Model, (Apr. 18, 2006); Seeman et al, U.S. Pat. No. 6,255,469; and the like, which are incorporated herein by reference. In one aspect, linear polymeric units of the invention have the form: "-(M-L)$_n$-" wherein L is a linker moiety and M is a monomer that may be selected from a wide range of chemical structures to provide a range of functions from serving as an inert non-sterically hindering spacer moiety to providing a reactive functionality which can serve as a branching point to attach other components, a site for attaching labels; a site for attaching oligonucleotides or other binding polymers for hybridizing or binding to amplifier strands or structures, e.g. as described by Urdea et al, U.S. Pat. No. 5,124,246 or Wang et al, U.S. Pat. No. 4,925,785; a site for attaching "hooks", e.g. as described in Whiteley et al, U.S. Pat. No. 4,883,750; or as a site for attaching other groups for affecting solubility, promotion of duplex and/or triplex formation, such as intercalators, alkylating agents, and the like. The following references disclose several phosphoramidite and/or hydrogen phosphonate monomers suitable for use in the present invention and provide guidance for their synthesis and inclusion into oligonucleotides: Newton et al, Nucleic Acids Research, 21:1155-1162 (1993); Griffin et al, J. Am. Chem. Soc., 114:7976-7982 (1992); Jaschke et al, Tetrahedron Letters, 34:301-304 (1992); Ma et al, International application PCT/CA92/00423; Zon et al, International application PCT/US90/06630; Durand et al, Nucleic Acids Research, 18:6353-6359 (1990); Salunkhe et al, J. Am. Chem. Soc., 114:8768-8772 (1992); Urdea et al, U.S. Pat. No. 5,093,232; Ruth, U.S. Pat. No. 4,948,882; Cruickshank, U.S. Pat. No. 5,091,519; Haralambidis et al, Nucleic Acids Research, 15:4857-4876 (1987); and the like. More particularly, M is a straight chain, cyclic, or branched organic molecular structure containing from 1 to 20 carbon atoms and from 0 to 10 heteroatoms selected from the group consisting of oxygen, nitrogen, and sulfur. Preferably, M is alkyl, alkoxy, alkenyl, or aryl containing from 1 to 16 carbon atoms; heterocyclic having from 3 to 8 carbon atoms and from 1 to 3 heteroatoms selected from the group consisting of oxygen, nitrogen, and sulfur; glycosyl; or nucleosidyl. More preferably, M is alkyl, alkoxy, alkenyl, or aryl containing from 1 to 8 carbon atoms; glycosyl; or nucleosidyl. Preferably, L is a phosphorus(V) linking group which may be phosphodiester, phosphotriester, methyl or ethyl phosphonate, phosphorothioate, phosphorodithioate, phosphoramidate, or the like. Generally, linkages derived from phosphoramidite or hydrogen phosphonate precursors are preferred so that the linear polymeric units of the invention can be conveniently synthesized with commercial automated DNA synthesizers, e.g. Applied Biosystems, Inc. (Foster City, Calif.) model 394, or the like. n may vary significantly depending on the nature of M and L. Usually, n varies from about 3 to about 100. When M is a nucleoside or analog thereof or a nucleoside-sized monomer and L is a phosphorus(V) linkage, then n varies from about 12 to about 100. Preferably, when M is a nucleoside or analog thereof or a nucleoside-sized monomer and L is a phosphorus(V) linkage, then n varies from about 12 to about 40. Polymeric units are assembled by forming one or more covalent bridges among them. In one aspect, bridges are formed by reacting thiol, phosphorothioate, or phosphorodithioate groups on one or more components with haloacyl- or haloalkylamimo groups on one or more other components to form one or more thio- or dithiophosphorylacyl or thio- or dithiophosphorylalkyl bridges. Generally, such bridges have one of the following forms: —NHRSP(=Z)(O$^-$)—$^-$OR—NHRS—, wherein R is alkyl or acyl and Z is sulfur or oxygen. The assembly reaction may involve from 2 to 20 components depending on the particular embodiment; but preferably, it involves from 2 to 8 components; and more preferably, it involves from 2 to 4 components. Preferably, the haloacyl or haloalkylamino groups are haloacetylamino groups; and more preferably, the haloacetylamino groups are bromoacetylamino groups. The acyl or alkyl moieties of the haloacyl- or haloalkylamino groups contain from 1 to 12 carbon atoms; and more preferably, such moieties contain from 1 to 8 carbon atoms. The reaction may take place in a wide range of solvent systems; but generally, the assembly reaction takes place under liquid aqueous conditions or in a frozen state in ice, e.g. obtained by lowering the temperature of a liquid aqueous reaction mixture. Alternatively, formation of thiophosphorylacetylamino bridges in DMSO/H2O has been reported by Thuong et al, Tetrahedron Letters, 28:4157-4160 (1987); and Francois et al, Proc. Natl. Acad. Sci., 86:9702-9706 (1989). Typical aqueous conditions include 4 µM of reactants in 25 mM NaCl and 15 mM phosphate buffer (pH 7.0). The thio- or dithiophosphorylacyl- or thio- or dithiophosphorylalkylamino bridges are preferred because they can be readily and selectively cleaved by oxidizing agents, such as silver nitrate, potassium iodide, and the like. Preferably, the bridges are cleaved with potassium iodide, $KI_3$, at a concentration equivalent to about a hundred molar excess of the bridges. Usually, a $KI_3$ is employed at a concentration of about 0.1M. The facile cleavage of these bridges is a great advantage in synthesis of complex macromolecular structures, as it provides a convenient method for analyzing final products and for confirming that the structure of the final product is correct. A 3'-haloacyl- or haloalkylamino (in this example, haloacetylamino) derivatized oligonucleotide 1 is reacted with a 5'-phosphorothioate derivatized oligonucleotide 2 according to the following scheme:

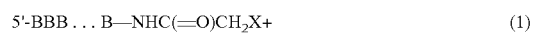  (1)

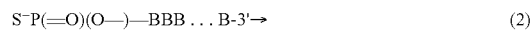  (2)

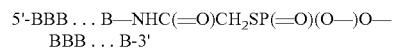

wherein X is halo and B is a nucleotide. It is understood that the nucleotides are merely exemplary of the more general polymeric units, (M-L)$_n$, described above. Compound 1 can be prepared by reacting N-succinimidyl haloacetate in N,N-dimethylformamide (DMF) with a 3'-aminodeoxyribonucleotide precursor in a sodium borate buffer at room temperature. After about 35 minutes the mixture is diluted (e.g. with H$_2$O), desalted and, purified, e.g. by reverse phase HPLC. The Y-aminodeoxyribonucleotide precursor can be prepared as described in Gryaznov and Letsinger, Nucleic Acids Research, 20:3403-3409 (1992). Briefly, after deprotection, the 5' hydroxyl of a deoxythymidine linked to a support via a standard succinyl linkage is phosphitylated by reaction with chloro-(diisopropylethylamino)-methoxyphosphine in an appropriate solvent, such as dichloromethane/diisopropylethylamine. After activation with tetrazole, the 5'-phosphitylated thymidine is reacted with a 5'-trityl-O-3'-amino-3'-deoxynucleoside to form a nucleoside-thymidine dimer wherein the nucleoside moieties are covalently joined by a phosphoramidate linkage. The remainder of the oligonucleotide is synthesized by standard phosphoramidite chemistry. After cleaving the succinyl linkage, the oligonucleotide with a 3' terminal amino group is generated by cleaving the phosphoramidate link by acid treatment, e.g. 80% aqueous acetic acid for 18-20 hours at room temperature. 5'-monophosphorothioate oligonucleotide 2 is formed as follows: A 5' monophosphate is attached to the 5' end of an oligonucleotide either chemically or enzymatically with a kinase, e.g. Sambrook et al, Molecular Cloning: A Laboratory Manual, 2nd Edition (Cold Spring Harbor Laboratory, New York, 1989). Preferably, as a final step in oligonucleotide synthesis, a monophosphate is added by chemical phosphorylation as described by Thuong and Asscline, Chapter 12 in, Eckstein, editor, Oligonucleotides and Analogues (IRL Press, Oxford, 1991) or by Horn and Urdea, Tetrahedron Lett., 27:4705 (1986) (e.g. using commercially available reagents such as 5' Phosphate-ON™ from Clontech Laboratories (Palo Alto, Calif.)). The 5'-monophosphate is then sulfurized using conventional sulfurizing agents, e.g. treatment with a 5% solution of $S_8$ in pyridine/$CS_2$ (1:1, v/v, 45 minutes at room temperature); or treatment with sulfurizing agent described in U.S. Pat. Nos. 5,003,097; 5,151,510; or 5,166,387. Monophosphorodithioates are prepared by analogous procedures, e.g. Froehler et al, European patent publication 0 360 609 A2; Caruthers et al, International application PCT/US89/02293; and the like. Likewise to the above, a 5'-haloacetylamino derivatized oligonucleotide 3 is reacted with a 3'-monophosphorothioate oligonucleotide 4 according to the following scheme:

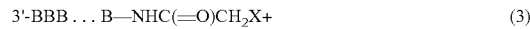  (3)

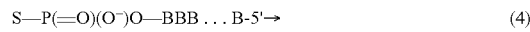  (4)

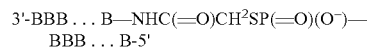

wherein the symbols are defined the same as above, except that the nucleotides monomers of the j- and k-mers are in opposite orientations. In this case, Compound 3 can be prepared by reacting N-succinimidyl halo acetate in N,N-dimethylformamide (DMF) with a 5'-aminodeoxyribonucleotide precursor in a sodium borate buffer at room temperature, as described above for the 3'-amino oligonucleotide. 5'-aminodeoxynucleosides are prepared in accordance with Glinski et al, J. Chem. Soc. Chem. Comm., 915-916 (1970); Miller et al, J. Org. Chem. 29:1772 (1964); Ozols et al, Synthesis, 7:557-559 (1980); and Azhayev et al, Nucleic Acids Research, 6:625-643 (1979); which are incorporated by reference. The 3'-monophosphorothioate oligonucleotide 4 can be prepared as described by Thuong and Asscline (cited above). Oligonucleotides 1 and 4 and 2 and 3 may be reacted to form polymeric units having either two 5' termini or two 3' termini, respectively. Reactive functionalities for the attachment of branches may be introduced at a variety of sites. Preferably, amino functionalities are introduce on a polymeric unit or loop at selected monomers or linking moieties which are then converted to haloacetylamino groups as described above. Amino-derivatized bases of nucleoside monomers may be introduced as taught by Urdea et al, U.S. Pat. No. 5,093,232; Ruth U.S. Pat. No. 4,948,882; Haralambidis et al, Nucleic Acids Research, 15:4857-4876 (1987); or the like. Amino functionalities may also be introduced by a protected hydroxyamine phosphoramidite commercially available from Clontech Laboratories (Palo Alto, Calif.) as Aminomodifier II™. Preferably, amino functionalities are introduced by generating a derivatized phosphoramidate linkage by oxidation of a phosphite linkage with 12 and an alkyldiamine, e.g. as taught by Agrawal et al, Nucleic Acids Research, 18:5419-5423 (1990); and Jager et al, Biochemistry, 27:7237-7246 (1988). Generally, for the above procedures, it is preferable that the haloacyl- or haloalkylamino derivatized polymeric units be prepared separately from the phosphorothioate derivatized polymeric units, otherwise the phosphorothioate moieties require protective groups.

Solid Phase Surfaces for Constructing Random Arrays

A wide variety of supports may be used with the invention. In one aspect, supports are rigid solids that have a surface, preferably a substantially planar surface so that single molecules to be interrogated are in the same plane. The latter feature permits efficient signal collection by detection optics, for example. In another aspect, solid supports of the invention are nonporous, particularly when random arrays of single molecules are analyzed by hybridization reactions requiring small volumes. Suitable solid support materials include materials such as glass, polyacrylamide-coated glass, ceramics, silica, silicon, quartz, various plastics, and the like. In one aspect, the area of a planar surface may be in the range of from 0.5 to 4 cm². In one aspect, the solid support is glass or quartz, such as a microscope slide, having a surface that is uniformly silanized. This may be accomplished using conventional protocols, e.g. acid treatment followed by immersion in a solution of 3-glycidoxypropyl trimethoxysilane, N,N-diisopropylethylamine, and anhydrous xylene (8:1:24 v/v) at 80° C., which forms an epoxysilanized surface. e.g. Beattie et a (1995), Molecular Biotechnology, 4: 213. Such a surface is readily treated to permit end-attachment of capture oligonucleotides, e.g. by providing capture oligonucleotides with a 3' or 5' triethylene glycol phosphoryl spacer (see Beattie et al, cited above) prior to application to the surface. Many other protocols may be used for adding reactive functionalities to glass and other surfaces, as evidenced by the disclosure in Beaucage (cited above).

Whenever enzymatic processing is not required, capture oligonucleotides may comprise non-natural nucleosidic units and/or linkages that confer favorable properties, such as increased duplex stability; such compounds include, but not limited to, peptide nucleic acids (PNAs), locked nucleic acids (LNA), oligonucleotide N3'→P5' phosphoramidates, oligo-2'-O-alkylribonucleotides, and the like.

In embodiments of the invention in which patterns of discrete spaced apart regions are required, photolithography, electron beam lithography, nano imprint lithography, and nano printing may be used to generate such patterns on a wide variety of surfaces, e.g. Pirrung et al, U.S. Pat. No. 5,143,854; Fodor et al, U.S. Pat. No. 5,774,305; Guo, (2004) Journal of Physics D: Applied Physics, 37: R123-141; which are incorporated herein by reference.

In one aspect, surfaces containing a plurality of discrete spaced apart regions are fabricated by photolithography. A commercially available, optically flat, quartz substrate is spin coated with a 100-500 nm thick layer of photo-resist. The photo-resist is then baked on to the quartz substrate. An image of a reticle with a pattern of regions to be activated is projected onto the surface of the photo-resist, using a stepper. After exposure, the photo-resist is developed, removing the areas of the projected pattern which were exposed to the UV source. This is accomplished by plasma etching, a dry developing technique capable of producing very fine detail. The substrate is then baked to strengthen the remaining photo-resist. After baking, the quartz wafer is ready for functionalization. The wafer is then subjected to vapor-deposition of 3-aminopropyldimethylethoxysilane. The density of the amino functionalized monomer can be tightly controlled by varying the concentration of the monomer and the time of exposure of the substrate. Only areas of quartz exposed by the plasma etching process may react with and capture the monomer. The substrate is then baked again to cure the monolayer of amino-functionalized monomer to the exposed quartz. After baking, the remaining photo-resist may be removed using acetone. Because of the difference in attachment chemistry between the resist and silane, aminosilane-functionalized areas on the substrate may remain intact through the acetone rinse. These areas can be further functionalized by reacting them with p-phenylenediisothiocyanate in a solution of pyridine and N—N-dimethylformamide. The substrate is then capable of reacting with amine-modified oligonucleotides. Alternatively, oligonucleotides can be prepared with a 5'-carboxymodifier-c10 linker (Glen Research). This technique allows the oligonucleotide to be attached directly to the amine modified support, thereby avoiding additional functionalization steps.

In another aspect, surfaces containing a plurality of discrete spaced apart regions are fabricated by nano-imprint lithography (NIL). For DNA array production, a quartz substrate is spin coated with a layer of resist, commonly called the transfer layer. A second type of resist is then applied over the transfer layer, commonly called the imprint layer. The master imprint tool then makes an impression on the imprint layer. The overall thickness of the imprint layer is then reduced by plasma etching until the low areas of the imprint reach the transfer layer. Because the transfer layer is harder to remove than the imprint layer, it remains largely untouched. The imprint and transfer layers are then hardened by heating. The substrate is then put into a plasma etcher until the low areas of the imprint reach the quartz. The substrate is then derivatized by vapor deposition as described above.

In another aspect, surfaces containing a plurality of discrete spaced apart regions are fabricated by nano printing. This process uses photo, imprint, or e-beam lithography to create a master mold, which is a negative image of the features required on the print head. Print heads are usually made of a soft, flexible polymer such as polydimethylsiloxane (PDMS). This material, or layers of materials having different properties, are spin coated onto a quartz substrate. The mold is then used to emboss the features onto the top layer of resist material under controlled temperature and pressure conditions. The print head is then subjected to a plasma based etching process to improve the aspect ratio of the print head, and eliminate distortion of the print head due to relaxation over time of the embossed material. Random array substrates are manufactured using nano-printing by depositing a pattern of amine modified oligonucleotides onto a homogenously derivatized surface. These oligo-nucleotides would serve as capture probes for the RCR products. One potential advantage to nano-printing is the ability to print interleaved patterns of different capture probes onto the random array support. This would be accomplished by successive printing with multiple print heads, each head having a differing pattern, and all patterns fitting together to form the final structured support pattern. Such methods allow for some positional encoding of DNA elements within the random array. For example, control concatemers containing a specific sequence can be bound at regular intervals throughout a random array.

In still another aspect, a high density array of capture oligonucleotide spots of sub micron size is prepared using a printing head or imprint-master prepared from a bundle, or bundle of bundles, of about 10,000 to 100 million optical fibers with a core and cladding material. By pulling and fusing fibers a unique material is produced that has about 50-1000 nm cores separated by a similar or 2-5 fold smaller or larger size cladding material. By differential etching (dissolving) of cladding material a nano-printing head is obtained having a very large number of nano-sized posts. This printing head may be used for depositing oligonucleotides or other biological (proteins, oligopeptides, DNA, aptamers) or chemical compounds such as silane with various active groups. In one embodiment the glass fiber tool is used as a patterned support to deposit oligonucleotides or other biological or chemical compounds. In this case only posts created by etching may be contacted with material to be deposited. Also, a flat cut of the fused fiber bundle may be used to guide light through cores and allow light-induced chemistry to occur only at the tip surface of the cores, thus eliminating the need for etching. In both cases, the same support may then be used as a light guiding/collection device for imaging fluorescence labels used to tag oligonucleotides or other reactants. This device provides a large field of view with a large numerical aperture (potentially >1). Stamping or printing tools that perform active material or oligonucleotide deposition may be used to print 2 to 100 different oligonucleotides in an interleaved pattern. This process requires precise positioning of the print head to about 50-500 nm. This type of oligonucleotide array may be used for attaching 2 to 100 different DNA populations such as different source DNA. They also may be used for parallel reading from sub-light resolution spots by using DNA specific anchors or tags. Information can be accessed by DNA specific tags, e.g. 16 specific anchors for 16 DNAs and read 2 bases by a combination of 5-6 colors and using 16 ligation cycles or one ligation cycle and 16 decoding cycles. This way of making arrays is efficient if limited information (e.g. a small number of cycles) is required per fragment, thus providing more information per cycle or more cycles per surface.

In one embodiment "inert" concatemers are used to prepare a surface for attachment of test concatemers. The surface is first covered by capture oligonucleotides complementary to the binding site present on two types of synthetic concatemers; one is a capture concatemer, the other is a spacer concatemer. The spacer concatemers do not have DNA segments complementary to the adapter used in preparation of test concatemers and they are used in about 5-50, preferably 10× excess to capture concatemers. The surface with capture oligonucleotide is "saturated" with a mix of synthetic concatemers (prepared by chain ligation or by RCR) in which the spacer concatemers are used in about 10-fold (or 5 to 50-fold) excess to capture concatemers. Because of the ~10:1 ratio between spacer and capture concatemers, the capture concatemers are mostly individual islands in a sea of spacer concatemers. The 10:1 ratio provides that two capture concatemers are on average separated by two spacer concatemers. If concatemers are about 200 nm in diameter, then two capture concatemers are at about 600 nm center-to-center spacing. This surface is then used to attach test concatemers or other molecular structures that have a binding site complementary to a region of the capture concatemers but not present on the spacer concatemers. Capture concatemers may be prepared to have less copies than the number of binding sites in test concatemers to assure single test concatemer attachment per capture concatemer spot. Because the test DNA can bind only to capture concatemers, an array of test concatemers may be prepared that have high site occupancy without congregation. Due to random attachment, some areas on the surface may not have any concatemers attached, but these areas with free capture oligonucleotide may not be able to bind test concatemers since they are designed not to have binding sites for the capture oligonucleotide. An array of individual test concatemers as described would not be arranged in a grid pattern. An ordered grid pattern should simplify data collection because less pixels are needed and less sophisticated image analysis systems are needed also.

In one aspect, multiple arrays of the invention may be place on a single surface. For example, patterned array substrates may be produced to match the standard 96 or 384 well plate format. A production format can be an 8×12 pattern of 6 mm×6 mm arrays at 9 mm pitch or 16×24 of 3.33 mm×3.33 mm array at 4.5 mm pitch, on a single piece of glass or plastic and other optically compatible material. In one example each 6 mm×6 mm array consists of 36 million 250-500 nm square regions at 1 micrometer pitch. Hydrophobic or other surface or physical barriers may be used to prevent mixing different reactions between unit arrays.

By way of example, binding sites (i.e. discrete spaced apart regions) for DNA samples are prepared by silanization of lithographically defined sites on silicon dioxide on silicon, quartz, or glass surfaces with 3-aminopropyldimethylethoxysilane or similar silanization agent followed by derivatization with p-phenylenediisothiocyanate or similar derivatization agent. For example, the binding sites may be square, circular or regular/irregular polygons produced by photolithography, direct-write electron beam, or nano-imprint lithography. Minimization of non-specific binding in regions between binding site The wettability (hydrophobic v. hydrophilic) and reactivity of the field surrounding the binding sites can be controlled to prevent DNA samples from binding in the field; that is, in places other than the binding sites. For example, the field may be prepared with hexamethyldisilazane (HMDS), or a similar agent covalently bonded to the surface, to be hydrophobic and hence unsuitable to hydrophilic bonding of the DNA samples. Similarly, the field may be coated with a chemical agent such as a fluorine-based carbon compound that renders it unreactive to DNA samples.

For the three surface fabrication processes listed in the prior paragraph, the follow exemplary steps are followed. For photolithography:
1) Clean glass wafer
2) Prime surface with HMDS
3) Pattern binding sites in photoresist
4) Reactive ion etch binding site surface with oxygen to remove HMDS
5) Silanize with 0.3% 3-aminopropyldimethylethoxysilane
6) Coat with photoresist to protect wafer during sawing
7) Saw wafer into chips
8) Strip photoresist
9) Derivatize binding sites with solution of 10% pyridine and 90% N,N-Dimethylformamide (DMF) using 2.25 mg p-phenylenediisothiocyanate (PDC) per ml of solution for 2 h followed by methanol, acetone, and water rinses For direct write electron beam surface fabrication
1) Clean glass wafer
2) Prime surface with HMDS
3) Pattern binding sites in PMMA with electron beam
4) Reactive ion etch binding site surface with oxygen to remove HMDS
5) Silanize with 0.3% 3-aminopropyldimethylethoxysilane
6) Coat with photoresist to protect wafer during sawing
7) Saw wafer into chips
8) Strip photoresist
9) Derivatize binding sites with solution of 10% pyridine and 90% N,N Dimethylformamide (DMF) using 2.25 mg p-phenylenediisothiocyanate (PDC) per ml of solution for 2 h followed by methanol, acetone, and water rinses.

For nano imprint lithography surface fabrication:
1) Clean glass wafer
2) Prime surface with HMDS
3) Coat wafer with transfer layer
4) Contact print pattern with nano imprint template and photopolymer on top of transfer layer
5) Dry etch pattern into transfer layer
6) Reactive ion etch binding site surface with oxygen to remove HMDS
7) Silanize with 0.3% 3-aminopropyldimethylethoxysilane
8) Coat with photoresist to protect wafer during sawing
9) Saw wafer into chips
10) Strip photoresist
11) Derivatize binding sites with solution of 10% pyridine and 90% N,N Dimethylformamide (DMF) using 2.25 mg p-phenylenediisothiocyanate (PDC) per ml of solution for 2 h followed by methanol, acetone, and water rinses.

As mentioned above, a glass surface may also be used for constructing random arrays of the invention. For example, a suitable glass surface may be constructed from microscope cover slips. Microscope cover slips (22 mm sq ~170 um thick) are placed in Teflon racks. They are soaked in 3 molar KOH in 95% ethanol/water for 2 minutes. They are then rinsed in water, followed by an acetone rinse. This removes surface contamination and prepares the glass for silanization. Plasma cleaning is an alternative to KOH cleaning. Fused silica or quartz may also be substituted for glass. The clean, dry cover slips are immersed in 0.3% 3-aminopropyldimethylethoxysilane, 0.3% water, in acetone. They are left to react for 45 minutes. They are then rinsed in acetone and cured at 100° C. for 1 hour. 3-aminopropyldimethylethoxysilane may be used as a replacement for 3-aminopropyltriethoxysilane because it forms a mono-layer on the glass surface. The monolayer surface provides a lower background. The silanization agent may also be applied using vapor deposition. 3-aminopropyltriethoxysilane tends to form more of a polymeric surface when deposited in solution phase. The amino modified silane is then terminated with a thiocyanate group. This is done in a solution of 10% pyridine and 90% N,N-Dimethylformamide (DMF) using 2.25 mg p-phenylenediisothiocyanate (PDC) per ml of solution. The reaction is run for 2 hours, then the slide is washed in methanol, followed by acetone, and water rinses. The cover slips are then dried and ready to bind probe. There are additional chemistries that can be used to modify the amino group at the end of the silanization agent. For example, glutaraldehyde can be used to modify the amino group at the end of the silanization agent to a aldehyde group which can be coupled to an amino modified oligonucleotide. Capture oligonucleotides are bound to the surface of the cover slide by applying a solution of 10-50 micromolar capture oligonucleotide in 100 millimolar sodium bicarbonate in water to the surface. The solution is allowed to dry, and is then washed in water. It may be beneficial to avoid terminating the 3-amino group with PDC and perform a direct conjugation (of the 3-amino end) to the capture oligonucleotide which has been modified with either a carboxyl group or an aldehyde group at the 5' end. In the case of the carboxyl group, the oligonucleotide is applied in a solution that contains EDC (1-Ethyl-3-(3-dimethylaminopropyl)-carbodiimide). In the case of the aldehyde group, the oligo is kept wet for 5-10 minutes then the surface is treated with a 1% solution of sodium borohydride.

In another aspect of the invention, random arrays are prepared using nanometer-sized beads. Sub-micron glass or other types of beads (e.g. in the 20-50 nm range) are used which are derivatized with a short oligonucleotide, e.g. 6-30 nucleotides, complementary to an adaptor oligonucleotide in the circles used to generate concatemers. The number of oligonucleotides on the bead and the length of the sequence can be controlled to weakly bind the concatemers in solution. Reaction rate of the beads should be much faster than that of the solid support alone. After binding concatemers, the beads are then allowed to settle on the surface of an array substrate. The array substrate has longer, more stable, more numerous oligonucleotides, such that conditions may be selected to permit preferential binding to the surface, thereby forming a spaced array of concatemers. If the beads are magnetic, a magnetic field can be used to pull them to the surface, it may also be used to move them around the surface. Alternatively, a centrifuge may be used to concentrate the beads on the surface. An exemplary protocol is as follows: 1. A preparation of 20 ul of concatemer solution with one million concatemers per 1 ul is mixed with 20 million nano-beads with about 500 capture oligonucleotides about 8 bases in length (6-16 bases may be use under different conditions). A 100 mm nano-bead there is approximately 40,000 nm2 and can hold up to 4000 short oligonucleotides. One way to control the density of capture probes is to mix in this case about 8 times more of a 2-4 bases long oligonucleotides with the same attachment chemistry with the capture probe. Also, much smaller nano-beads (20-50 nm) may be used. 2. Reaction conditions (temperature, pH, salt concentration) are adjusted so that concatemers with over 300 copies will attach to nanobeads in significant numbers. 3. The reaction is applied under the same stringent conditions to a support with 4×4 mm of patterned surface with 16 million active sites about 200 nm in size, and nanobeads are allowed or forced to settle on the substrate surface bringing large concatemers with them. The largest distance that a nano-bead-concatemer has to travel is about 1 mm. The vertical movement of beads minimizes number of potential concatemer-concatemer encounters. The reaction solution may be applied in aliquots, e.g. 4 applications 5 ul each. In this case the thickness of the applied solution (e.g. the nano-bead maximal travel distance) is only about 250 microns. 4. Further increase stringency of the reaction to release concatemers from nano-beads and attach them to active sites on the support with ~300 capture oligonucleotides 20-50 bases in length. 5. Concatemers attached to nano-beads will predominately settle initially between active sites on the support because there are 25 times more inactive than active surface. Slight horizontal movement force (e.g. substrate tilting, and other forces), may be applied to move nano-bead-concatemers about one to a few microns around.

Detection Instrumentation

As mentioned above, signals from single molecules on random arrays made in accordance with the invention are generated and detected by a number of detection systems, including, but not limited to, scanning electron microscopy, near field scanning optical microscopy (NSOM), total internal reflection fluorescence microscopy (TIRFM), and the like. Abundant guidance is found in the literature for applying such techniques for analyzing and detecting nanoscale structures on surfaces, as evidenced by the following references that are incorporated by reference: Reimer et al, editors, Scanning Electron Microscopy: Physics of Image Formation and Microanalysis, $2^{nd}$ Edition (Springer, 1998); Nie et al, Anal. Chem., 78: 1528-1534 (2006); Hecht et al, Journal Chemical Physics, 112: 7761-7774 (2000); Zhu et al, editors, Near-Field Optics: Principles and Applications (World Scientific Publishing, Singapore, 1999); Drmanac, International patent publication WO 2004/076683; Lehr et al, Anal. Chem., 75: 2414-2420 (2003); Neuschafer et al, Biosensors & Bioelectronics, 18: 489-497 (2003); Neuschafer et al, U.S. Pat. No. 6,289,144; and the like. Of particular interest is TIRFM, for example, as disclosed by Neuschafer et al, U.S. Pat. No. 6,289,144; Lehr et al (cited above); and Drmanac, International patent publication WO 2004/076683. In one aspect, instruments for use with arrays of the invention comprise three basic components: (i) a fluidics system for storing and transferring detection and processing reagents, e.g. probes, wash solutions, and the like, to an array; (ii) a reaction chamber, or flow cell, holding or comprising an array and having flow-through and temperature control capability; and (iii) an illumination and detection system. In one embodiment, a flow cell has a temperature control subsystem with ability to maintain temperature in the range from about 5-95° C., or more specifically 10-85° C., and can change temperature with a rate of about 0.5-2° C. per second.

In one aspect, a flow cell for 1" square 170 micrometer thick cover slips can be used that has been derivatized to bind macromolecular structures of the invention. The cell encloses the "array" by sandwiching the glass and a gasket between two planes. One plane has an opening of sufficient size to permit imaging, and an indexing pocket for the cover slip. The other plane has an indexing pocket for the gasket, fluid ports, and a temperature control system. One fluid port is connected to a syringe pump which "pulls" or "pushes" fluid from the flow cell the other port is connected to a funnel like mixing chamber. The chamber, in turn is equipped with a liquid level sensor. The solutions are dispensed into the funnel, mixed if needed, then drawn into the flow cell. When the level sensor reads air in the funnels connection to the flow cell the pump is reversed a known amount to back the fluid up to the funnel. This prevents air from entering the flow cell. The cover slip surface may be sectioned off and divided into strips to accommodate fluid flow/capillary effects caused by sandwiching. Such substrate may be housed in an "open air"/"open face" chamber to promote even flow of the buffers over the substrate by eliminating capillary flow effects. Imaging may be accomplished with a 100× objective using TIRF or epi illumination and a 1.3 mega pixel Hamamatsu orca-er-ag on a Zeiss axiovert 200, or like system. This configuration images RCR concatemers bound randomly to a substrate (non-ordered array). Imaging speed may be improved by decreasing the objective magnification power, using grid patterned arrays and increasing the number of pixels of data collected in each image. For example, up to four or more cameras may be used, preferably in the 10-16 megapixel range. Multiple band pass filters and dichroic mirrors may also be used to collect pixel data across up to four or more emission spectra. To compensate for the lower light collecting power of the decreased magnification objective, the power of the excitation light source can be increased. Throughput can be increased by using one or more flow chambers with each camera, so that the imaging system is not idle while the samples are being hybridized/reacted. Because the probing of arrays can be non-sequential, more than one imaging system can be used to collect data from a set of arrays, further decreasing assay time.

During the imaging process, the substrate must remain in focus. Some key factors in maintaining focus are the flatness of the substrate, orthogonality of the substrate to the focus plane, and mechanical forces on the substrate that may deform it. Substrate flatness can be well controlled, glass plates which have better than ¼ wave flatness are readily obtained. Uneven mechanical forces on the substrate can be minimized through proper design of the hybridization chamber. Orthogonality to the focus plane can be achieved by a well adjusted, high precision stage. Auto focus routines generally take additional time to run, so it is desirable to run them only if necessary. After each image is acquired, it will be analyzed using a fast algorithm to determine if the image is in focus. If the image is out of focus, the auto focus routine will run. It will then store the objectives Z position information to be used upon return to that section of that array during the next imaging cycle. By mapping the objectives Z position at various locations on the substrate, we will reduce the time required for substrate image acquisition.

A suitable illumination and detection system for fluorescence-based signal is a Zeiss Axiovert 200 equipped with a TIRF slider coupled to a 80 milliwatt 532 nm solid state laser. The slider illuminates the substrate through the objective at the correct TIRF illumination angle. TIRF can also be accomplished without the use of the objective by illuminating the substrate though a prism optically coupled to the substrate. Planar wave guides can also be used to implement TIRF on the substrate Epi illumination can also be employed. The light source can be rastered, spread beam, coherent, incoherent, and originate from a single or multi-spectrum source.

One embodiment for the imaging system contains a 20× lens with a 1.25 mm field of view, with detection being accomplished with a 10 megapixel camera. Such a system images approx 1.5 million concatemers attached to the patterned array at 1 micron pitch. Under this configuration there are approximately 6.4 pixels per concatemer. The number of pixels per concatemer can be adjusted by increasing or decreasing the field of view of the objective. For example a 1 mm field of view would yield a value of 10 pixels per concatemer and a 2 mm field of view would yield a value of 2.5 pixels per concatemer. The field of view may be adjusted relative to the magnification and NA of the objective to yield the lowest pixel count per concatemer that is still capable of being resolved by the optics, and image analysis software.

Both TIRF and EPI illumination allow for almost any light source to be used. One illumination schema is to share a common set of monochromatic illumination sources (about 4 lasers for 6-8 colors) amongst imagers. Each imager collects data at a different wavelength at any given time and the light sources would be switched to the imagers via an optical switching system. In such an embodiment, the illumination source preferably produces at least 6, but more preferably 8 different wavelengths. Such sources include gas lasers, multiple diode pumped solid state lasers combined through a fiber coupler, filtered Xenon Arc lamps, tunable lasers, or the more novel Spectralum Light Engine, soon to be offered by Tidal Photonics. The Spectralum Light Engine uses prism to spectrally separate light. The spectrum is projected onto a Texas Instruments Digital Light Processor, which can selectively reflect any portion of the spectrum into a fiber or optical connector. This system is capable of monitoring and calibrating the power output across individual wavelengths to keep them constant so as to automatically compensate for intensity differences as bulbs age or between bulb changes.

The following table represent examples of possible lasers, dyes and filters.

| laser | excitation filter | emission filter | Dye | |
|---|---|---|---|---|
| 407 nm | 405/12 | 436/12 | Alexa-405 | 401/421 |
| 407 nm | 405/12 | 546/10 | cascade yellow | 409/558 |
| 488 nm | 488/10 | 514/11 | Alexa-488 | 492/517 |
| 543 nm | 546/10 | 540/565 | Tamra | 540/565 |
| | | | Bodipy | |
| 543 nm | 546/10 | 620/12 | 577/618 | 577/618 |
| | 546/10 | 620/12 | Alexa-594 | 594/613 |
| 635 nm | 635/11 | 650/11 | Alexa-635 | 632/647 |
| 635 nm | 635/11 | | Alexa700 | 702/723 |

Successfully scoring 6 billion concatemers through ~350 (~60 per color) images per region over 24 hours may require a combination of parallel image acquisition, increased image acquisition speed, and increased field of view for each imager. Additionally, the imager may support between six to eight colors. Commercially available microscopes commonly image a ~1 mm field of view at 20× magnification with an NA of 0.8. At the proposed concatemer pitch of 0.5 micron, this translates into roughly 4 million concatemers per image. This yields approximately 1,500 images for 6 billion spots per hybridization cycle, or 0.5 million images for 350 imaging cycles. In a large scale sequencing operation, each imager preferably acquires ~200,000 images per day, based on a 300 millisecond exposure time to a 16 mega pixel CCD. Thus, a preferred instrument design is 4 imager modules each serving 4 flow cells (16 flow cells total). The above described imaging schema assumes that each imager has a CCD detector with 10 million pixels and be used with an exposure time of roughly 300 milliseconds. This should be an acceptable method for collecting data for 6 fluorophor labels. One possible drawback to this imaging technique is that certain fluorophors may be unintentionally photo bleached by the light source while other fluorophores are being imaged. Keeping the illumination power low and exposure times to a minimum would greatly reduce photo bleaching. By using intensified CCDs (ICCDs) data could be collected of roughly the same quality with illumination intensities and exposure times that are orders of magnitude lower than standard CCDs. ICCDs are generally available in the 1-1.4 megapixel range. Because they require much shorter exposure times, a one megapixel ICCD can acquire ten or more images in the time a standard CCD acquires a single image. Used in conjunction with fast filter wheels, and a high speed flow cell stage, a one mega pixel ICCD should be able to collect the same amount of data as a 10 megapixel standard CCD.

Optics capable of imaging larger fields of view with high numerical apertures can be manufactured as custom lens assemblies. Indications are that 20× optics capable of imaging a 3 mm field of view with a NA >0.9 can be fabricated. Two such imaging systems, in combination with high pixel count CCD's or CCD mosaic arrays should be able to image the complete eight flow cell assay in roughly 14 hours. As described, further gains can be realized by using 16 flow cells. Doubling the number of flow cells would reduce imaging time to 9 hours by reducing the number of images per each field of view.

The reaction efficiency on the concatemer and other random DNA arrays may depend on the efficient use of probes, anchors or primers and enzymes. This may be achieved by mixing liquids (such as pooling liquid back and forth in the flow through chamber), applying agitations or using horizontal or vertical electric fields to bring DNA from different parts of the reaction volume in the proximity of the surface. One approach for efficient low cost assay reaction is to apply reaction mixes in a thin layer such as droplets or layers of about one to a few microns, but preferably less than 10 microns, in size/thickness. In a 1×1×1 micron volume designated for a 1×1 micron spot area, in pmol/1 ul (1 uM concentration) there would be about 1000 molecules of probe in close proximity to 1-1000 copies of DNA. Using up to 100-300 molecules of probes would not significantly reduce the probe concentration and it would provide enough reacted probes to get significant signal. This approach may be used in an open reaction chamber that may stay open or closed for removal and washing of the probes and enzyme.

As mentioned above, higher throughput can be achieved by using multiple cameras and multiple flow cells. A single robotic liquid handling gantry may service, for example, 16 flow cells. In addition, all components of the system may share a common temperature control system, and set of reagents. For combinatorial SBH sequencing operations, the robot may prepare probe pools and ligation buffers to be dispensed into the flow cell funnels. Dedicated syringe pumps may dispense wash and hybridization buffers directly into the funnel ports for each flow cell. Each imager may service a group of 2-4 flow cells. Each group of flow cells may be positioned on an XY motion platform, similar to the automated plate stages commonly found on research microscopes. System control and coordination between all system components may be performed via software running on a master computer. The control software may run assay cycles asynchronously, allowing each imager to run continuously throughout the assay. Flow cells are connected to a temperature control system with one heater and one chiller allowing for heating or cooling on demand of each flow cell or 2-4 blocks of cells independently. Each flow cell temperature may be monitored, and if a flow cell temperature drops below a set threshold, a valve may open to a hot water recirculation. Likewise, if a flow cell temperature is above the set threshold a valve may open to a cold water recirculation. If a flow cell is within a set temperature range neither valve may open. The hot and cold recirculation water runs through the aluminum flow cell body, but remains separate and isolated from the assay buffers and reagents.

Sequence Analysis of Random Arrays of Target Sequence Concatemers

As mentioned above, random arrays of biomolecules, such as genomic DNA fragments or cDNA fragments, provides a platform for large scale sequence determination and for genome-wide measurements based on counting sequence tags, in a manner similar to measurements made by serial analysis of gene expression (SAGE) or massively parallel signature sequencing, e.g. Velculescu, et al, (1995), Science 270, 484-487; and Brenner et al (2000), Nature Biotechnology, 18: 630-634. Such genome-wide measurements include, but are not limited to, determination of polymorphisms, including nucleotide substitutions, deletions, and insertions, inversions, and the like, determination of methylation patterns, copy number patterns, and the like, such as could be carried out by a wide range of assays known to those with ordinary skill in the art, e.g. Syvanen (2005), Nature Genetics Supplement, 37: S5-S10; Gunderson et al (2005), Nature Genetics, 37: 549-554; Fan et al (2003), Cold Spring Harbor Symposia on Quantitative Biology, LXVIII: 69-78; and U.S. Pat. Nos. 4,883,750; 6,858,412; 5,871,921; 6,355,431; and the like, which are incorporated herein by reference.

A variety of sequencing methodologies can be used with random arrays of the invention, including, but not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g. Nyren et al, U.S. Pat. No. 6,210,891; Ronaghi, U.S. Pat. No. 6,828,100; Ronaghi et al (1998), Science, 281: 363-365; Balasubramanian, U.S. Pat. No. 6,833,246; Quake, U.S. Pat. No. 6,911,345; Li et al, Proc. Natl. Acad. Sci., 100: 414-419 (2003), which are incorporated by reference, and ligation-based methods, e.g. Shendure et al (2005), Science, 309: 1728-1739, which is incorporated by reference. In one aspect, a method of determining a nucleotide sequence of a target polynucleotide in accordance with the invention comprises the following steps: (a) generating a plurality of target concatemers from the target polynucleotide, each target concatemer comprising multiple copies of a fragment of the target polynucleotide and the plurality of target concatemers including a number of fragments that substantially covers the target polynucleotide; (b) forming a random array of target concatemers fixed to a surface at a density such that at least a majority of the target concatemers are optically resolvable; (c) identifying a sequence of at least a portion of each fragment in each target concatemer; and (d) reconstructing the nucleotide sequence of the target polynucleotide from the identities of the sequences of the portions of fragments of the concatemers. Usually, "substantially covers" means that the amount of DNA analyzed contains an equivalent of at least two copies of the target polynucleotide, or in another aspect, at least ten copies, or in another aspect, at least twenty copies, or in another aspect, at least 100 copies. Target polynucleotides may include DNA fragments, including genomic DNA fragments and cDNA fragments, and RNA fragments. Guidance for the step of reconstructing target polynucleotide sequences can be found in the following references, which are incorporated by reference: Lander et al, Genomics, 2: 231-239 (1988); Vingron et al, J. Mol. Biol., 235: 1-12 (1994); and like references.

In one aspect, a sequencing method for use with the invention for determining sequences in a plurality of DNA or RNA fragments comprises the following steps: (a) generating a plurality of polynucleotide molecules each comprising a concatemer of a DNA or RNA fragment; (b) forming a random array of polynucleotide molecules fixed to a surface at a density such that at least a majority of the target concatemers are optically resolvable; and (c) identifying a sequence of at least a portion of each DNA or RNA fragment in resolvable polynucleotides using at least one chemical reaction of an optically detectable reactant. In one embodiment, such optically detectable reactant is an oligonucleotide. In another embodiment, such optically detectable reactant is a nucleoside triphosphate, e.g. a fluorescently labeled nucleoside triphosphate that may be used to extend an oligonucleotide hybridized to a concatemer. In another embodiment, such optically detectable reagent is an oligonucleotide formed by ligating a first and second oligonucleotides that form adjacent duplexes on a concatemer. In another embodiment, such chemical reaction is synthesis of DNA or RNA, e.g. by extending a primer hybridized to a concatemer. In yet another embodiment, the above optically detectable reactant is a nucleic acid binding oligopeptide or polypeptide or protein.

In one aspect, parallel sequencing of polynucleotide analytes of concatemers on a random array is accomplished by combinatorial SBH (cSBH), as disclosed by Drmanac in the above-cited patents. In one aspect, a first and second sets of oligonucleotide probes are provide, wherein each sets has member probes that comprise oligonucleotides having every possible sequence for the defined length of probes in the set. For example, if a set contains probes of length six, then it contains 4096 ($=4^6$) probes. In another aspect, first and second sets of oligonucleotide probes comprise probes having selected nucleotide sequences designed to detect selected sets of target polynucleotides. Sequences are determined by hybridizing one probe or pool of probe, hybridizing a second probe or a second pool of probes, ligating probes that form perfectly matched duplexes on their target sequences, identifying those probes that are ligated to obtain sequence information about the target sequence, repeating the steps until all the probes or pools of probes have been hybridized, and determining the nucleotide sequence of the target from the sequence information accumulated during the hybridization and identification steps.

For sequencing operation, in some embodiments, the sets may be divided into subsets that are used together in pools, as disclosed in U.S. Pat. No. 6,864,052. Probes from the first and second sets may be hybridized to target sequences either together or in sequence, either as entire sets or as subsets, or pools. In one aspect, lengths of the probes in the first or second sets are in the range of from 5 to 10 nucleotides, and in another aspect, in the range of from 5 to 7 nucleotides, so that when ligated they form ligation products with a length in the range of from 10 to 20, and from 10 to 14, respectively.

In another aspect, using such techniques, the sequence identity of each attached DNA concatemer may be determined by a "signature" approach. About 50 to 100 or possibly 200 probes are used such that about 25-50% or in some applications 10-30% of attached concatemers will have a full match sequence for each probe. This type of data allows each amplified DNA fragment within a concatemer to be mapped to the reference sequence. For example, by such a process one can score 64 4-mers (i.e. 25% of all possible 256 4-mers) using 16 hybridization/stripoff cycles in a 4 colors labeling schema. On a 60-70 base fragment amplified in a concatemer about 16 of 64 probes will be positive since there are 64 possible 4mers present in a 64 base long sequence (i.e. one quarter of all possible 4mers). Unrelated 60-70 base fragments will have a very different set of about 16 positive decoding probes. A combination of 16 probes out of 64 probes has a random chance of occurrence in 1 of every one billion fragments which practically provides a unique signature for that concatemer. Scoring 80 probes in 20 cycles and generating 20 positive probes create a signature even more likely to be unique: occurrence by chance is 1 in billion billions. Previously, a "signature" approach was used to select novel genes from cDNA libraries. An implementation of a signature approach is to sort obtained intensities of all tested probes and select up to a predefined (expected) number of probes that satisfy the positive probe threshold. These probes will be mapped to sequences of all DNA fragments (sliding window of a longer reference sequence may be used) expected to be present in the array. The sequence that has all or a statistically sufficient number of the selected positive probes is assigned as the sequence of the DNA fragment in the given concatemer. In another approach an expected signal can be defined for all used probes using their pre measured full match and mismatch hybridization/ligation efficiency. In this case a measure similar to the correlation factor can be calculated.

A preferred way to score 4-mers is to ligate pairs of probes, for example: $N_{(5-7)}BBB$ with $BN_{(7-9)}$, where B is the defined base and N is a degenerate base. For generating signatures on longer DNA concatemer probes, more unique bases will be used. For example, a 25% positive rate in a fragment 1000 bases in length would be achieved by $N_{(4-6)}BBBB$ and $BBN_{(6-8)}$. Note that longer fragments need the same number of about 60-80 probes (15-20 ligation cycles using 4 colors).

In one embodiment all probes of a given length (e.g. 4096 $N_{2-4}BBBBBBN_{2-4}$) or all ligation pairs may be used to determine complete sequence of the DNA in a concatemer. For example, 1024 combinations of $N_{(5-7)}B_3$ and $BBN_{(6-8)}$ may be scored (256 cycles if 4 colors are used) to determine sequence of DNA fragments of up to about 250 bases, preferably up to about 100 bases.

The decoding of sequencing probes with large numbers of Ns may be prepared from multiple syntheses of subsets of sequences at degenerated bases to minimize difference in the efficiency. Each subset is added to the mix at a proper concentration. Also, some subsets may have more degenerated positions than others. For example, each of 64 probes from the set $N_{(5-7)}BBB$ may be prepared in 4 different synthesis. One is regular all 5-7 bases to be fully degenerated; second is N0-3(A,T)5BBB; third is N0-2(A,T)(G,C)(A,T)(G,C)(A,T) BBB, and the fourth is N0-2(G,C)(A,T)(G,C)(A,T)(G,C) BBB.

Oligonucleotide preparation from the three specific syntheses is added in to regular synthesis in experimentally determined amounts to increase hybrid generation with target sequences that have in front of the BBB sequence an AT rich (e.g. AATAT) or (A or T) and (G or C) alternating sequence (e.g. ACAGT or GAGAC). These sequences are expected to be less efficient in forming a hybrid. All 1024 target sequences can be tested for the efficiency to form hybrid with $N_{0-3}NNNNNBBB$ probes and those types that give the weakest binding may be prepared in about 1-10 additional synthesis and added to the basic probe preparation.

Decoding by Signatures: a smaller number of probes for small number of distinct samples: 5-7 positive out of 20 probes (5 cycles using 4 colors) has capacity to distinct about 10-100 thousand distinct fragments Decoding of 8-20mer RCR products. In this application arrays are formed as random distributions of unique 8 to 20 base recognition sequences in the form of DNA concatemers. The probes need to be decoded to determine the sequence of the 8-20 base probe region. At least two options are available to do this and the following example describes the process for a 12 mer. In the first, one half of the sequence is determined by utilizing the hybridization specificity of short probes and the ligation specificity of fully matched hybrids. Six to ten bases adjacent to the 12 mer are predefined and act as a support for a 6mer to 10-mer oligonucleotide. This short 6mer will ligate at its 3-prime end to one of 4 labeled 6-mers to 10-mers. These decoding probes consist of a pool of 4 oligonucleotides in which each oligonucleotide consists of 4-9 degenerate bases and 1 defined base. This oligonucleotide will also be labeled with one of four fluorescent labels. Each of the 4 possible bases A, C, G, or T will therefore be represented by a fluorescent dye. For example these 5 groups of 4 oligonucleotides and one universal oligonucleotide (Us) can be used in the ligation assays to sequence first 5 bases of 12-mers: B=each of 4 bases associated with a specific dye or tag at the end:

UUUUUUUU.BNNNNNNN*
UUUUUUUU.NBNNNNNN
UUUUUUUU.NNBNNNN
UUUUUUUU.NNNBNNNN
UUUUUUUU.NNNNBNNN

Six or more bases can be sequences with additional probe pools. To improve discrimination at positions near the center of the 12mer the 6mer oligonucleotide can be positioned further into the 12mer sequence. This will necessitate the incorporation of degenerate bases into the 3-prime end of the non-labeled oligonucleotide to accommodate the shift. This is an example of decoding probes for position 6 and 7 in the 12-mer.

UUUUUUNN.NNNBNNNN
UUUUUUNN.NNNNBNNN

In a similar way the 6 bases from the right side of the 12mer can be decoded by using a fixed oligonucleotide and 5-prime labeled probes. In the above described system 6 cycles are required to define 6 bases of one side of the 12mer. With redundant cycle analysis of bases distant to the ligation site this may increase to 7 or 8 cycles. In total then, complete sequencing of the 12mer could be accomplished with 12-16 cycles of ligation. Partial or complete sequencing of arrayed DNA by combining two distinct types of libraries of detector probes. In this approach one set has probes of the general type $N_{3-8}B_{4-6}$ (anchors) that are ligated with the first 2 or 3 or 4 probes/probe pools from the set $BN_{6-8}$, $NBN_{5-7}$, $N_2BN_{4-6}$, and $N_3BN_{3-5}$. The main requirement is to test in a few cycles a probe from the first set with 2-4 or even more probes from the second set to read longer continuous sequence such as 5−6+3−4=8−10 in just 3-4 cycles. In one example, the process is:

1) Hybridize 1-4 4-mers or more 5-mer anchors to obtain 70-80% 1 or 2 anchors per DNA. One way to discriminate which anchor is positive from the pool is to mix specific probes with distinct hybrid stability (maybe different number of Ns in addition). Anchors may be also tagged to determine which anchor from the pool is hybridized to a spot. Tags, as additional DNA segment, may be used for adjustable displacement as a detection method. For example, EEEEEEEENNNAAAAA and FFFFFFFFNNNCCCCC probes can be after hybridization or hybridization and ligation differentially removed with two corresponding displacers: EEEEEEEENNNNN and FFFFFFFFNNNNNN where the second is more efficient. Separate cycles may be used just to determine which anchor is positive. For this purpose anchors labeled or tagged with multiple colors may be ligated to unlabeled N7-N10 supporter oligonucleotides.

2) Hybridize BNNNNNNNN probe with 4 colors corresponding to 4 bases; wash discriminatively (or displace by complement to the tag) to read which of two scored bases is associated to which anchor if two anchors are positive in one DNA. Thus, two 7-10 base sequences can be scores at the same time.

In 2-4 cycles extend to 4-6 base anchor for additional 2-4 bases run 16 different anchors per each array (32-64 physical cycles if 4 colors are used) to determine about 16 possible 8-mers (~100 bases total) per each fragment (more then enough to map it to the reference (probability that a 100-mer will have a set of 10 8-mers is less than 1 in trillion trillions; (10exp-28). By combining data from different anchors scored in parallel on the same fragment in another array complete sequence of that fragment and by extension to entire genomes may be generated from overlapping 7-10-mers.

Tagging probes with DNA tags for larger multiplex of decoding or sequence determination probes Instead of directly labeling probes they can be tagged with different oligonucleotide sequences made of natural bases or new synthetic bases (such as isoG and isoC). Tags can be designed to have very precise binding efficiency with their anti-tags using different oligonucleotide lengths (about 6-24 bases) and/or sequence including GC content. For example 4 different tags may be designed that can be recognized with specific anti-tags in 4 consecutive cycles or in one hybridization cycle followed by a discriminative wash. In the discriminative wash initial signal is reduced to 95-99%, 30-40%, 10-20% and 0-5% for each tag, respectively. In this case by obtaining two images 4 measurements are obtained assuming that probes with different tags will rarely hybridize to the same dot. Another benefit of having many different tags even if they are consecutively decoded (or 2-16 at a time labeled with 2-16 distinct colors) is the ability to use a large number of individually recognizable probes in one assay reaction. This way a 4-64 times longer assay time (that may provide more specific or stronger signal) may be affordable if the probes are decoded in short incubation and removal reactions.

The decoding process requires the use of 48-96 or more decoding probes. These pools will be further combined into 12-24 or more pools by encoding them with four fluorophores, each having different emission spectra. Using a 20× objective, each 6 mm×6 mm array may require roughly 30 images for full coverage by using a 10 mega pixel camera with. Each of 1 micrometer array areas is read by about 8 pixels. Each image is acquired in 250 milliseconds, 150 ms for exposure and 100 ms to move the stage. Using this fast acquisition it will take ~7.5 seconds to image each array, or 12 minutes to image the complete set of 96 arrays on each substrate. In one embodiment of an imaging system, this high image acquisition rate is achieved by using four ten-megapixel cameras, each imaging the emission spectra of a different fluorophore. The cameras are coupled to the microscope through a series of dichroic beam splitters. The autofocus routine, which takes extra time, runs only if an acquired image is out of focus. It will then store the Z axis position information to be used upon return to that section of that array during the next imaging cycle. By mapping the autofocus position for each location on the substrate we will drastically reduce the time required for image acquisition.

Each array requires about 12-24 cycles to decode. Each cycle consists of a hybridization, wash, array imaging, and strip-off step. These steps, in their respective orders, may take for the above example 5, 2, 12, and 5 minutes each, for a total of 24 minutes each cycle, or roughly 5-10 hours for each array, if the operations were performed linearly. The time to decode each array can be reduced by a factor of two by allowing the system to image constantly. To accomplish this, the imaging of two separate substrates on each microscope is staggered. While one substrate is being reacted, the other substrate is imaged.

An exemplary decoding cycle using cSBH includes the following steps: (i) set temperature of array to hybridization temperature (usually in the range 5-25° C.); (ii) use robot pipetter to pre mix a small amount of decoding probe with the appropriate amount of hybridization buffer; (iii) pipette mixed reagents into hybridization chamber; (iv) hybridize for predetermined time; (v) drain reagents from chamber using pump (syringe or other); (vi) add a buffer to wash mismatches of non-hybrids; (vii) adjust chamber temperature to appropriate wash temp (about 10-40° C.); (viii) drain chamber; (ix) add more wash buffer if needed to improve imaging; (x) image each array, preferably with a mid power (20×) microscope objective optically coupled to a high pixel count high sensitivity ccd camera, or cameras; plate stage moves chambers (or perhaps flow-cells with input funnels) over object, or objective-optics assembly moves under chamber; certain optical arrangements, using di-chroic mirrors/beam-splitters can be employed to collect multi-spectral images simultaneously, thus decreasing image acquisition time; arrays can be imaged in sections or whole, depending on array/image size/pixel density; sections can be assembled by aligning images using statistically significant empty regions pre-coded onto substrate (during active site creation) or can be made using a multi step nano-printing technique, for example sites (grid of activated sites) can be printed using specific capture probe, leaving empty regions in the grid; then print a different pattern or capture probe in that region using separate print head; (xi) drain chamber and replace with probe strip buffer (or use the buffer already loaded) then heat chamber to probe stripoff temperature (60-90° C.); high pH buffer may be used in the strip-off step to reduce stripoff temperature; wait for the specified time; (xii) remove buffer; (xiii) start next cycle with next decoding probe pool in set.

Labels and Signal Generation by Probes Directed to Polynucleotides on Arrays of the Invention The oligonucleotide probes of the invention can be labeled in a variety of ways, including the direct or indirect attachment of radioactive moieties, fluorescent moieties, calorimetric moieties, chemiluminescent moieties, and the like. Many comprehensive reviews of methodologies for labeling DNA and constructing DNA adaptors provide guidance applicable to constructing oligonucleotide probes of the present invention. Such reviews include Kricka, Ann. Clin. Biochem., 39: 114-129 (2002); Schaferling et al, Anal. Bioanal. Chem., (Apr. 12, 2006); Matthews et al, *Anal. Biochem.*, Vol 169, pgs. 1-25 (1988); Haugland, Handbook of Fluorescent Probes and Research Chemicals, Tenth Edition (Invitrogen/Molecular Probes, Inc., Eugene, 2006); Keller and Manak, DNA Probes, 2nd Edition (Stockton Press, New York, 1993); and Eckstein, editor, Oligonucleotides and Analogues: A Practical Approach (IRL Press, Oxford, 1991); Wetmur, Critical Reviews in Biochemistry and Molecular Biology, 26: 227-259 (1991); Hermanson, Bioconjugate Techniques (Academic Press, New York, 1996); and the like. Many more particular methodologies applicable to the invention are disclosed in the following sample of references: Fung et al, U.S. Pat. No. 4,757,141; Hobbs, Jr., et al U.S. Pat. No. 5,151,507; Cruickshank, U.S. Pat. No. 5,091,519; (synthesis of functionalized oligonucleotides for attachment of reporter groups); Jablonski et al, Nucleic Acids Research, 14: 6115-6128 (1986) (enzyme-oligonucleotide conjugates); Ju et al, Nature Medicine, 2: 246-249 (1996); Bawendi et al, U.S. Pat. No. 6,326,144 (derivatized fluorescent nanocrytals); Bruchez et al, U.S. Pat. No. 6,274,323 (derivatized fluorescent nanocrystals); and the like.

In one aspect, one or more fluorescent dyes are used as labels for the oligonucleotide probes, e.g. as disclosed by Menchen et al, U.S. Pat. No. 5,188,934 (4,7-dichlorofluorscein dyes); Begot et al, U.S. Pat. No. 5,366,860 (spectrally resolvable rhodamine dyes); Lee et al, U.S. Pat. No. 5,847, 162 (4,7-dichlororhodamine dyes); Khanna et al, U.S. Pat. No. 4,318,846 (ether-substituted fluorescein dyes); Lee et al, U.S. Pat. No. 5,800,996 (energy transfer dyes); Lee et al, U.S. Pat. No. 5,066,580 (xanthene dyes): Mathies et al, U.S. Pat. No. 5,688,648 (energy transfer dyes); and the like. Labeling can also be carried out with quantum dots, as disclosed in the following patents and patent publications, incorporated herein by reference: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. As used herein, the term "fluorescent signal generating moiety" means a signaling means which conveys information through the fluorescent absorption and/or emission properties of one or more molecules. Such fluorescent properties include fluorescence intensity, fluorescence life time, emission spectrum characteristics, energy transfer, and the like.

Commercially available fluorescent nucleotide analogues readily incorporated into the labeling oligonucleotides include, for example, Cy3-dCTP, Cy3-dUTP, Cy5-dCTP, Cy5-dUTP (Amersham Biosciences, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY® R-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3.5, Cy5.5, and Cy7 (Amersham Biosciences, Piscataway, N.J. USA, and others). FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes. Biotin, or a derivative thereof, may also be used as a label on a detection oligonucleotide, and subsequently bound by a detectably labeled avidin/streptavidin derivative (e.g. phycoerythrin-conjugated streptavidin), or a detectably labeled anti-biotin antibody. Digoxigenin may be incorporated as a label and subsequently bound by a detectably labeled anti-digoxigenin antibody (e.g. fluoresceinated anti-digoxigenin). An aminoallyl-dUTP residue may be incorporated into a detection oligonucleotide and subsequently coupled to an N-hydroxy succinimide (NHS) derivatized fluorescent dye, such as those listed supra. In general, any member of a conjugate pair may be incorporated into a detection oligonucleotide provided that a detectably labeled conjugate partner can be bound to permit detection. As used herein, the term antibody refers to an antibody molecule of any class, or any subfragment thereof, such as an Fab. Other suitable labels for detection oligonucleotides may include fluorescein (FAM), digoxigenin, dinitrophenol (DNP), dansyl, biotin, bromodeoxyuridine (BrdU), hexahistidine (6×His), phosphor-amino acids (e.g. P-tyr, P-ser, P-thr), or any other suitable label. In one embodiment the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM. As described in schemes below, probes may also be indirectly labeled, especially with a hapten that is then bound by a capture agent, e.g. as disclosed in Holtke et al, U.S. Pat. Nos. 5,344,757; 5,702,888; and 5,354,657; Huber et al, U.S. Pat. No. 5,198,537; Miyoshi, U.S. Pat. No. 4,849,336; Misiura and Gait, PCT publication WO 91/17160; and the like. Many different hapten-capture agent pairs are available for use with the invention. Exemplary, haptens include, biotin, des-biotin and other derivatives, dinitrophenol, dansyl, fluorescein, CY5, and other dyes, digoxigenin, and the like. For biotin, a capture agent may be avidin, streptavidin, or antibodies. Antibodies may be used as capture agents for the other haptens (many dye-antibody pairs being commercially available, e.g. Molecular Probes).

Kits of the Invention

In the commercialization of the methods described herein, certain kits for construction of random arrays of the invention and for using the same for various applications are particularly useful. Kits for applications of random arrays of the invention include, but are not limited to, kits for determining the nucleotide sequence of a target polynucleotide, kits for large-scale identification of differences between reference DNA sequences and test DNA sequences, kits for profiling exons, and the like. A kit typically comprises at least one support having a surface and one or more reagents necessary or useful for constructing a random array of the invention or for carrying out an application therewith. Such reagents include, without limitation, nucleic acid primers, probes, adaptors, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In one aspect, the invention provides a kit for making a random array of concatemers of DNA fragments from a source nucleic acid comprising the following components: (i) a support having a surface; and (ii) at least one adaptor oligonucleotide for ligating to each DNA fragment and forming a DNA circle therewith, each DNA circle capable of being replicated by a rolling circle replication reaction to form a concatemer that is capable of being randomly disposed on the surface. In such kits, the surface may be a planar surface having an array of discrete spaced apart regions, wherein each discrete spaced apart region has a size equivalent to that of said concatemers. The discrete spaced apart regions may form a regular array with a nearest neighbor distance in the range of from 0.1 to 20 μm. The concatemers on the discrete spaced apart regions may have a nearest neighbor distance such that they are optically resolvable. The discrete spaced apart regions may have capture oligonucleotides attached and the adaptor oligonucleotides may each have a region complementary to the capture oligonucleotides such that the concatemers are capable of being attached to the discrete spaced apart regions by formation of complexes between the capture oligonucleotides and the complementary regions of the adaptor oligonucleotides. In some embodiments, the concatemers are randomly distributed on said discrete spaced apart regions and the nearest neighbor distance is in the range of from 0.3 to 3 µm. Such kits may further comprise (a) a terminal transferase for attaching a homopolymer tail to said DNA fragments to provide a binding site for a first end of said adaptor oligonucleotide, (b) a ligase for ligating a strand of said adaptor oligonucleotide to ends of said DNA fragment to form said DNA circle, (c) a primer for annealing to a region of the strand of said adaptor oligonucleotide, and (d) a DNA polymerase for extending the primer annealed to the strand in a rolling circle replication reaction. The above adaptor oligonucleotide may have a second end having a number of degenerate bases in the range of from 4 to 12.

In another aspect the invention provides kits for sequencing a target polynucleotide comprising the following components: (i) a support having a planar surface having an array of optically resolvable discrete spaced apart regions, wherein each discrete spaced apart region has an area of less than 1 µm$^2$; (ii) a first set of probes for hybridizing to a plurality of concatemers randomly disposed on the discrete spaced apart regions, the concatemers each containing multiple copies of a DNA fragment of the target polynucleotide; and (iii) a second set of probes for hybridizing to the plurality of concatemers such that whenever a probe from the first set hybridizes contiguously to a probe from the second set, the probes are ligated. Such kits may further include a ligase, a ligase buffer, and a hybridization buffer. In some embodiments, the discrete spaced apart regions may have capture oligonucleotides attached and the concatemers may each have a region complementary to the capture oligonucleotides such that said concatemers are capable of being attached to the discrete spaced apart regions by formation of complexes between the capture oligonucleotides and the complementary regions of said concatemers.

In still another aspect, the invention provides kits for constructing a single molecule array comprising the following components: (i) a support having a surface having reactive functionalities; and (ii) a plurality of macromolecular structures each having a unique functionality and multiple complementary functionalities, the macromolecular structures being capable of being attached randomly on the surface wherein the attachment is formed by one or more linkages formed by reaction of one or more reactive functionalities with one or more complementary functionalities; and wherein the unique functionality is capable of selectively reacting with a functionality on an analyte molecule to form the single molecule array. In some embodiments of such kits, the surface is a planar surface having an array of discrete spaced apart regions containing said reactive functionalities and wherein each discrete spaced apart region has an area less than 1 µm$^2$. In further embodiments, the discrete spaced apart regions form a regular array with a nearest neighbor distance in the range of from 0.1 to 20 µm. In further embodiments, the concatemers on the discrete spaced apart regions have a nearest neighbor distance such that they are optically resolvable. In still further embodiments, the macromolecular structures may be concatemers of one or more DNA fragments and wherein the unique functionalities are at a 3' end or a 5' end of the concatemers.

In another aspect, the invention includes kits for circularizing DNA fragments comprising the components: (a) at least one adaptor oligonucleotide for ligating to one or more DNA fragments and forming DNA circles therewith (b) a terminal transferase for attaching a homopolymer tail to said DNA fragments to provide a binding site for a first end of said adaptor oligonucleotide, (c) a ligase for ligating a strand of said adaptor oligonucleotide to ends of said DNA fragment to form said DNA circle, (d) a primer for annealing to a region of the strand of said adaptor oligonucleotide, and (e) a DNA polymerase for extending the primer annealed to the strand in a rolling circle replication reaction. In an embodiment of such kit, the above adaptor oligonucleotide may have a second end having a number of degenerate bases in the range of from 4 to 12. The above kit may further include reaction buffers for the terminal transferase, ligase, and DNA polymerase. In still another aspect, the invention includes a kit for circularizing DNA fragments using a Circligase enzyme (Epicentre Biotechnologies, Madison, Wis.), which kit comprises a volume exclusion polymer. In another aspect, such kit further includes the following components: (a) reaction buffer for controlling pH and providing an optimized salt composition for Circligase, and (b) Circligase cofactors. In another aspect, a reaction buffer for such kit comprises 0.5 M MOPS (pH 7.5), 0.1 M KCl, 50 mM MgCl$_2$, and 10 mM DTT. In another aspect, such kit includes Circligase, e.g. 10-100 µL Circligase solution (at 100 unit/mL). Exemplary volume exclusion polymers are disclosed in U.S. Pat. No. 4,886,741, which is incorporated by reference, and include polyethylene glycol, polyvinylpyrrolidone, dextran sulfate, and like polymers. In one aspect, polyethylene glycol (PEG) is 50% PEG4000. In one aspect, a kit for circle formation includes the following:

| Amount | Component | Final Conc. |
|---|---|---|
| 2 µL | Circligase 10X reaction buffer | 1X |
| 0.5 µL | 1 mM ATP | 25 µM |
| 0.5 µL | 50 mM MnCl$_2$ | 1.25 mM |
| 4 µL | 50% PEG4000 | 10% |
| 2 µL | Circligase ssDNA ligase (100 units/µL) | 10 units/µL |
| | single stranded DNA template | 0.5-10 pmol/µL |
| | sterile water | |

Final reaction volume: 20 µL. The above components are used in the following protocol:
1. Heat DNA at 60-96° C. depending on the length of the DNA (ssDNA templates that have a 5'-phosphate and a 3'-hydroxyl group).
2. Preheat 2.2× reaction mix at 60° C. for about 5-10 min.
3. If DNA was preheated to 96° C. cool it down at 60° C.
4. Mix DNA and buffer at 60° C. without cooling it down and incubate for 2-3 h.
5. Heat Inactivate enzyme to stop the ligation reaction.

Large-Scale Mutation Discovery by Mismatch Enzyme Cleavage

Arrays and sequencing methods of the invention used may be used for large-scale identification of polymorphisms using mismatch cleavage techniques. Several approaches to mutation detection employ a heteroduplex in which the mismatch itself is utilized for cleavage recognition. Chemical cleavage with piperidine at mismatches modified with hydroxylamine or osmium tetroxide provides one approach to release a cleaved fragment. In a similar way the enzymes T7 endonuclease I or T4 endonuclease VII have been used in the enzyme mismatch cleavage (EMC) techniques, e.g. Youil et al, Proc. Natl. Acad. Sci., 92: 87-91 (1995); Mashal et al, Nature Genetics, 9: 177-183 (1995); Babon et al, Molecular Biotechnology, 23: 73-81 (2003); Ellis et al, Nucleic Acids Research, 22: 2710-2711 (1994); and the like, which are incorporated herein by reference. Cleavase is used in the cleavage fragments length polymorphism (CFLP) technique which has been commercialized by Third Wave Technologies. When single stranded DNA is allowed to fold and adopt a secondary structure the DNA will form internal hairpin loops at locations dependent upon the base sequence of the strand. Cleavase will cut single stranded DNA five-prime of the loop and the fragments can then be separated by PAGE or similar size resolving techniques. Mismatch binding proteins such as Mut S and Mut Y also rely upon the formation of heteroduplexes for their ability to identify mutation sites. Mismatches are usually repaired but the binding action of the enzymes can be used for the selection of fragments through a mobility shift in gel electrophoresis or by protection from exonucleases, e.g. Ellis et al (cited above).

Templates for heteroduplex formation are prepared by primer extension from genomic DNA. For the same genomic region of the reference DNA, an excess of the opposite strand is prepared in the same way as the test DNA but in a separate reaction. The test DNA strand produced is biotinylated and is attached to a streptavidin support. Homoduplex formation is prevented by heating and removal of the complementary strand. The reference preparation is now combined with the single stranded test preparation and annealed to produce heteroduplexes. This heteroduplex is likely to contain a number of mismatches. Residual DNA is washed away before the addition of the mismatch endonuclease, which, if there is a mismatch every 1 kb would be expected to produce about 10 fragments for a 10 kb primer extension. After cleavage, each fragment can bind an adapter at each end and enter the mismatch-fragment circle selection process. Capture of mismatch cleaved DNA from Large genomic fragments. The 5-10 kb genomic fragments prepared from large genomic fragments as described above are biotinylated by the addition of a biotinylated dideoxy nucleotide at the 3-prime end with terminal transferase and excess biotinylated nucleotide are removed by filtration. A reference BAC clone that covers the same region of sequence is digested with the same six-base cutter to match the fragments generated from the test DNA. The biotinylated genomic fragments are heat denatured in the presence of the BAC reference DNA and slowly annealed to generate biotinylated heteroduplexes. The reference BAC DNA is in large excess to the genomic DNA so the majority of biotinylated products will be heteroduplexes. The biotinylated DNA can then be attached to the surface for removal of the reference DNA. Residual DNA is washed away before the addition of the mismatch endonuclease. After cleavage, each fragment can bind an adapter at each end and enter the mismatch circle selection process as follows. (a) DNA is cleaved on both sides of the mismatch. (b) 5-prime overhangs are generated that can be ligated. (3' overhangs are also created by digesting with an appropriate restriction endonuclease having a four base recognition site.) (c) An adapter is introduced that contains an active overhang at one side. (d) An adapter is ligated to each of the two generated fragments (only ligation to the right from the 5' phosphate after addition of sequences to the 3' end of the top strand). (e) The molecule is phosphorylated and a bridging oligonucleotide is used to ligate the two ends of the single stranded molecule. (f) After circularization, a concatemer is generated by extending a primer in a RCR reaction.

Circle Formation from Mismatch Cleavage Products

Figure 7:
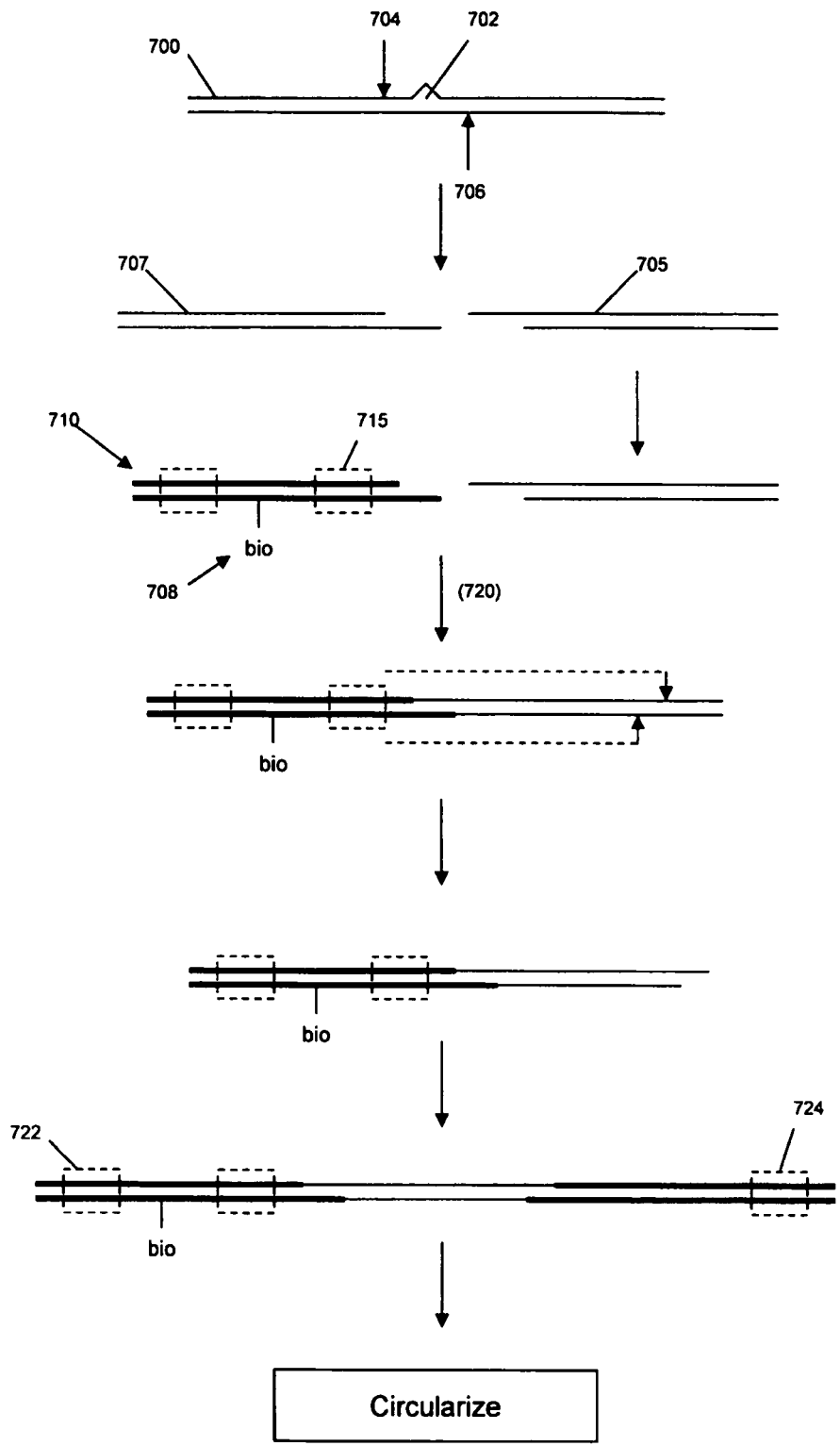
FIG. 7 is a scheme for identifying sequence differences between reference sequences and test sequences using enzymatic mismatch detection and for constructing DNA circles therefrom.
Figure 8:
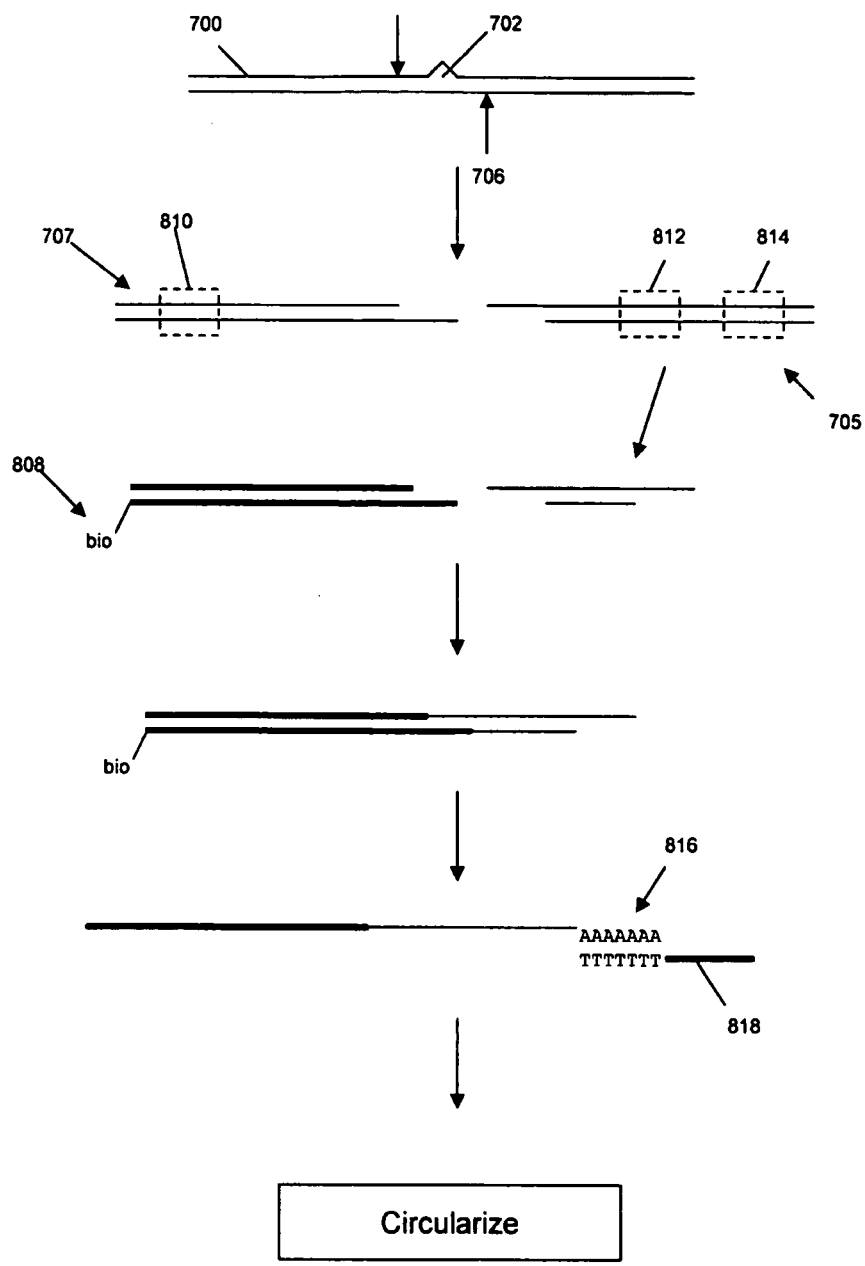
FIG. 8 is another for identifying sequence differences between a reference sequence and a test sequence using enzymatic mismatch detection and for constructing DNA circles therefrom.

Method I. The heteroduplexes generated above can be used for selection of small DNA circles, as illustrated in FIGS. 7 and 8. As shown in FIG. 7, in this process, heteroduplex (700) of a sample is treated with the mismatch enzyme to create products cleaved on both strands (704 and 706) surrounding the mutation site (702) to produce fragments (707) and (705). T7 endonuclease I or similar enzyme cleaves 5-prime of the mutation site to reveal a 5-prime overhang of varying length on both strands surrounding the mutation. The next phase is to capture the cleaved products in a form suitable for amplification and sequencing. Adapter (710) is ligated to the overhang produced by the mismatch cutting (only fragment (705) shown), but because the nature of the overhang is unknown, at least three adapters are needed and each adapter is synthesized with degenerate bases to accommodate all possible ends. The adapter can be prepared with an internal biotin (708) on the non-circularizing strand to allow capture for buffer exchange and sample cleanup, and also for direct amplification on the surface if desired.

Because the intervening sequence between mutations does not need to be sequenced and reduces the sequencing capacity of the system it is removed when studying genomic-derived samples. Reduction of sequence complexity is accomplished by a type IIs enzyme that cuts the DNA at a point away from the enzyme recognition sequence. In doing so, the cut site and resultant overhangs will be a combination of all base variants. Enzymes that can be used include MmeI (20 bases with 2 base 3' overhang) and Eco P15I (with 25 bases and 2 base 5' overhang). The adapter is about 50 bp in length to provide sequences for initiation of rolling circle amplification and also provide stuffer sequence for circle formation, as well as recognition site (715) for a type IIs restriction endonuclease. Once the adapter has been ligated to the fragment the DNA is digested (720) with the type IIs restriction enzyme to release all but 20-25 bases of sequence containing the mutation site that remains attached to the adapter.

The adaptered DNA fragment is now attached to a streptavidin support for removal of excess fragment DNA. Excess adapter that did not ligate to mismatch cleaved ends will also bind to the streptavidin solid support. The new degenerate end created by the type IIs enzyme can now be ligated to a second adapter through the phosphorylation of one strand of the second adapter. The other strand is non-phosphorylated and blocked at the 3-prime end with a dideoxy nucleotide. The structure formed is essentially the genomic fragment of interest captured between two different adapters. To create a circle from this structure would simply require both ends of the molecule coming together and ligating, e.g. via formation of staggered ends by digesting at restriction sites (722) and (724), followed by intra-molecular ligation. Although this event should happen efficiently, there is also the possibility that the end of an alternative molecule could ligate at the other end of the molecule creating a dimer molecule, or greater multiples of each unit molecule. One way to minimize this is to perform the ligation under dilute conditions so only intra-molecular ligation is favored, then re-concentrating the sample for future steps. An alternative strategy to maximize the efficiency of circle formation without inter-molecular ligation is to block excess adapters on the surface. This can be achieved by using lambda exonuclease to digest the lower strand. If second adapter has been attached then it will be protected from digestion because there is no 5-prime phosphate available. If only the first adapter is attached to the surface then the 5-prime phosphate is exposed for degradation of the lower strand of the adapter. This will lead to loss of excess first adapter from the surface.

After lambda exonuclease treatment the 5 prime end of the top strand of the first adapter is prepared for ligation to the 3-prime end of the second adapter. This can be achieved by introducing a restriction enzyme site into the adapters so that re-circularization of the molecule can occur with ligation. Amplification of DNA captured into the circular molecules proceeds by a rolling circle amplification to form long linear concatemer copies of the circle. If extension initiates 5-prime of the biotin, the circle and newly synthesized strand is released into solution. Complementary oligonucleotides on the surface are responsible for condensation and provide sufficient attachment for downstream applications. One strand is a closed circle and acts as the template. The other strand, with an exposed 3-prime end, acts as an initiating primer and is extended.

Method II. This method, illustrated in FIG. 8, is similar to the procedure above with the following modifications. 1) The adapter can be prepared with a 3-prime biotin (808) on the non-circularized strand to allow capture for buffer exchange and sample cleanup. 2) Reduction of sequence complexity of the 10 kb heteroduplex fragments described above occurs through the use of 4-base cutting restriction enzymes, e.g. with restriction sites (810), (812), and (814). Use of 2 or 3 enzymes in the one reaction could reduce the genomic fragment size down to about 100 bases. The adapter-DNA fragment can be attached to a streptavidin support for removal of excess fragment DNA. Excess adapter that did not ligate to mismatch cleaved ends will also bind to the streptavidin solid support. The biotinylated and phosphorylated strand can now be removed by lambda exonuclease which will degrade from the 5-prime end but leave the non-phosphorylated strand intact. To create a circle from this structure now requires both ends of the molecule coming together and ligating to form the circle. Several approaches are available to form the circle using a bridging oligonucleotide, as described above. A polynucleotide can be added to the 3-prime end with terminal transferase to create a sequence for one half of a bridge oligonucleotide (818) to hybridize to, shown as polyA tail (816). The other half will bind to sequences in the adapter. Alternatively, before addition of the exonuclease, an adapter can be added to the end generated by the 4-base cutter which will provide sequence for the bridge to hybridize to after removal of one strand by exonuclease. A key aspect of this selection procedure is the ability to select the strand for circularization and amplification. This ensures that only the strand with the original mutation (from the 5-prime overhang) and not the strand from the adapter is amplified. If the 3-prime recessed strand was amplified then a mismatch from the adapter could create a false base call at the site of or near to the mutation. Amplification of DNA captured into the circular molecules proceeds by a rolling circle amplification to form linear concatemer copies of the circle.

Alternative applications of mis-match derived circles. The mis-match derived small circular DNA molecules may be amplified by other means such as PCR. Common primer binding sites can be incorporated into the adapter sequences The amplified material can be used for mutation detection by methods such as Sanger sequencing or array based sequencing. Cell-free clonal selection of cDNAs. Traditional methods of cloning have several drawbacks including the propensity of bacteria to exclude sequences from plasmid replication and the time consuming and reagent-intensive protocols required to generate clones of individual cDNA molecules. Linear single-stranded can be made from amplifications of DNA molecules that have been closed into a circular form. These large concatemeric, linear forms arise from a single molecule and can act as efficient, isolated targets for PCR when separated into a single reaction chamber, in much the same way a bacterial colony is picked to retrieve the cDNA containing plasmid. We plan to develop this approach as a means to select cDNA clones without having to pass through a cell-based clonal selection step. The first step of this procedure will involve ligating a gene specific oligonucleotide directed to the 5-prime end with a poly dA sequence for binding to the poly dT sequence of the 3-prime end of the cDNA. This oligonucleotide acts as a bridge to allow T4 DNA ligase to ligate the two ends and form a circle.

The second step of the reaction is to use a primer, or the bridging oligonucleotide, for a strand displacing polymerase such as Phi 29 polymerase to create a concatemer of the circle. The long linear molecules will then be diluted and arrayed in 1536 well plates such that wells with single molecules can be selected. To ensure about 10% of the wells contain 1 molecule approximately 90% would have to be sacrificed as having no molecules. To detect the wells that are positive a dendrimer that recognizes a universal sequence in the target is hybridized to generate 10K-100K dye molecules per molecule of target. Excess dendrimer is removed through hybridization to biotinylated capture oligos. The wells are analyzed with a fluorescent plate reader and the presence of DNA scored. Positive wells are then re-arrayed to consolidate the clones into plates with complete wells for further amplification Splice Variant Detection and Exon Profiling The process described is based on random DNA arrays and "smart" probe pools for the identification and quantification of expression levels of thousands of genes and their splice variants. In eukaryotes, as the primary transcript emerges from the transcription complex, spliceosomes interact with splice sites on the primary transcript to excise out the introns, e.g. Maniatis et al, Nature, 418: 236-243 (2002). However, because of either mutations that alter the splice site sequences, or external factors that affect spliceosome interaction with splice sites, alternative splice sites, or cryptic splice sites, could be selected resulting in expression of protein variants encoded by mRNA with different sets of exons. Surveys of cDNA sequences from large scale EST sequencing projects indicated that over 50% of the genes have known splice variants. In a recent study using a microarray-based approach, it was estimated that as high as 75% of genes are alternatively spliced, e.g. Johnson et al, Science, 302: 2141-2144 (2003).

The diversity of proteins generated through alternative splicing could partially contribute to the complexity of biological processes in higher eukaryotes. This also leads to the implication that the aberrant expression of variant protein forms could be responsible for pathogenesis of diseases. Indeed, alternative splicing has been found to associate with various diseases like growth hormone deficiency, Parkinson's disease, cystic fibrosis and myotonic dystrophy, e.g. Garcia-Blanco et al, Nature Biotechnology, 22: 535-546 (2004). Because of the difficulty in isolating and characterizing novel splice variants, the evidence implicating roles of splice variants in cancer could represent the tip of the iceberg. With the availability of tools that could rapidly and reliably characterize splicing patterns of mRNA, it would help to elucidate the role of alternative splicing in cancer and in disease development in general.

In one aspect, methods of the invention permit large-scale measurement of splice variants with the following steps: (a) Prepare full length first strand cDNA for targeted or all mRNAs. (b) Circularize the generated full length (or all) first strand cDNA molecules by incorporating an adapter sequence. (c) By using primer complementary to the adapter sequence perform rolling circle replication (RCR) of cDNA circles to form concatemers with over 100 copies of initial cDNA. (d) Prepare random arrays by attaching RCR produced "cDNA balls" to glass surface coated with capture oligonucleotide complementary to a portion of the adapter sequence; with an advanced submicron patterned surface one $mm^2$ can have between 1-10 million cDNA spots; note that the attachment is a molecular process and does not require robotic spotting of individual "cDNA balls" or concatemers. (e) Starting from pre-made universal libraries of 4096 6-mers and 1024 labeled 5-mers, use a sophisticated computer program and a simple robotic pipettor to create 40-80 pools of about 200 6-mers and 20 5-mers for testing all 10,000 or more exons in targeted 1000 or more up to all known genes in the sample organism/tissue. (f) In a 4-8 hour process, hybridize/ligate all probe pools in 40-80 cycles on the same random array using an automated microscope-like instrument with a sensitive 10-mega pixel CCD detector for generating an array image for each cycle. (g) Use a computer program to perform spot signal intensity analysis to identify which cDNA is on which spot, and if any of the expected exons is missing in any of the analyzed genes. Obtain exact expression levels for each splice variant by counting occurrences in the array.

This system provides a complete analysis of the exon pattern on a single transcript, instead of merely providing information on the ratios of exon usage or quantification of splicing events over the entire population of transcribed genes using the current expression arrays hybridized with labeled mRNA/cDNA. At the maximum limit of its sensitivity, it allows a detailed analysis down to a single molecule of a mRNA type present in only one in hundreds of other cells; this would provide unique potentials for early diagnosis of cancer cells. The combination of selective cDNA preparation with an "array of random arrays" in a standard 384-well format and with "smart" pools of universal short probes provides great flexibility in designing assays; for examples, deep analysis of a small number of genes in selected samples, or more general analysis in a larger number of samples, or analysis of a large number of genes in smaller number of samples. The analysis provides simultaneously 1) detection of each specific splice variant, 2) quantification of expression of wild type and alternatively spliced mRNAs. It can also be used to monitor gross chromosomal alterations based on the detection of gene deletions and gene translocations by loss of heterozygosity and presence of two sub-sets of exons from two genes in the same transcript on a single spot on the random array. The exceptional capacity and informativeness of this assay is coupled with simple sample preparation from very small quantities of mRNA, fully-automated assay based on all pre-made, validated reagents including libraries of universal labeled and unlabeled probes and primers/adapters that will be ultimately developed for all human and model organism genes. The proposed splice variant profiling process is equivalent to high throughput sequencing of individual full length cDNA clones; rSBH throughput can reach one billion cDNA molecules profiled in a 4-8 hour assay. This system will provide a powerful tool to monitor changes in expression levels of various splice variants during disease emergence and progression. It can enable discovery of novel splice variants or validate known splice variants to serve as biomarkers to monitor cancer progression. It can also provide means to further understanding the roles of alternative splice variants and their possible uses as therapeutic targets. Universal nature and flexibility of this low cost and high throughput assay provides great commercial opportunities for cancer research and diagnostics and in all other biomedical areas. This high capacity system is ideal for service providing labs or companies.

Preparation of Templates for In Vitro Transcription. Exon Sequences are Cloned into the multiple cloning sites (MCS) of plasmid pBluescript, or like vector. For the purposes of demonstrating the usefulness of the probe pools, it is not necessary to clone the contiguous full-length sequence, nor to maintain the proper protein coding frame. For genes that are shorter than 1 kb, PCR products are generated from cDNA using gene specific oligos for the full length sequence. For longer genes, PCR products are generated comprising about 500 bp that corresponding to contiguous block of exons and ordered the fragments by cloning into appropriate cloning sites in the MCS of pBluescript. This is also the approach for cloning the alternative spliced versions, since the desired variant might not be present in the cDNA source used for PCR.

The last site of the MCS is used to insert a string of 40 A's to simulate the polyA tails of cellular mRNA. This is to control for the possibility that the polyA tail might interfere with the sample preparation step described below, although it is not expected to be a problem since a poly-dA tail is incorporated in sample preparation of genomic fragments as described. T7 RNA polymerase will be used to generate the run-off transcripts and the RNA generated will be purified with the standard methods.

Preparation of Samples for Arraying. Because the Probe Pools are Designed for Specific genes, cDNA is prepared for those specific genes only. For priming the reverse transcription reactions, gene-specific primers are used, therefore for 1000 genes, 1000 primers are used. The location of the priming site for the reverse transcription is selected with care, since it is not reasonable to expect the synthesis of cDNA >2 kb to be of high efficiency. It is quite common that the last exon would consist of the end of the coding sequence and a long 3' untranslated region. In the case of CD44 for example, although the full-length mRNA is about 5.7 kb, the 3' UTR comprises of 3 kb, while the coding region is only 2.2 kb. Therefore the logical location of the reverse transcription primer site is usually immediately downstream of the end of the coding sequence. For some splice variants, the alternative exons are often clustered together as a block to create a region of variability. In the case of Tenascin C variants (8.5 kb), the most common isoform has a block of 8 extra exons, and there is evidence to suggest that there is variability in exon usage in that region. So for Tenascin C, the primer will be located just downstream of that region. Because of the concern of synthesizing cDNA with length >2 kb, for long genes, it might be necessary to divide the exons into blocks of 2 kb with multiple primers.

Reverse transcription reactions may be carried out with commercial systems, e.g. SuperScript III system from Invitrogen (Carlsbad, Calif.) and the StrataScript system from Stratagene (La Jolla, Calif.). Once single stranded cDNA molecules are produced, the rest of the procedures involved putting on the adaptor sequence, circularization of the molecule and RCR as described above. The 5' ends of the cDNAs are basically the incorporated gene-specific primers used for initiating the reverse transcription. By incorporating a 7 base universal tag on the 5' end of the reverse-transcription priming oligos, all the cDNA generated will carry the same 7 base sequence at the 5' end. Thus a single template oligonucleotide that is complementary to both the adaptor sequence and the universal tag can be used to ligate the adaptor to all the target molecules, without using the template oligonucleotide with degenerate bases. As for the 3' end of the cDNA (5' end of the mRNA) which is usually ill-defined, it may be treated like a random sequence end of a genomic fragment. Similar methods of adding a polyA tail will be applied, thus the same circle closing reaction may also be used.

Reverse transcriptases are prone to terminate prematurely to create truncated cDNAs. Severely truncated cDNAs probably will not have enough probe binding sites to be identified with a gene assignment, thus would not be analyzed. cDNA molecules that are close, but not quite full-length, may show up as splice variant with missing 5' exons. If there are no corroborating evidence from a sequence database to support such variants, they may be discounted. A way to avoid such problem is to select for only the full-length cDNA (or those with the desired 3' end) to be compatible with circle closing reaction, then any truncated molecules will not be circularized nor replicated. First a dideoxy-cytosine residue can be added to the 3' end of all the cDNA to block ligation, then by using a mismatch oligo targeting the desired sequence, a new 3' end can be generated by enzyme mismatch cleavage using T4 endonuclease VII. With the new 3' end, the cDNA can proceed with the adding a poly-dA tail and with the standard protocols of circularization and replication.

Replicated and arrayed concatemers of the exon fragments may be carried out using combinatorial SBH, as described above. The algorithm of the following steps may be used to select 5-mer and 6-mer probes for use in the technique:

Step 1: Select 1000-2000 shortest exons (total about 20-50 kb), and find out matching sequences for each of 1024 available labeled 5-mers. On average each 5-mer will occur 20 times over 20 kb, but some may occur over 50 or over 100 times. By selecting the most frequent 5-mer, the largest number of short exons will be detected with the single labeled probe. A goal would be to detect about 50-100 short exons (10%-20% of 500 exons) per cycle. Thus less than 10 labeled probes and 50-100 unlabeled 6-mers would be sufficient. Small number of labeled probes is favorable because it minimizes overall fluorescent background.

Step 2. Find out all 6-mers that are contiguous with all sites in all 1000 genes that are complementary to 10 selected 5-mers. On average 20 such sites will exist in each 2 kb gene. Total number of sites would be about 20,000, e.g., each 6-mer on average will occur 5 times. Sort 6-mers by the hit frequency. The most frequent may have over 20 hits, e.g. such 6-mer will detect 20 genes through combinations with 10 labeled probes. Thus, to get a single probe pair for each of the 500 genes a minimum of 25 6-mer probes would be required. Realistically, 100 to 200 6-mers may be required.

Due to benefits of combinatorial SBH that uses pre-made libraries of 6-mer and 5-mer probes 40 probe pools are readily prepared with about 200 probes per pool using established pipetting robotics. The information generated is equivalent to having over 3 probes per exon, therefore the use of 8000 5-mers and 6-mers effectively replaces the 30,000 longer exons specific probes required for a single set of 1000 genes.

Exon profiling. The profiling of exons can be performed in two phases: the gene identification phase and the exon identification phase. In the gene identification phase, each concatemer on the array can be uniquely identified with a particular gene. In theory, 10 probe pools or hybridization cycles will be enough to identify 1000 genes using the following scheme. Each gene is assigned a unique binary code. The number of binary digits thus depends on the total number of genes: 3 digits for 8 genes, 10 digits for 1024 genes. Each probe pool is designed to correspond to a digit of the binary code and would contain probes that would hit a unique combination of half of the genes and one hit per gene only. Thus for each hybridization cycle, an unique half of the genes will score a 1 for that digit and the other half will score zero. Ten hybridization cycles with 10 probe pools will generate 1024 unique binary codes, enough to assign 1000 unique genes to all the concatemers on the array. To provide redundancy in the identification data, 15-20 cycles would be used. If 20 cycles are used, it would provide 1 million unique binary codes and there should be enough information to account for loss of signals due to missing exons or gene deletions. It will also be equivalent to having 10 data points per gene (20 cycles of 500 data point each give 10,000 data points total), or one positive probe-pair per exon, on average. At this point after 20 cycles, this system is capable of making assignment of 1 million unique gene identities to the ampliots. Therefore by counting gene identities of the ampliots, one can determine quantitatively the expression level of all the genes (but not sub-typing of splice variants) in any given samples.

After identifying each ampliot with a gene assignment, its exon pattern will be profiled in the exon identification phase. For the exon identification phase, one exon per gene in all or most of the genes is tested per hybridization cycle. In most cases 10-20 exon identification cycles should be sufficient. Thus, in the case of using 20 exon identification cycles we will obtain information of 2 probes per each of 10 exons in each gene. For genes with more than 20 exons, methods can be developed so that 2 exons per gene can be probed at the same cycle. One possibility is using multiple fluorophores of different colors, and another possibility is to exploit differential hybrid stabilities of different ligation probe pairs.

In conclusion, a total of about 40 assay cycles will provide sufficient information to obtain gene identity at each spot and to provide three matching probe-pairs for each of 10,000 exons with enough informational redundancy to provide accurate identification of missing exons due to alternative splicing or chromosomal deletions.

EXAMPLE 1

Glass Cover Slip as Random Array Support: Derivatization Protocol

In this example, a glass cover slip is prepared for use as a support for disposing DNA concatemers. The following materials are used:

Millipore DI water
2.5 ml of 3-Aminopropyldimethylethoxysilane (Gelest)
1.6 grams p-phenylenediisothiocyanate (Acros Organics/fisher)
210 grams KOH (VWR)
Ethanol (VWR)
Methanol (VWR)
Pyridine (VWR)
N,N-dimethylformamide (VWR)
Acetone (VWR)
Equipment
100 c oven
magnetic stir plate
1 2"×0.5" magnetic stir bar
2 4 liter Nunc beaker
7 4"×8"×4" glass containers
1 liter graduated cylinder
1 100 ml graduated cylinder
1 lab scale
1 Metzler scale
1 large weigh boat
1 small weigh boat
1 pair thick nitrile gloves
1 large funnel
1 ml pipettman with filter tips
1 nalgene stir bar
1 airtight container (tupperware)

Using the large graduated cylinder measure 950 ml of ethanol, add to the 4 liter Nunc beaker. Measure 50 ml of DI water in the small graduated cylinder and add to the same nunc beaker. Measure out 210 grams of KOH pellets in a weigh boat on the lab scale. Add stir bar and KOH pellets to the beaker. Place beaker on stir plate and stir at low speed until KOH is completely dissolved. While KOH is dissolving, lay out 6 pre-washed glass containers. fill containers 2-5 with DI water until ½ inch from top (~800 ml). Fill container 6 with acetone ½" to top. Carefully pour dissolved KOH solution into container 1 until ½" to top. Add racked cover slips to container 1 wait 3 minutes, remove racks from container 1 and wash in containers 2-5 leaving racks in each container a minimum of 15 seconds. Submerse racks briefly in container 6. Set aside racks, dispose the solutions from containers 1 and 2 in the basic waste container using the large funnel and thick nitrile gloves, clean and dry labware. Lay out 7 clean and dry glass containers. Add 775 ml of acetone to container 1 add 2.5 ml of DI water to container 1. stir container 1 with pipette tip for 20 seconds. With a new pipette tip add 2.5 ml of 3-aminopropyldimethylethoxysilane to container 1. Stir with pipette tip for 10 seconds. Immerse all 5 racks of cover slips into container 1. Cover container 1 with polypropylene box top. Wait 45 minutes. 15 minutes prior to the completion of the reaction, fill containers 2-4 until ½" to top with acetone, fill container 5 with water ½" to top. Fill container 6 until ½" to top with acetone. Upon reaction completion (45 minutes) transfer cover slip racks 1-5 from container 1 to container 2, wait 15 seconds. Repeat this though container 6. Place racks into empty container 7 and put in 100 c oven. Wait one hour. Lay out 7 glass containers. After racks come out of oven, use the Meltzer scale to weigh out 1.6 grams of p-phenylenediisothiocyanate (PDC) in the small weigh boat. Pour 720 ml dimethylformamide into the cleaned 1 liter graduated cylinder, fill to 800 ml with pyridine. Pour 50% this solution into a clean class container then pour it back into the cylinder to mix (repeat once). Fill container 1 until ½" to top with this solution. Add the PDC from the weigh boat to container 1. Use stir bar to mix solution. Crush PDC clumps that refuse to dissolve, then stir again. Cover slip racks should be cool by now. Place all 5 racks into container one. Cover with polypropylene box top. Wait 2 hours. 10 minutes prior to reaction completion fill containers 2 and 3 with methanol until ½" from top. Fill containers 4 and 5 with acetone until ½" from top. Fill container 6 with 65% acetone 35% water until ½" from top. Fill container 7 with acetone. Successively transfer racks through all containers, waiting 15 seconds between each transfer. Remove racks from container 7 dump contents of containers 1-7 into organic waste drum. Replace racks to container 7 and dry in oven for 15 minutes. Place dry racks into airtight container, they are now ready for attachment.

EXAMPLE 2

Preparation of RCR Products form E. coli Genomic DNA and Disposition onto a Glass Cover Slip E. coli genomic DNA (32 ug) (Sigma Chemical Co) was fragmented with 0.16 U of DnaseI (Epicentre) at 37° C. for 10 min and then heat inactivated at 95° C. for 10 min. Reaction products were distributed with an average size of 200 bp as determined by agarose gel electrophoresis. If reaction products did not meet the required size distribution they were further digested with the addition of fresh enzyme. The final concentration was 200 ng/ul of genomic DNA.

The Dnase digested DNA (26 ng/ul) was reacted with Terminal deoxynucleotide transferase (0.66 U/ul) from New England Biolabs (NEB) in reaction buffer supplied by NEB. The reaction contained DATP (2 mM) and was performed at 37 C for 30 min and then heat inactivated at 70 C for 10 min. The DNA sample was then heated to 95 C for 5 min before rapid cooling on ice.

A synthetic DNA adapter was then ligated to the 5' end of the genomic DNA by first forming a hybrid of a 65-base oligonucleotide (TATCATCTACTGCACTGACCGGATGT-TAGGAAGACAAAAGGAAGCTGAGGGTCACAT TAACGGAC) (SEQ ID NO: 8) with a second oligonucleotide (NNNNNNNGTCCGTTAATGTGAC 3'2'3'ddC) (SEQ ID NO: 9) at the 3' end of the 65mer in which the 7 "Ns" form an overhang. The shorter oligo will act as a splint for ligation of the 65mer to the 5' end of the genomic fragments. The splint molecule consists of 7 degenerate bases at its 5' end to hybridize to variable bases at the 5' end of the genomic DNA. The adapter hybrid was formed by slowly hybridizing 1200 pmol of adapter with 1200 pmol of splint in 52 ul from 95 C to room temperature over 1 hr.

T4 DNA Ligase (0.3 U/ul) was combined with genomic DNA (17 ng/ul) and adapter-splint (0.5 uM) in 1× ligase reaction buffer supplied by NEB. The ligation proceeded at 15 C for 30 min, 20 C for 30 min and then inactivated at 70 C for 10 min. A second splint molecule and the mix was supplemented with more ligase buffer and T4 DNA ligase (0.3 U/ul). The reaction proceeded at 15 C for 30 min and then at 20 C for 30 min before inactivation for 10 min at 70 C.

The ligation mix was then treated with exonuclease I (NEB) (1 U/ul) at 37 C for 60 min, followed by inactivation at 80 C for 20 min Rolling circle replication was performed in reaction buffer supplied by NEB with BSA (0.1 ug/ul), 0.2 mM each dNTP, an initiating primer (TCAGCTTCCTTTTGTCTTCCTAAC) (SEQ ID NO: 11) at 2 fmol/ul, exonuclease treated ligation of genomic DNA at 24 pg/ul, and Phi 29 polymerase (0.2 U/ul). The reaction was performed for 1 hr at 30 C and then heat inactivated at 70 C for 10 min.

RCR reaction products were attached to the surface of cover slips by first attaching amine modified oligonucleotides to the surface of the cover slips. A capture probe ([AMI-NOC6][SP-C18][SP-C18]GGATGTTAGGAAGA-CAAAAGGAAGCTGAGG) (SEQ ID NO: 12) (50 uM) was added to the DITC derivatized cover slips in 0.1 uM NaHCO3 and allowed to dry at 40 C for about 30 min. The cover slips were rinsed in DDI water for 15 min and dried. RCR reaction products (4.5 ul) were then combined with 0.5 ul of 20×SSPE and added to the center of the slide. The sample was allowed to air dry and non-attached material was washed off for 10 min in 3×SSPE and then briefly in DDI water. The slide was then dried before assembly on the microscope. Attached RCR products were visualized by hybridizing an 11 mer TAMRA labeled probe that is complementary to a region of the adapter RCR reaction products were formed from a single stranded 80mer synthetic DNA target (NNNNNNNNGCATANCAC-GANGTCATNATCGTNCAAACGTCAGTC-CANGAATCNAGA TCCACTTAGAN-TAAAAAAAAAAAA) (SEQ ID NO: 13) as above but without poly A addition with TDT. The RCR reaction contained target molecules at an estimated 12.6 fmol/ul. Reaction products (5 ul) were combined with SSPE (2×) and SDS (0.3%) in a total reaction volume of 20 ul. The sample was applied to a cover-slip in which lines of capture probe ([AMI-NOC6][SP-C18][SP-C18]GGATGTTAGGAAGA- CAAAAGGAAGCTGAGG) (SEQ ID NO: 12), deposited in a solution of 50 uM with 0.1 uM NaHCO3, were dried onto the surface and left in a humid chamber for 30 min. The solution was then washed off in 3×SSPE for 10 min and then briefly in water.

Various reaction components were tested for their effect upon RCR product formation. The addition of Phi 29 to the RCR reaction at a final concentration of 0.1 U/ul rather than 0.2 U/ul was found to create a greater proportion of RCR products that were of larger intensity after detection probe hybridization. The addition of initiating primer at 10 to 100 fold molar ratio relative to estimated target concentration was also found to be optimal. Increased extension times produced more intense fluorescent signals but tended to produce more diffuse concatemers. With the current attachment protocols a 2 hr extension time produced enhanced signals relative to a 1 hr incubation with minimal detrimental impact upon RCR product morphology.

Figure 3:
FIG. 3 is an image of a glass surface containing a disposition of concatemers of E. coli fragments.
Figure 4:
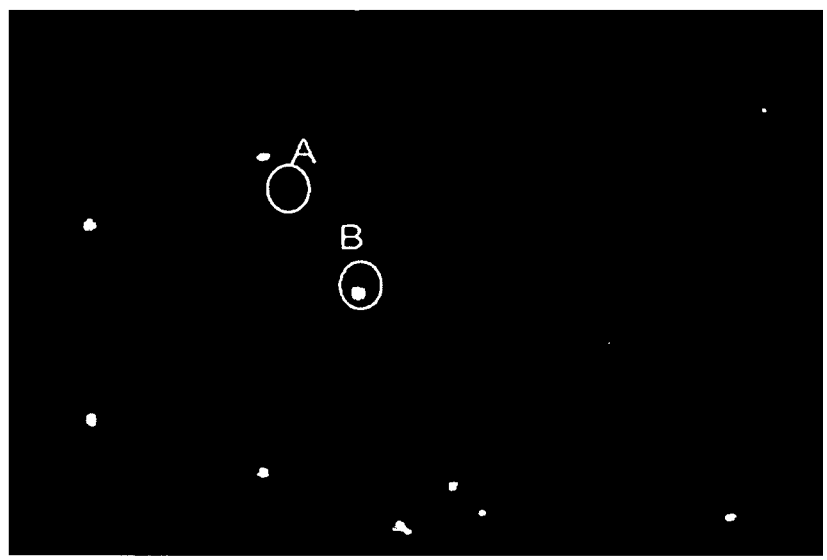
FIG. 4 is an image of concatemers derived from two different organisms that are selectively labeled using oligonucleotide probes.

Further optimization of RCR products have been achieved by reducing the estimated concentration of synthetic and genomic targets to 0.1 to 0.25 fmol/ul in the RCR reaction. This typically results in distinct and unique RCR products on the surface of the microscope slide using method 1 for attachment. For synthetic targets in which a higher concentration of targets in the RCR reaction may be present (e.g. >5 fmol/ul), RCR products may be attached by method 2. Attachment method 1. RCR reaction products (4.5 ul) were combined with 0.5 ul of 20×SSPE and added to the center of the slide. The sample was allowed to air dry and non-attached material was washed off for 10 min in 3×SSPE and then briefly in DDI water. The slide was then dried before assembly on the microscope. Attached RCR products were visualized by hybridizing an 11mer TAMRA labeled probe that is complementary to a region of the adapter. Attachment method 2. RCR reaction products (1 ul) were combined with 50 ul of 3×SSPE and added to the center of the cover slip with capture probe attached. Addition of SDS (0.3%) was found to promote specific attachment to the capture probes and not to the derivatized surface. The sample was incubated at room temperature for 30 min and non-attached material was washed off for 10 min in 3×SSPE and then briefly in DDI water. The slide was then dried before assembly on the microscope. Attached RCR products were visualized by hybridizing an 11mer TAMRA labeled probe that is complementary to a region of the adapter. The above protocols provide RCR product densities of about 1 RCR product per 2-4 micron square. Exemplary image of a resulting cover slip is shown in FIG. 3.

EXAMPLE 3

Distinguish RCR Products on Random Arrays Using Fluorescently Labeled Probes PCR products from diagnostic regions of *Bacillus anthracis* and *Yersinia pestis* were converted into single stranded DNA and attached to a universal adaptor. These two samples were then mixed and replicated together using RCR and deposited onto a glass surface as a random array. Successive hybridization with amplicon specific probes showed that each spot on the array corresponded uniquely to either one of the two sequences and that they can be identified specifically with the probes, as illustrated in FIG. 4. This result demonstrates sensitivity and specificity of identifying DNA present in submicron sized DNA concatemers having about 100-1000 copies of a DNA fragment generated by the RCR reaction. A 155 bp amplicon sequence from *B. anthracis* and a 275 bp amplicon sequence from *Y. pestis* were amplified using standard PCR techniques with PCR primers in which one primer of the pair was phosphorylated. A single stranded form of the PCR products was generated by degradation of the phosphorylated strand using lambda exonuclease. The 5' end of the remaining strand was then phosphorylated using T4 DNA polynucleotide kinase to allow ligation of the single stranded product to the universal adaptor. The universal adaptor was ligated using T4 DNA ligase to the 5' end of the target molecule, assisted by a template oligonucleotide complementary to the 5' end of the targets and 3' end of the universal adaptor. The adaptor ligated targets were then circularized using bridging oligonucleotides with bases complementary to the adaptor and to the 3' end of the targets. Linear DNA molecules were removed by treating with exonuclease I. RCR products (DNA concatemers) were generated by mixing the single-stranded samples and using Phi29 polymerase to replicate around the circularized adaptor-target molecules with the bridging oligonucleotides as the initiating primers.

To prepare the cover slips for attaching amine-modified oligonucleotides, the cover slips were first cleaned in a potassium/ethanol solution followed by rinsing and drying. They were then treated with a solution of 3-aminopropyldimethylethoxysilane, acetone, and water for 45 minutes and cured in an oven at 100° C. for 1 hour. As a final step, the cover slips were treated with a solution of p-phenylenediisothiocyanate (PDC), pyridine, and dimethylformamide for 2 hours. The capture oligonucleotide (sequence 5'-GGATGTTAGGAAGACAAAAGGAAGCTGAGG-3') (SEQ ID NO: 14) is complementary to the universal adaptor sequence. and is modified at the 5' end with an amine group and 2 C-18 linkers. For attachment, 10 μl of the capture oligo at 10 μM in 0.1M $NaHCO_3$ was spotted onto the center of the derivatized cover slip, dried for 10 minutes in a 70° C. oven and rinsed with water. To create an array of DNA concatemers, the RCR reaction containing the DNA concatemers was diluted 10-folds with 3×SSPE, 20 μl of which was then deposited over the immobilized capture oligonucleotides on the cover slip surface for 30 minutes in a moisture saturated chamber. The cover slip with the DNA concatemers was then assembled into a reaction chamber and was rinsed by 2 ml of 3×SSPE. Arrayed target concatemer molecules derived from *B. anthracis* and *Y. pestis* PCR amplicons were probed sequentially with TAMRA-labeled oligomer: probe BrPrb3 (sequence: 5'-CATTAACGGAC-3' (SEQ ID NO: 15), specifically complementary to the universal adaptor sequence), probe Ba3 (sequence: 5'-TGAGCGATTCG-3' (SEQ ID NO: 16), specifically complementary to the Ba3 amplicon sequence), probe Yp3 (sequence: 5'-GGTGTCATGGA-3' (SEQ ID NO: 18), specifically complementary to the Yp3 amplicon sequence). The probes were hybridized to the array at a concentration of 0.1 μM for 20 min in 3×SSPE at room temperature. Excess probes were washed off with 2 ml of 3×SSPE. Images were taken with the TIRF microscope. The probes were then stripped off with 1 ml of 3×SSPE at 80° C. for 5 minutes to prepare the arrayed target molecules for the next round of hybridization.

By overlaying the images obtained from successive hybridization of 3 probes, as shown in FIG. 4, it can be seen that most of the arrayed molecules that hybridized with the adaptor probe would only hybridize to either the amplicon 1 probe (e.g. "A" in FIG. 4) or the amplicon 2 probe (e.g. "B" in FIG. 4), with very few that would hybridize to both. This specific hybridization pattern demonstrates that each spot on the array contains only one type of sequence, either the *B anthracis* amplicon or the *Y. pestis* amplicon.

EXAMPLE 4

Figure 5:
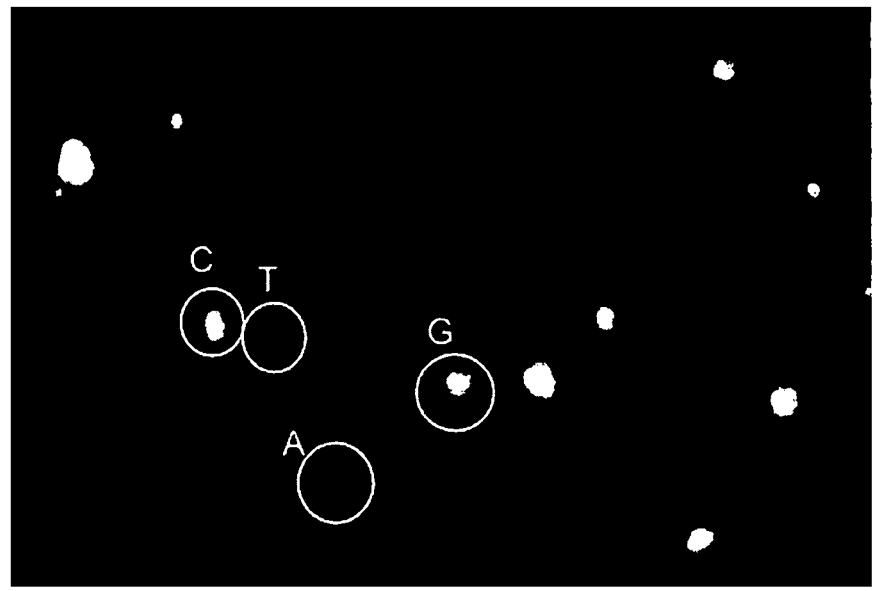
FIG. 5 is an image of concatemers of DNA fragments that contain a degenerated base, each of which is identified by a specific ligation probe.

Decoding a Base Position in Arrayed Concatemers Created from a Synthetic 80-Mer Oligonucleotide Containing a Degenerated Base Individual molecules of a synthetic oligonucleotide containing a degenerate base can be divided into 4 sub-populations, each may have either an A, C, G or T base at that particular position. An array of concatemers created from this synthetic DNA may have about 25% of spots with each of the bases. Successful identification of these sub-populations of concatemers was demonstrated by four successive hybridization and ligation of pairs of probes, specific to each of the 4 bases, as shown in FIG. 5. A 5' phosphorylated, 3' TAMRA-labeled pentamer oligonucleotide was paired with one of the four hexamer oligonucleotides. Each of these 4 ligation probe pairs should hybridize to either an A, C, G or T containing version of the target. Discrimination scores of greater than 3 were obtained for most targets, demonstrating the ability to identify single base differences between the nanoball targets. The discrimination score is the highest spot score divided by the average of the other 3 base-specific signals of the same spot. By adjusting the assay conditions (buffer composition, concentrations of all components, time and temperature of each step in the cycle) higher signal to background and full match to mismatch ratios are expected. This was demonstrated with a similar ligation assay performed on the spotted arrays of 6-mer probes. In this case full-match/background ratio was about 50 and the average full match/mismatch ratio was 30. The results further demonstrate the ability to determine partial or complete sequences of DNA present in concatemers by increasing the number of consecutive probe cycles or by using 4 or more probes labeled with different dyes per each cycle. Synthetic oligonucleotide (T1A: 5'-NNNNNNNNGCATANCACGANGTCAT-NATCGTNCAAACGTCAGTCCANGAATCNAGAT CCACTTAGANTAAAAAAAAAAAAA-3') (SEQ ID NO: 13) contains at position 32 a degenerate base. Universal adaptor was ligated to this oligonucleotide and the adaptor-T1A DNA was circularized as described before. DNA concatemers made using the rolling circle replication (RCR) reaction on this target were arrayed onto the random array. Because each spot on this random array corresponded to tandemly replicated copies originated from a single molecule of T1A, therefore DNA in a particular arrayed spot would contain either an A, or a C, or a G, or a T at positions corresponding to position 32 of T1A. To identify these sub-populations, a set of 4 ligation probes specific to each of the 4 bases was used. A 5' phosphorylated, 3' TAMRA-labeled pentamer oligonucleotide corresponding to position 33-37 of T1A with sequence CAAAC (probe T1A9b) was paired with one of the following hexamer oligonucleotides corresponding to position 27-32: ACTGTA (probe T1A9a), ACTGTC (probe T1A10a), ACTGTG (probe T1A11a), ACTGTT (probe T1A12a). Each of these 4 ligation probe pairs should hybridize to either an A, C, G or T containing version of T1A. For each hybridization cycle, the probes were incubated with the array in a ligation/hybridization buffer containing T4 DNA ligase at 20° C. for 5 minutes. Excess probes were washed off at 20° C. and images were taken with a TIRF microscope. Bound probes were stripped to prepare for the next round of hybridization.

An adaptor specific probe (BrPrb3) was hybridized to the array to establish the positions of all the spots. The 4 ligation probe pairs, at 0.4 µM, were then hybridized successively to the array with the base identifications as illustrated for four spots in FIG. 5. It is clear that most of the spots are associated with only one of the 4 ligation probe pairs, and thus the nature of the base at position 32 of T1A can be determined specifically.

EXAMPLE 5

Decoding Two Degenerate Bases at the End of a Synthetic 80-Mer Oligonucleotide The same synthetic oligonucleotide described above contains 8 degenerate bases at the 5' end to simulate random genomic DNA ends. The concatemers created from this oligonucleotide may have these 8 degenerate bases placed directly next to the adaptor sequence. To demonstrate the feasibility of sequencing the two unknown bases adjacent to the known adaptor sequence, a 12-mer oligonucleotide (UK0-12 sequence 5'-ACATTAACGGAC-3') (SEQ ID NO: 17) with a specific sequence to hybridize to the 3' end of the adaptor sequence was used as the anchor, and a set of 16 TAMRA-labeled oligonucleotides in the form of BBNNNNNN were used as the sequence-reading probes. For each hybridization cycle, 0.2 uM of UK0-12 anchor probe and 0.4 uM of the BBNNNNNN probe were incubated with the array in a ligation/hybridization buffer containing T4 DNA ligase at 20° C. for 10 minutes. Excess probes were washed off at 20° C. and images were taken with a TIRF microscope. Bound probes were stripped to prepare for the next round of hybridization.

Figure 6:
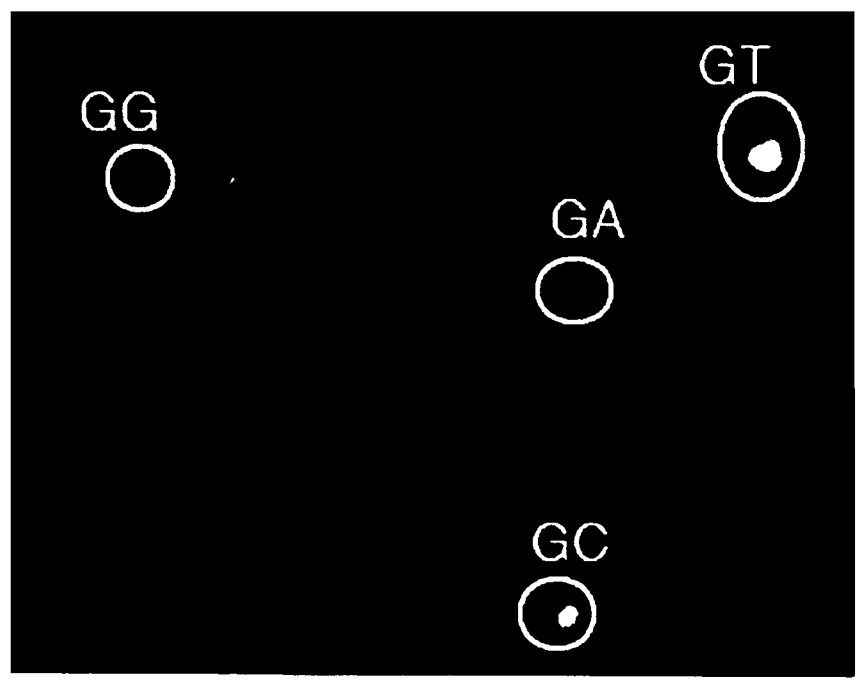
FIG. 6 is an image of concatemers of DNA fragments that contain a segment of degenerate bases, pairs of which are identified by specific probes.

Using a subset of the BBNNNNNN probe set (namely GA, GC, GG and GT in the place of BB), spots were able to be identified spots on the concatemer array created from targets that specifically bind to one of these 4 probes, with an average full match/mismatch ratio of over 20, as shown in FIG. 6.

DEFINITIONS

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683, 195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" in reference to a genome or target polynucleotide, means a contiguous subregion or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length.

"Genetic variant" means a substitution, inversion, insertion, or deletion of one or more nucleotides at genetic locus, or a translocation of DNA from one genetic locus to another genetic locus. In one aspect, genetic variant means an alternative nucleotide sequence at a genetic locus that may be present in a population of individuals and that includes nucleotide substitutions, insertions, and deletions with respect to other members of the population. In another aspect, insertions or deletions at a genetic locus comprises the addition or the absence of from 1 to 10 nucleotides at such locus, in comparison with the same locus in another individual of a population.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. A "hybridization buffer" is a buffered salt solution such as 5×SSPE, or the like. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999), which are hereby incorporated by reference in its entirety for all purposes above. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476, 930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213. Enzymatic ligation usually takes place in a ligase buffer, which is a buffered salt solution containing any required divalent cations, cofactors, and the like, for the particular ligase employed.

"Microarray" or "array" refers to a solid phase support having a surface, usually planar or substantially planar, which carries an array of sites containing nucleic acids, such that each member site of the array comprises identical copies of immobilized oligonucleotides or polynucleotides and is spatially defined and not overlapping with other member sites of the array; that is, the sites are spatially discrete. In some cases, sites of a microarray may also be spaced apart as well as discrete; that is, different sites do not share boundaries, but are separated by inter-site regions, usually free of bound nucleic acids. Spatially defined hybridization sites may additionally be "addressable" in that its location and the identity of its immobilized oligonucleotide are known or predetermined, for example, prior to its use. In some aspects, the oligonucleotides or polynucleotides are single stranded and are covalently attached to the solid phase support, usually by a 5'-end or a 3'-end. In other aspects, oligonucleotides or polynucleotides are attached to the solid phase support non-covalently, e.g. by a biotin-streptavidin linkage, hybridization to a capture oligonucleotide that is covalently bound, and the like. Conventional microarray technology is reviewed in the following references: Schena, Editor, Microarrays: A Practical Approach (IRL Press, Oxford, 2000); Southern, Current Opin. Chem. Biol., 2: 404-410 (1998); Nature Genetics Supplement, 21: 1-60 (1999). As used herein, "random array" or "random microarray" refers to a microarray whose spatially discrete regions of oligonucleotides or polynucleotides are not spatially addressed. That is, the identity of the attached oligonucleoties or polynucleotides is not discernable, at least initially, from its location, but may be determined by a particular operation on the array, e.g. sequencing, hybridizing decoding probes, or the like. Random microarrays are frequently formed from a planar array of microbeads, e.g. Brenner et al, Nature Biotechnology, 18: 630-634 (2000); Tulley et al, U.S. Pat. No. 6,133,043; Stuelpnagel et al, U.S. Pat. No. 6,396,995; Chee et al, U.S. Pat. No. 6,544,732; and the like.

"Mismatch" means a base pair between any two of the bases A, T (or U for RNA), G, and C other than the Watson-Crick base pairs G-C and A-T. The eight possible mismatches are A-A, T-T, G-G, C-C, T-G, C-A, T-C, and A-G.

"Mutation" and "polymorphism" are usually used somewhat interchangeably to mean a DNA molecule, such as a gene, that differs in nucleotide sequence from a reference DNA sequence, or wild type sequence, or normal tissue sequence, by one or more bases, insertions, and/or deletions. In some contexts, the usage of Cotton (Mutation Detection, Oxford University Press, Oxford, 1997) is followed in that a mutation is understood to be any base change whether pathological to an organism or not, whereas a polymorphism is usually understood to be a base change with no direct pathological consequences.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $\gamma_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" or "oligonucleotide" are used interchangeably and each mean a linear polymer of nucleotide monomers. As used herein, the terms may also refer to double stranded forms. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moities, or bases at any or some positions, when such analogs are incompatible with enzymatic reactions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 9 to 40 nucleotides, or in some embodiments, from 14 to 36 nucleotides.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the position and fluorescence intensity of a signal being generated at each hybridization site of the microarray; thus, such a readout may be registered or stored in various ways, for example, as an image of the microarray, as a table of numbers, or the like.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Reference sequence" or "reference population" of DNA refers to individual DNA sequences or a collection of DNAs (or RNAs derived from it) which is compared to a test population of DNA or RNA, (or "test DNA sequence," or "test DNA population") by the formation of heteroduplexes between the complementary strands of the reference DNA population and test DNA population. If perfectly matched heteroduplexes form, then the respective members of the reference and test populations are identical; otherwise, they are variants of one another. Typically, the nucleotide sequences of members of the reference population are known and the sequences typically are listed in sequence databases, such as Genbank, Embl, or the like. In one aspect, a reference population of DNA may comprise a cDNA library or genomic library from a known cell type or tissue source. For example, a reference population of DNA may comprise a cDNA library or a genomic library derived from the tissue of a healthy individual and a test population of DNA may comprise a cDNA library or genomic library derived from the same tissue of a diseased individual. Reference populations of DNA may also comprise an assembled collection of individual polynucleotides, cDNAs, genes, or exons thereof, e.g. genes or exons encoding all or a subset of known p53 variants, genes of a signal transduction pathway, or the like.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation. Tm=81.5+0.41 (% G+C), when a nucleic acid is in aqueous solution at 1M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Sample" usually means a quantity of material from a biological, environmental, medical, or patient source in which detection, measurement, or labeling of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A random array of concatemers, wherein said random array comprises:
   (a) a solid substrate comprising a surface, wherein said surface comprises a plurality of discrete spaced apart regions defined on said surface, wherein said discrete spaced apart regions are separated by inter-regional areas;
   (b) concatemers randomly disposed on said plurality of discrete spaced apart regions such that at least a majority of said plurality of discrete spaced apart regions comprises a single concatemer immobilized thereon and said concatemers do not bind to said inter-regional areas, wherein said concatemers comprise a plurality of monomeric units and each monomeric unit comprises:
   (i) a first target sequence of a target polynucleotide of unknown sequence;
   (ii) an adaptor comprising a Type IIs endonuclease restriction site, wherein said first target sequence is adjacent to said adaptor; and wherein each said single concatemer is immobilized on a discrete spaced apart region by attractive noncovalent interactions between said discrete spaced apart region and multiple monomeric units of said single concatemer.

2. The random array of claim 1, wherein said plurality of concatemers are immobilized on said discrete spaced apart regions through attractive noncovalent interactions.

3. The random array of claim 2, wherein said attractive noncovalent interactions are a member selected from Van der Waal forces, hydrogen bonding, ionic and hydrophobic interactions.

4. The random array of claim 1, wherein said surface comprises silica.

5. The random array of claim 4, wherein said discrete spaced apart regions comprise functional moieties.

6. The random array of claim 5, wherein said functional moieties comprise amines.

7. The random array of claim 1, wherein said adaptor further comprises a palindrome.

8. The random array of claim 1, wherein a majority of said concatemers disposed on said discrete spaced apart regions have a nearest neighbor distance of about 50 nanometers or greater.

9. The random array of claim 8, wherein said majority of said concatemers have a nearest neighbor distance of about 200 nanometers or greater.

10. The random array of claim 1, wherein said majority of said concatemers are disposed on said discrete spaced apart regions at a density of at least 1000 per $\mu m^2$.

11. A random array of concatemers, wherein said random array comprises:
(a) a solid substrate comprising a surface, wherein said surface comprises a plurality of discrete spaced apart regions defined on said surface, wherein said discrete spaced apart regions are separated by inter-regional areas;
(b) concatemers randomly disposed on said plurality of discrete spaced apart regions such that at least a majority of said discrete spaced apart regions comprises a single concatemer immobilized thereon and said concatemers do not bind to said inter-regional areas, wherein said concatemers are immobilized on said discrete spaced apart regions through attractive noncovalent interactions, and
wherein said concatemers comprise a plurality of monomeric units and each monomeric unit comprises:
(i) a first target sequence of a target polynucleotide of unknown sequence;
(ii) an adaptor, wherein said first target sequence is adjacent to said adaptor; and
wherein each said single concatemer is immobilized on a discrete spaced apart region by attractive noncovalent interactions between said discrete spaced apart region and multiple monomeric units of said single concatemer.

12. The random array of claim 11, wherein said attractive noncovalent interactions are a member selected from Van der Waal forces, hydrogen bonding, ionic and hydrophobic interactions.

13. The random array of claim 11, wherein said discrete spaced apart regions comprise functional moieties.

14. The random array of claim 13, wherein said functional moieties comprise amines.

15. A random array of concatemers, wherein said random array comprises:
(a) a solid substrate comprising a surface, wherein said surface comprises a plurality of discrete spaced apart regions defined on said surface, wherein said discrete spaced apart regions are separated by inter-regional area;
(b) concatemers randomly disposed on said plurality of discrete spaced apart regions such that at least a majority of said plurality of discrete spaced apart regions comprises a single concatemer immobilized thereon and said concatemers do not bind to said interregional areas, wherein said concatemers are immobilized on said discrete spaced apart regions through attractive noncovalent interactions, and
wherein said concatemers comprise a plurality of monomeric units and each monomeric unit comprises:
(i) a first target sequence of a target polynucleotide of unknown sequence;
(ii) an adaptor comprising a Type IIs endonuclease restriction site, wherein said first target sequence is adjacent to said adaptor; and
wherein each said single concatemer is immobilized on a discrete spaced apart region by attractive noncovalent interactions between said discrete spaced apart region and multiple monomeric units of said single concatemer.

16. The random array of claim 15, wherein said concatemers are generated from a circular template, wherein said circular template comprises said adaptor and said first target sequence.

17. The random array of claim 15, wherein said target polynucleotide is a genomic sequence.

18. The random array of claim 15, wherein substantially all of said plurality of discrete spaced apart regions have at most a single concatemer attached.

19. The random array of claim 1, 11, or 15, wherein said discrete spaced apart regions are prepared by photolithography.

20. The random array of claim 1, 11, or 15, wherein said inert interregional areas comprise hydrophobic barriers.

21. The random array of claim 11, wherein said discrete spaced apart regions are arranged on said surface in a rectilinear pattern.

* * * * *

SEQUENCE LISTING

```
<160> NUMBER OF SEQ ID NOS: 18

<210> SEQ ID NO 1
<211> LENGTH: 80
<212> TYPE: DNA
<213> ORGANISM: Unknown
<220> FEATURE:
<223> OTHER INFORMATION: probe
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
```

```
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(80)
<223> OTHER INFORMATION: n is a, c, g, or t

<400> SEQUENCE: 1
nnnnnnnngc atancacgan gtcatnatcg tncaaacgtc agtccangaa tcnagatcca      60
cttagantgn cgnnnnnnnn                                                 80

<210> SEQ ID NO 2
<211> LENGTH: 50
<212> TYPE: DNA
<213> ORGANISM: Artificial sequence
<220> FEATURE:
<223> OTHER INFORMATION: Synthetic Oligonucleotide also described as an
      adaptor

<400> SEQUENCE: 2
tatcatctgg atgttaggaa gacaaaagga agctgaggac attaacggac                50

<210> SEQ ID NO 3
<211> LENGTH: 15
<212> TYPE: DNA
<213> ORGANISM: Artificial sequence
<220> FEATURE:
<223> OTHER INFORMATION: Synthetic Oligonucleotide also described as an
      adaptor

<400> SEQUENCE: 3
accttcagac cagat                                                      15

<210> SEQ ID NO 4
<211> LENGTH: 25
<212> TYPE: DNA
<213> ORGANISM: Artificial sequence
<220> FEATURE:
<223> OTHER INFORMATION: Synthetic Oligonucleotide also described as an
      adaptor
<220> FEATURE:
<221> NAME/KEY: misc_feature
<222> LOCATION: (1)..(7)
<223> OTHER INFORMATION: n is a, c, g, or t

<400> SEQUENCE: 4
nnnnnnngtc cgttaatgtc ctcag                                           25

<210> SEQ ID NO 5
<211> LENGTH: 22
<212> TYPE: DNA
<213> ORGANISM: UArtificial sequence
<220> FEATURE:
<223> OTHER INFORMATION: Synthetic Oligonucleotide also described as an
      adaptor
<220> FEATURE:
<221> NAME/KEY: misc_feature
<222> LOCATION: (1)..(1)
```

```
<223> OTHER INFORMATION: biotinylated base
<220> FEATURE:
<221> NAME/KEY: misc_feature
<222> LOCATION: (16)..(22)
<223> OTHER INFORMATION: n is a, c, g, or t

<400> SEQUENCE: 5
atctggtctg aaggtnnnnn nn                                              22

<210> SEQ ID NO 6
<211> LENGTH: 20
<212> TYPE: DNA
<213> ORGANISM: Artificial sequence
<220> FEATURE:
<223> OTHER INFORMATION: Synthetic Oligonucleotide also described as an
      adaptor
<220> FEATURE:
<221> NAME/KEY: misc_feature
<222> LOCATION: (1)..(1)
<223> OTHER INFORMATION: biotinylated base

<400> SEQUENCE: 6
cttttgtctt cctaacatcc                                                 20

<210> SEQ ID NO 7
<211> LENGTH: 16
<212> TYPE: DNA
<213> ORGANISM: Artificial sequence
<220> FEATURE:
<223> OTHER INFORMATION: Synthetic Oligonucleotide also described as an
      adaptor

<400> SEQUENCE: 7
agatgataat ctggtc                                                     16

<210> SEQ ID NO 8
<211> LENGTH: 65
<212> TYPE: DNA
<213> ORGANISM: Artificial sequence
<220> FEATURE:
<223> OTHER INFORMATION: Synthetic Oligonucleotide also described as an
      adaptor

<400> SEQUENCE: 8
tatcatctac tgcactgacc ggatgttagg aagacaaaag gaagctgagg gtcacattaa     60
cggac                                                                 65

<210> SEQ ID NO 9
<211> LENGTH: 23
<212> TYPE: DNA
<213> ORGANISM: Artificial sequence
<220> FEATURE:
<223> OTHER INFORMATION: Synthetic Oligonucleotide also described as an
      adaptor
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (23)..(23)
<223> OTHER INFORMATION: dideoxynucleotide

<400> SEQUENCE: 9
nnnnnnngtc cgttaatgtg acc                                             23

<210> SEQ ID NO 10
<211> LENGTH: 17
<212> TYPE: DNA
```

```
<213> ORGANISM: Artificial sequence
<220> FEATURE:
<223> OTHER INFORMATION: Synthetic Oligonucleotide also described as an
      adaptor
<220> FEATURE:
<221> NAME/KEY: misc_feature
<222> LOCATION: (17)..(17)
<223> OTHER INFORMATION: didexoynucleotide

<400> SEQUENCE: 10
agatgatatt tttttc                                                          17

<210> SEQ ID NO 11
<211> LENGTH: 24
<212> TYPE: DNA
<213> ORGANISM: Artificial sequence
<220> FEATURE:
<223> OTHER INFORMATION: primer

<400> SEQUENCE: 11
tcagcttcct tttgtcttcc taac                                                 24

<210> SEQ ID NO 12
<211> LENGTH: 30
<212> TYPE: DNA
<213> ORGANISM: Artificial sequence
<220> FEATURE:
<223> OTHER INFORMATION: probe

<400> SEQUENCE: 12
ggatgttagg aagacaaaag gaagctgagg                                           30

<210> SEQ ID NO 13
<211> LENGTH: 80
<212> TYPE: DNA
<213> ORGANISM: Artificial sequence
<220> FEATURE:
<223> OTHER INFORMATION: probe
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 13
nnnnnnnngc atancacgan gtcatnatcg tncaaacgtc agtccangaa tcnagatcca          60
```

```
cttagantaa aaaaaaaaaa                                                    80

<210> SEQ ID NO 14
<211> LENGTH: 30
<212> TYPE: DNA
<213> ORGANISM: Artificial sequence
<220> FEATURE:
<223> OTHER INFORMATION: probe

<400> SEQUENCE: 14
ggatgttagg aagacaaaag gaagctgagg                                         30

<210> SEQ ID NO 15
<211> LENGTH: 11
<212> TYPE: DNA
<213> ORGANISM: Artificial sequence
<220> FEATURE:
<223> OTHER INFORMATION: probe

<400> SEQUENCE: 15
cattaacgga c                                                             11

<210> SEQ ID NO 16
<211> LENGTH: 11
<212> TYPE: DNA
<213> ORGANISM: Artificial sequence
<220> FEATURE:
<223> OTHER INFORMATION: probe

<400> SEQUENCE: 16
tgagcgattc g                                                             11

<210> SEQ ID NO 17
<211> LENGTH: 12
<212> TYPE: DNA
<213> ORGANISM: Artificial sequence
<220> FEATURE:
<223> OTHER INFORMATION: Synthetic Oligonucleotide also referred to as
      an adaptor

<400> SEQUENCE: 17
acattaacgg ac                                                            12

<210> SEQ ID NO 18
<211> LENGTH: 11
<212> TYPE: DNA
<213> ORGANISM: Artificial sequence
<220> FEATURE:
<223> OTHER INFORMATION: probe

<400> SEQUENCE: 18
ggtgtcatgg a                                                             11
```